(12) United States Patent
Ryan

(10) Patent No.: US 7,964,357 B1
(45) Date of Patent: Jun. 21, 2011

(54) ISOLATED GENOMIC POLYNUCLEOTIDE FRAGMENTS FROM CHROMOSOME 12 THAT ENCODE HUMAN MOUSE DOUBLE MINUTE 2 HOMOLOG

(75) Inventor: James W Ryan, Augusta, GA (US)

(73) Assignee: Ryogen LLC, Suffern, NY (US)

( * ) Notice: Subject to any disclaimer, the term of this patent is extended or adjusted under 35 U.S.C. 154(b) by 0 days.

(21) Appl. No.: 12/795,864

(22) Filed: Jun. 8, 2010

Related U.S. Application Data

(63) Continuation of application No. 10/608,463, filed on Jun. 27, 2003, now Pat. No. 7,754,424.

(51) Int. Cl.
*C12Q 1/68* (2006.01)
*C07H 21/02* (2006.01)

(52) U.S. Cl. .......................................... 435/6; 536/23.1

(58) Field of Classification Search ...... 435/6; 536/23.1
See application file for complete search history.

(56) References Cited

U.S. PATENT DOCUMENTS 6,184,212 B1  2/2001  Miraglia

OTHER PUBLICATIONS

Andersen et al., 1996, Mammalian Genome 7:780-783.
Bureau et al., 1995, Genomics 28:109-112.
Muzny et al. 2003, NCBI Locus AC025423, gi:14578057.
Oliner et al., 1992, Nature 358:80-83.
Oliner et al. 1999, NCBI Locus NM-002392, gi:4505136.
Rehli et al., 1995, J. Biol. Chem. 270: 15644-15649.
Ries et al., 2000, Cell 103: 321-330.
Sigalas et al., 1996, Nature Med. 9:912-917.
Tan et al., 1989, J. Biol. Chem. 264: 13165-13170.
Watson et al. "Recombinant DNA" 2nd Ed. Scientific American, New York. 1992. pp. 137-138.
U.S. Appl. No. 10/608,463 Non-Final Office Action, Dec. 1, 2004.
U.S. Appl. No. 10/608,463 Final Office Action, May 26, 2005.
U.S. Appl. No. 10/608,463 Non-final Office Action, Mar. 8, 2006.
U.S. Appl. No. 10/608,463 Final Office Action, Aug. 25, 2006.
U.S. Appl. No. 10/608,463 Final Office Action, Apr. 16, 2007.
U.S. Appl. No. 10/608,463 Non-Final Office Action, May 14, 2008.
U.S. Appl. No. 10/608,463 Final Office Action, Jan. 2, 2009.
U.S. Appl. No. 10/608,463 Notice of Allowance, Feb. 23, 2010.

*Primary Examiner* — Tekchand Saidha
(74) *Attorney, Agent, or Firm* — Cheryl H. Agris

(57) ABSTRACT

The invention is directed to isolated genomic polynucleotide fragments that encode human carboxypeptidase M and human mouse double minute 2 homolog, vectors and hosts containing these fragments and fragments hybridizing to non-coding regions as well as antisense oligonucleotides to these fragments. The invention is further directed to methods of using these fragments to obtain human carboxypeptidase M and human mouse double minute 2 homolog and to diagnose, treat, prevent and/or ameliorate a pathological disorder.

1 Claim, No Drawings

SEQUENCE LISTING

<160> NUMBER OF SEQ ID NOS: 4

<210> SEQ ID NO 1
<211> LENGTH: 443
<212> TYPE: PRT
<213> ORGANISM: Homo sapiens

<400> SEQUENCE: 1

```
Met Asp Phe Pro Cys Leu Trp Leu Gly Leu Leu Pro Leu Val Ala
1               5                   10                  15

Ala Leu Asp Phe Asn Tyr His Arg Gln Glu Gly Met Glu Ala Phe Leu
                20                  25                  30

Lys Thr Val Ala Gln Asn Tyr Ser Ser Val Thr His Leu His Ser Ile
            35                  40                  45

Gly Lys Ser Val Lys Gly Arg Asn Leu Trp Val Leu Val Gly Arg
50                  55                  60

Phe Pro Lys Glu His Arg Ile Gly Ile Pro Glu Phe Lys Tyr Val Ala
65                  70                  75                  80

Asn Met His Gly Asp Glu Thr Val Gly Arg Glu Leu Leu Leu His Leu
                85                  90                  95

Ile Asp Tyr Leu Val Thr Ser Asp Gly Lys Asp Pro Glu Ile Thr Asn
                100                 105                 110

Leu Ile Asn Ser Thr Arg Ile His Ile Met Pro Ser Met Asn Pro Asp
                115                 120                 125

Gly Phe Glu Ala Val Lys Lys Pro Asp Cys Tyr Tyr Ser Ile Gly Arg
130                 135                 140

Glu Asn Tyr Asn Gln Tyr Asp Leu Asn Arg Asn Phe Pro Asp Ala Phe
145                 150                 155                 160

Glu Tyr Asn Asn Val Ser Arg Gln Pro Glu Thr Val Ala Val Met Lys
                165                 170                 175

Trp Leu Lys Thr Glu Thr Phe Val Leu Ser Ala Asn Leu His Gly Gly
                180                 185                 190

Ala Leu Val Ala Ser Tyr Pro Phe Asp Asn Gly Val Gln Ala Thr Gly
                195                 200                 205

Ala Leu Tyr Ser Arg Ser Leu Thr Pro Asp Asp Asp Val Phe Gln Tyr
210                 215                 220

Leu Ala His Thr Tyr Ala Ser Arg Asn Pro Asn Met Lys Lys Gly Asp
225                 230                 235                 240

Glu Cys Lys Asn Lys Met Asn Phe Pro Asn Gly Val Thr Asn Gly Tyr
                245                 250                 255

Ser Trp Tyr Pro Leu Gln Gly Gly Met Gln Asp Tyr Asn Tyr Ile Trp
                260                 265                 270

Ala Gln Cys Phe Glu Ile Thr Leu Glu Leu Ser Cys Cys Lys Tyr Pro
                275                 280                 285

Arg Glu Glu Lys Leu Pro Ser Phe Trp Asn Asn Lys Ala Ser Leu
290                 295                 300

Ile Glu Tyr Ile Lys Gln Val His Leu Gly Val Lys Gly Gln Val Phe
305                 310                 315                 320

Asp Gln Asn Gly Asn Pro Leu Pro Asn Val Ile Val Glu Val Gln Asp
                325                 330                 335

Arg Lys His Ile Cys Pro Tyr Arg Thr Asn Lys Tyr Gly Glu Tyr Tyr
                340                 345                 350

Leu Leu Leu Leu Pro Gly Ser Tyr Ile Ile Asn Val Thr Val Pro Gly
                355                 360                 365
```

His Asp Pro His Ile Thr Lys Val Ile Pro Glu Lys Ser Gln Asn
    370                 375                 380

Phe Ser Ala Leu Lys Lys Asp Ile Leu Leu Pro Phe Gln Gly Gln Leu
385                 390                 395                 400

Asp Ser Ile Pro Val Ser Asn Pro Ser Cys Pro Met Ile Pro Leu Tyr
                405                 410                 415

Arg Asn Leu Pro Asp His Ser Ala Ala Thr Lys Pro Ser Leu Phe Leu
            420                 425                 430

Phe Leu Val Ser Leu Leu His Ile Phe Phe Lys
        435                 440

<210> SEQ ID NO 2
<211> LENGTH: 491
<212> TYPE: PRT
<213> ORGANISM: Homo sapiens

<400> SEQUENCE: 2

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

Thr Met Lys Glu Val Leu Phe Tyr Leu Gly Gln Tyr Ile Met Thr Lys
    50                  55                  60

Arg Leu Tyr Asp Glu Lys Gln Gln His Ile Val Tyr Cys Ser Asn Asp
65                  70                  75                  80

Leu Leu Gly Asp Leu Phe Gly Val Pro Ser Phe Ser Val Lys Glu His
                85                  90                  95

Arg Lys Ile Tyr Thr Met Ile Tyr Arg Asn Leu Val Val Val Asn Gln
            100                 105                 110

Gln Glu Ser Ser Asp Ser Gly Thr Ser Val Ser Glu Asn Arg Cys His
        115                 120                 125

Leu Glu Gly Gly Ser Asp Gln Lys Asp Leu Val Gln Glu Leu Gln Glu
    130                 135                 140

Glu Lys Pro Ser Ser Ser His Leu Val Ser Arg Pro Ser Thr Ser Ser
145                 150                 155                 160

Arg Arg Arg Ala Ile Ser Glu Thr Glu Glu Asn Ser Asp Glu Leu Ser
                165                 170                 175

Gly Glu Arg Gln Arg Lys Arg His Lys Ser Asp Ser Ile Ser Leu Ser
            180                 185                 190

Phe Asp Glu Ser Leu Ala Leu Cys Val Ile Arg Glu Ile Cys Cys Glu
        195                 200                 205

Arg Ser Ser Ser Ser Glu Ser Thr Gly Thr Pro Ser Asn Pro Asp Leu
    210                 215                 220

Asp Ala Gly Val Ser Glu His Ser Gly Asp Trp Leu Asp Gln Asp Ser
225                 230                 235                 240

Val Ser Asp Gln Phe Ser Val Glu Phe Glu Val Glu Ser Leu Asp Ser
                245                 250                 255

Glu Asp Tyr Ser Leu Ser Glu Glu Gly Gln Glu Leu Ser Asp Glu Asp
            260                 265                 270

Asp Glu Val Tyr Gln Val Thr Val Tyr Gln Ala Gly Glu Ser Asp Thr
        275                 280                 285

Asp Ser Phe Glu Glu Asp Pro Glu Ile Ser Leu Ala Asp Tyr Trp Lys
    290                 295                 300

Cys Thr Ser Cys Asn Glu Met Asn Pro Pro Leu Pro Ser His Cys Asn
305                 310                 315                 320

Arg Cys Trp Ala Leu Arg Glu Asn Trp Leu Pro Glu Asp Lys Gly Lys
            325                 330                 335

Asp Lys Gly Glu Ile Ser Glu Lys Ala Lys Leu Glu Asn Ser Thr Gln
        340                 345                 350

Ala Glu Glu Gly Phe Asp Val Pro Asp Cys Lys Lys Thr Ile Val Asn
    355                 360                 365

Asp Ser Arg Glu Ser Cys Val Glu Glu Asn Asp Asp Lys Ile Thr Gln
370                 375                 380

Ala Ser Gln Ser Gln Glu Ser Glu Asp Tyr Ser Gln Pro Ser Thr Ser
385                 390                 395                 400

Ser Ser Ile Ile Tyr Ser Ser Gln Glu Asp Val Lys Glu Phe Glu Arg
                405                 410                 415

Glu Glu Thr Gln Asp Lys Glu Glu Ser Val Glu Ser Ser Leu Pro Leu
            420                 425                 430

Asn Ala Ile Glu Pro Cys Val Ile Cys Gln Gly Arg Pro Lys Asn Gly
        435                 440                 445

Cys Ile Val His Gly Lys Thr Gly His Leu Met Ala Cys Phe Thr Cys
    450                 455                 460

Ala Lys Lys Leu Lys Lys Arg Asn Lys Pro Cys Pro Val Cys Arg Gln
465                 470                 475                 480

Pro Ile Gln Met Ile Val Leu Thr Tyr Phe Pro
                485                 490

<210> SEQ ID NO 3
<211> LENGTH: 99680
<212> TYPE: DNA
<213> ORGANISM: Homo sapiens

<400> SEQUENCE: 3
taattacaac tttaaacacc aaaccacagt catgttggca ctcagaattt gaatccttat      60
ctactgggct ccagaatctg tacttttttaa tttatttact tatttctgag acagggtttt    120
gctccgttgc ttagactaaa gtgctgtggt acaatcacgg cttactgcag ccttgacctc     180
ccgggctcaa gcgatcctct tgcctcagcc cctgagtag ctgggaccac aggtgtgtgc      240
caccatgccc aactaatttt tgtatttttt gtacagatga gctttcgcca tgttggctag    300
gctggtattg aacttctaga ctcaagtgat ccacccacct cagcctccca aagtgctagg    360
attacaggtg tgagcccaga atctgtactt ctaacaacaa aaatagtttc taatacatac    420
aaaatacttg ataggcctga tggaggataa aggaattaat aaagtatatt ttgtgtcctc    480
cgggagctta ccatttagtg gaggaaatat gtattcccac aaataactgt ggggcaccaa    540
gttatgagta cttttacctc cactccaatc tgccactggc tactgagcaa tggtccaagg    600
ttagagcatc atatttagcc atagtataca ttggcatgct tactggggttg tgtggcagca    660 ataaatggca actgaaccaa aagatgcagg agtctagcaa gactttttac ttctggagca    720
atttcaggct tccaaatcct tactgaatta cccttaattg caatttctcg tattactgag    780
atgatgagag tctaatcatt gagactattt cctcctaact tgttgctat atgcaggcaa     840 ccaagcttca ttctgactgg gggttacgct aacttggatt ttaaaaccca attctgcagt    900
tcaagagaga tgataaatgg agtagaggga cctcctccct accctccccc caaacccccc    960
aaagccttcc caactcccta tatactctaa aagacagaca ctagaaacta acaacacat    1020 aatctgatgg gctgatcaat aatgcattgg ttttattacc tgaatatttt ggggttactt    1080

```
tttcatgtca gtctctcatg tcaaaaattc tcatttccct aatgcctacc ccctcaggcc    1140
ctcatctctc ttccatcttc ctcacgaatg ataatttaag gtcataaaac agatagcttc    1200
acactttcaa tataaactcc aaaaaataaa ttgttagcgg tatttatctg acccctatat    1260
tctagctatt atagtcagat aataaaatcc agggtgctcg agggaacaga tcaaggggac    1320
agttagaaaa cttaagcttc agtgtttctg ttgactctag aaaggcaaaa ctaaaataac    1380
tcatctgtag cctgaatatc attcccaata ggagttagat aaaagcctat cttggcaaag    1440
ctcaaagtcc ttaaagtttg ggtcttattt gtttgtttgt tagactattt tggatcttga    1500
gagtttgctt tgggatgggg aacagctatt agagctgttt ggcgagtggg tatgctagaa    1560
atgggttgaa attatgacat tagtataaat ttttataaaa atctaatttc tagactgggc    1620
aacatagcaa gaccttgtct ctactaaaat aaaaaaaaat tttaaaaaag ctggccatgg    1680
tggcacacac ctgtagtccc agctacttcg ggggctgagg cagtaggagc ccttaagcct    1740
gggaagtcaa ggttgcagtc agccctgatt gtgcaactgc attccagcct gggcaacaga    1800
acaagaccct gtctcaaaaa aaataataat aaataaaatt agtcattata taaaaattct    1860
ttcttttctt ttttttttt tgagacagag tcttactctg ttgcccaggc tggagtgcaa    1920
tggcgcgatc tcagctcact gcaagctccg cctcccaggt tcaagtgatt cttctgcctc    1980
agcctcctga gtagctggga ttacaggtgc atgccaccat gcctggctat ttttcatatt    2040
tttagtagag atatggtttt gccatgttgg ccaggctggt cttgaactcc tgatttcagg    2100
tgatctatgt gtcttggcct cccaaagtgc tgggattaca ggcatgagcc attgcacccg    2160
gcctcaaaat tatttctaat gtgtgcaaag atatctgata aaaactacat gactatgtaa    2220
aataaaacat actatttcct ctgcctggac tttctatttc ttcacccttc aagttacagc    2280
ttaaacagat ccatcttctg gaagcttttt tgaactccac ttaactccat ttcaactcaa    2340
tgagcacctt ctgtgctctt gaatgcaggt ttctgatgac tttggaggtt gtgccactgg    2400
aatagaggga aaaaacttct aggactttca tggagagctt atgtgttcat gaatattgag    2460
cagaacagga gttatttgca tggactgagc aaacagaaga ccaaaataat cttttttatga   2520 ttttttgctt aaaacgttgc ttattctttg tgttttttcag agtcaagaaa actttttat    2580 ttggagctat ttcagctttt taacaactga gtaaaataca ctccagtgag caaattttgg    2640
agcgcatttc tttctctcta ccttatttct ctgtaatttg gaaactatgt ctacgtatac    2700
ttaatttatg gtagtatcgc tatttgcata agttcagtaa gcatctgttt tcttttgtaa    2760
caggacacta ttagagacac tagttatttt accaaggctt tgactggaat gacatgtttt    2820 cagactttc agactgcttt gaggaattga ggttgagcta cagagctgat aaaaattcct    2880
tggaaaaact ggccaccttg tttttacaag gttcccaacc tgtggtaagt aaaaatgtcc    2940
ctttctgata ggcctaggaa tcccaagtta tttttggtacc tctagaaatg aggaattcat   3000
tcaattcata caggtatctg caggcacaaa taaatctttg gctgggctca agatgctttt    3060
aaaaggtcta atctgagatt ccttattaaa aaaacatcca gcaaagccaa ttttttaaaa    3120
aggcctatat agcaaataat tattcatgtt atgtttcatg caaacaatta ggcctagtat    3180
aaataaaacc aaagcttatt ttgcaaataa attggtcctg ctatgatttg tctttggtaa    3240
aaatggggga aaactggaga gggaaaaatt atgtttcaaa aaaaacctat agcatgcctg    3300
ttattagatt ctagccttgg ctgggcacag tggctcacac ctgtaatccc aacattttga    3360
gaggccgagg caggaggatg aatcacttga gcccagaagt tcgagaccag cctgggcaac    3420 ataggggagac cccatctcta caaaaaatta tttaaaaatt agctgggtgt ggtggtgcac    3480
```

```
acctgtagtc ccagctactt ggaaggctga gatggcagga tcactttagc cctagaggtc    3540
gaggcttcag tgagctctga tcatgccact gcactccagc ctgggcaaca gagtgagaca    3600
ctgtctcaaa aaaaaaaaaa aaaaaaaaaa agaaagaaag aaaagaaaag aaaaaaattc    3660
tagccttgtc cattgtttgt gagcctatac taatgactca catctgattg gttcttgggg    3720
atatttacct gaatccctca aggcttcaga tcagttctgc aaggactcct gaagctaaga    3780
ctttcacacc ttgcattagg tctcttgtag tttactgttc tcttaagtgc tatactaacg    3840
atgtggataa gaatactaac gtttttgtta taccaacatt ggggacccaa caaggcacct    3900
gggaatacat acagacaact gcaaaatggt ttcactcctc ttaccttggg ggcaacccttt   3960 gccccaacta tacccctgt caacaggaag agcagttgtc agccttttcc catctcccca    4020
gctcacacct caggattgag gtgtgctgaa gcacaaggga gggaactgaa accacctttg    4080
caaagattat gacagcaaga aaagtctaac ttgactgact ccatcttgct tctagtctca    4140
caggctggct gtctttgcta attcctgggg gcacaaagag ctaaccatgg gagggattta    4200
gtttatagtt tcacttggaa gcaaggatga taacagtccc tccctaaaac taatctcctc    4260
cttgcttaga gagtgaaaac taatgaaagg ccacaagatt agggttattg gagggacctg    4320
aattctgcta aagtataggt atacttttat aatcccttac tgctcaggag tcatgtggcc    4380
agaggtcaca agatttgtga cttccccaat tgctcttata gataacatca ctactgtaga    4440
acttaagatt ggtctcttga gatgtttttc agattttgt attctggcca tcaactgatc    4500
ctacctggac tcatgactca tgactcaact ggtcctgtgg cccccaccca gaggcagact    4560
cagctcactg ggacagtttt ccacacccct atgatttttt tcccaactaa tcagcagtac    4620
ccattaccta gtccccgccc accaaactat cttaaaaat cctaacgtct gagttctcag    4680
aaagactgat ttgagtggta actccagtct ttctgctctg ctgccttgtc acttctttat    4740
tgtaatttaa aaaaaaaaaa caaaaacaa ggtgaaggag ccaggcatgg tgtctcatgc    4800
ctatcattcc tgtattttgg gaggctgagc tgggcggatg acttgaagcc aagagtttga    4860
gaccatcctg tgcaacgaag tgaggcccca tatctacaaa aaataaatta tctgggtgtt    4920
gtggcatgtg tctgtagtcc caactgctca gaaggctgag atgggaggat tgcttaagcc    4980
cagaagttca aggcttcagt gagctatgat tataccactg cactccagcc tgggcaacag    5040
agcaagaaac tgtctaaaaa gaaaaaagt aagtacgttc tgatagtatg tctcataata    5100
tcctgtaatt ttcttttctgt aataggcatc aaaatggcaa ctgagtgact gcttatctct    5160
gtatcatctt tcccaataca atatgaactc tatcaaagtg aggactatgt ttctctttta    5220
caccatggta ttcatagtgc ttagcatatt attagatgtt cattaaataa ttatcaacag    5280
aaggaatgaa tgaaccaatt aatcatgagt catgaggaga caaagaatt tgtttggcta    5340 ttgtctgagt atatttataa tttgactttc cagaggtcat tgttgaatag atatgatgta    5400
tgctgttttc aaaagggtca ttgaaaagta aatgattaga tgaacttaca aattattaac    5460
tatcttcaaa cagtctcttt gtcactctgc tatatataca tttttccctt cttcccacac    5520 tcccctgcc tttctttctg ctacaggtac agggtattaa caaagatggc agattctttc    5580
tcaaatatac agttttaaa aaaaaaaaaa tccagaaatg gttttctcga catttgaaac    5640
aaagctagaa aagaaataaa tttcagtaag tatattgttt cctaagagac aagagtatga    5700
ctttcatctg ctgttatgtc agattgtttg atatcacaca atccagatta aatgcagcta    5760
aataggactg tctttgcttt ggaaatcggc cttattagag ccaagaagct ttcttgcaaa    5820
tctataatat aaacaaagta tagtaggaga agtaagcatt attttgcact caaagaccat    5880
```

```
gagtttaaga gaaaaagtca ctattgtaac aattgctttg taattgtaaa ttatcacaaa    5940
tttatggttg ataaaggtct attccactat tgcaaatatg ttggaaggag ctgggatgtg    6000
gaaataaata agataaatat aaacatatac tatctgttgt atccctttct gtcttgttca    6060
tcttcactag atggtaataa taataaaaat gaattcagct tgggacttat aaagcattta    6120
taacaggcca gacactgttt gttctaaact ctttgtatat gttaactcat ttaatatatg    6180
caaccctgta aggtcactat aatcctctaa gatcaatacc atgagttagc ccagtttaca    6240
gaaaaggaca tgaatgcacc aagaggtgca gtgacttgct cagggcacac agtaagcgac    6300
agagctgggg tttaagctaa gatggtgtgg ttccacagac cttactttta ataatttact    6360
attttagtta ttacatataa tctcttgatg ctatattctt cctagaataa cacttataaa    6420
tcagcaagca tgcactgagc tctgacctag atgccatggg ggaaacaaaa aatgacacca    6480
tttgatgctt cactcactct atttggggtg tcttcctgaa ctgaaattaa tttcaaacgt    6540 ttagatttt cctgacattg tttctcagct gatgtgttag ggcatactgg agtgtcaaac    6600
tttgatctga ttcatttta attttgcttc accaacagta gatagaatgt gaagctaaga    6660
aggtcatgct gtgcagtaca gaatgtggta caaaccacta ggggataaga cacaagaagc    6720
agaaagtaat attatgccag ctccccaaga aagatcacag gtttctttga acatgtgaaa    6780
ttctttagtg gagattttg gctcttgtag aatgtaagct acctaagggc agagatttgt    6840
tctgtcttgt ttacagtcgt attccctagg agcaagtgca gtgcctgaca cagagtaaac    6900
aataaataat tgataaggaa atgaatgaat aattaaaaat cagagagtgg ggcaaagcag    6960
aaataggttt actctcacag tgacatagtg ccaacaaggg acaatagtgt gataacggtg    7020
catgatttta tagtcattgc tgtgtatttt tatattcttc ctatggtacg ctttttgatt    7080
atgtagatag catttttta gtccttttct ttctttgtgc catgaaaaat tctaggattc    7140
agaaatttat cacgaacaca aatgtgtata caaatccttt ctaaatctct caaaggaata    7200
ctaatgcatt tacagttgca catccaaaat aaaagaacta ctctgtttgg tttttgatag    7260
acaacttgca taacaaacag aaaacacagc cacaatttct agagaaatgc ttattaaaaa    7320
gacatacagt tctaaaaaac aaagtctact aataaaaaaa taaggaaca attttttaaaa   7380 gatgcacagc caagactaca gagtccttgt tttaaacaga gaatgcttga gttgagacat    7440 attcttcaa tctctgagtc ccactgttta gacatcaccc gtggtagttt agggaaagga    7500
tcatcttgga ccttaacaaa aaccatccag ctttttcacta acaattttct tatctctagc    7560
tataaatagc aatctttcct ttctgaagaa ttgcaaggtc actttccttt tttatcaaaa    7620
acaaacaaat ccggttttgc tgggggtact gatctgagtt gggggagcta ctttgaagga    7680
ggtaggttta gtactggggg aggtaccagg agatcccagc ttaagataaa tgcccaaact    7740
ccctcagata catgagaagc agcagacaat agaaagaatc attgagcagc attagtataa    7800
ggcattatat tctacttgtg aaatttcaag aaaatgtgtc tttaaggcct aggcaggcag    7860
atcacttgag gccagaagtt cgagaccagc ctgggcaaca tggtgagact ctgtatctac    7920
aaaaaataca aaaaaaata gccatgcgtg gtggtacaca cctgtagtcc cagctacccg    7980
ggaggctcag gtggaggat tacttaagcc tgggaggtta aggctacagt gagctgtgat    8040
cacgtcactg cactccagcc tgggcaacag agccagaccc tgtctcaaaa acaaacaaac    8100
aaacaaaaaa caaaataatg taaaataagt tttaccttat tgggcgagtt atttctgagc    8160
gaccatttga tgcttcactc acactatttg gggtgacttc ctgaactgaa attaatttca    8220
aatgtttaga ttttttcctga cattgtttct cagctgatgt gttagcttta tatacacaca    8280
```

```
cacacacaca cacacacaca cacacacgta ctcagcacat cttcaaatta cttctgtagc    8340
acaaaaacac acaaattgac caatggaaca gaaataagcc agtcacaaaa agacaaatat    8400
tgcatgattc cacttatatt aggaatctaa actagtcaga cttttagaaa gaatgttggt    8460
agccaggagc aggagagaga gagaaaaggt gggttgttgt tcagtgggta tagagtttca    8520
gttttgcaag gtttgaaaaa gttctagagc tctattgcac aacagtgtgc atagagttaa    8580
cacaactgca ctgtacactt agaaacagtt aagatggtaa ttttatatgt tttatagcac    8640
aataatttaa aaaatatagg aaggacatgg tctcagaata aagggccatc ttttatcata    8700
aagaaaaatt tgcaacccaa ttccaacatg ttaaggtgtt ctcttcttgt tgtttcattg    8760
agaactgcta aaagtctcag tgcccttctc atttggatgg tggtcctact caaacgtttg    8820
gagaccaaag ccccatttgg taataagaag gatgtgttgc ctggcctggt gctctgggca    8880
tatacacttc aggagaacct ttcgtaggta ggggttaagg attggaatct gtcctgacag    8940
aacaatgtct tcacacaatt aacacatagt tcacatacta gatgaaaaca aattccaagt    9000
ggactacaaa tataaatctg ggggagggag agagggatga ataggtggag cacagggggat   9060 cactagggcc atgaaattat tctgtatgat actgtaatgt tggatacatg ccattataca    9120
tttgtaaaaa ctcatagcat atgcaatata aactatagat ttagttaata ataatgtgtc    9180
aatattggct catcaatttt aacagatgtg acacgctaac gccaagatgt taataataag    9240
ggaaactgtg tatgtgggta gggcaggaaa agggtatatg ggaaccctat actttctgtt    9300
caatttttct gcaaatctca aactgctcta aaaaaattaa ttttaaaaaa tgagatgaaa    9360
gaagaaaaat gaaaaaataa aaataccaaa gaaataaaaa tagaagaaaa tataaattaa    9420
tttataattt aagaataaac tttctaagaa tatatcaaaa aactatgaat ccagaaggaa    9480
aagactaata cacaaccaga aaaatgagca aaagctatta atagactatt ttttaaaaga    9540
agaacaataa atgttcaata agactatgag agaaatgttc agtcacatta atactaaaac    9600
ttaaaattat gagatttcat ttttatctat gaaattggca aacatttta aaagagataa    9660 tagtaatcat gaggagccaa acaggcattt tcacatatca ccagtgagga ctgtaaattg    9720
gaatgacctt tggtcagaaa aaattttttca aaacttggaa agcaaaatat gattgcataa    9780
tttgttttca tgttaggcat tgcctaacca gtccatctaa ggtgaattga atcctgactc    9840
gttattacag atttgcacat tttacaactg taaattcaaa tgttagtttg tagaaaattg    9900
gtgagatgct atattttgt ccaatggaga tataatttct gtcctgcaca gatgaaaata     9960
attttgctct gtaaagatag caccaaacat tatggtttat caccctgtaa gacattaatc   10020 agattttatat ctaatttagc aataatgtag aatgattttta gtattcttt ttatatattt   10080 atgtatatat ataggatgta tatttacata tgtatattat atatagtatg tatatacata   10140
atataaatac aatatgtata taggtatgtg tacacataat acatatacta tatgtatata   10200
tgtacataat atacataagt atatacatca tatacatata tgatgtctat atgtatagac   10260
atcatataca ttatgggatg tacatacata tatacataac atatacatat attatgtata   10320
tattattata gatatatgta catatataca tacatatatg tatgtagtaa atgtatatat   10380
agatacatat gtgtatacat atatagatgt atgtacatat atctatgtat atacttatag   10440
atgtatgtac ataatatcta tatatatact tacagatata tttatataat atctatatac   10500
ttacatatat gtactatgta tatttagata tatacacata tttatacata tatgcatata   10560
cacatataca tatatatgta tgtacatata taaatagata tacataatat atgtatatac   10620
acatatagat atatatgtac acatatagat atacgtgtgt gtgtgtgtgt atacacacat   10680
```

```
attttctcat gtctttcttt gaactggctt tgttatcctg ctggtttcct cattaataag   10740
ttaaaattaa aacttgaact gtgcttactc tatatttgta tgagaatact ttttaacatt   10800
ttttaaatta tacatttgac atttataqg agtataactt ggccaaatat tttaagtctt   10860
aaaagtgtac atgctttta acctagcaat tacatgtcta agaaatgatc ctaaggaggt   10920
aaggacatgc tcaaaggttt agctctgaga atgtttctag atgtgctgtg tataataaag   10980
aaataccaga aacaaatgtg ccacattagg gcgctggtta atacctaaat gtgtgtgtgt   11040
ttgtttgatt gttttggggt ttggggattt tttttttta agacagagtc tcattctgtc   11100
acccagaatg gagtgccatg cgatcatggc tcactgcaac ctcaaacccc tggggtcaag   11160
caatcctcct gccccagcct cctcagtagc tgggactacc ttgccccatc cctaaatgtg   11220
ttttaagaat ggttgtttcc aggtaagtaa aatttgtaag tttaaatttt ttcttttatc   11280
ttgttcagat tttcttgtga cactttcaaa gaaaaagtt tgaaagtcac aaagtctagt    11340
tatactgttc tcattcttgt tgacatctat tgaggtactt agccccgact atagttattc   11400
cctctgtccc aattcctgct actatcttag ggaaattcag agtccttaaa cagaaccaat   11460
ccaacactct ggctttttca ttccttaatt tcccatttcc agtgatcttt acctcctctt   11520
cacttttgta attcactcta agatattttg atcctgtttt cattcagaat tagtcattgg   11580
tcctctctaa cacttttgtg cttttcctc tgctttgctt ttaaattaaa atgccttcat    11640
tgtttttcca atttaaaaaa gcaatgcatg tttggtggaa aaacttttca gaaaatacag   11700
aaagatgtaa aaagaaaat taaaacattg caactcgtgg atttgcactc agcatgttgg    11760
taaccttaga aacacattgc tgggaatagt ttttttttgt ttgctttatc taaatgagat   11820
cttactattt attttacttt tattatctgc ttccttgcctg aacaatttgt ctttccaagt  11880
gaataaatgc agatctacat tgacattatt atggctgaaa acaattaat tgtacagcta    11940 taatattctt taacccaggg tgtcttaact tcagcactat tgacattttg ggctgaataa   12000
ttctttgttg tgggaggctg tgttgtgcac tgaaggatat ttaatgcctc cctgccctct   12060
gtatcagcac tagatgccag tagctcccat ccctagttat gacaatcaaa aatgtctcaa   12120
gatattgcca aatgtctgct gtgggcacta ctgcctcaag ttgagaacca ctgatctaac   12180
caatctgctg ttgtttgaca tttaggtttt atctactttg tcacaattta aagcagcagc   12240
acttatgaag ctcctaacat atacaaactc aacacatctc caaattactt ctatagcata   12300
aatttctagc aaggaatggc acatacaaaa ttttgatgtc tattcccaga tttccctcca   12360
gaaagattgt attaatttag aacaccattg aaacagcata aatgtcattt cctgagatcc   12420
tgtctacttc caggtattgt caatctttt aatcttgctt tgtgataagc aaaacaaagt    12480
attactttac ccttttaact tgtaattctt tgattgctta ccaggttggt aacctttact   12540
atatttatta gctatttgtg ttactgcttt tatgaactgc ttattcatct cctttgctca   12600
ttctttattt tgtaagagca ttaattcctt cttccagctt gtaattttc tcataacctg    12660 atttaaacct ttcttcttat aacctttata aggttttctg tacagaagtc atacatttgt   12720
atgttttcaa attattagcc tttttattat ggttttacct ttaatggtgc catacttaga   12780
aagatcacct ctaggtccag gcctggtggc tcacacctgt aatcccagca ctctgggagg   12840
ctgaggcagg cagataattt gaggccagga gttcgagacc atcctggcca acgtggtgaa   12900
accccgtctc tactaaaaat acaaaaatta gccaggcgtg gtggtgggca cctgtaatcc   12960
cagctactca ggaggctgag gaaggagaat tgcttgaacc cggagggtgg aggttgcagt   13020
gagctaaaat tgtgccactg cactccagcc tgggcaacag agcaagactc tatctcaaaa   13080
```

```
aaaaagaaga aagaaagaag atcacctcta aaatctctaa acttcagtat tttactctat    13140
taggctaacc ttttattttg ctgttatctt tcatactctt aacactaaat ttttttttct    13200
ctcttgacca gtgcaccttg aacttgaatg tacatataca tcatctggaa atcttattaa    13260
aatgtgtgtt ctgattcagt aggtttggag tggagtgaca gattctacat ttccaacaag    13320
ctcccaggtg atgccagtgc tgtccctggc ctgcactctg agttactagc tcctaaacct    13380
tcagcactca gtcctctgta cccctacct ccattctctg actccttcct gaagttgcct    13440
cccttcctac ctagtgtgaa ccccaatggc agcaatttca actatagctc atctctgttt    13500
ttccagaaca acaatcctgg caatctccat tccagtattg atgaagccac catttcttcc    13560
agtctccagc cacagcaccc tgcaggaaat cagatagtgt ccacgtactt ctcttaaaaa    13620
gataggattt ctaaggtaca tcagcaagcc ttcactttgt tcccacccag ttcccttcc    13680 cattcctaga gtaactttgc ctaaatttaa tcttctcaag ctccagtccc cctcctcaga    13740
cctcttagtc aatgaacaac aatgaaaggg aaacgtcttc aacccttcca gtggaaataa    13800
catttagcat agtgactact gcacaattaa aaaaaaaaa acctactcaa agactctaca    13860
atgtcatact aagacttcca actcttaggc caggcaaggt ggctcactca gtaatccca    13920 gcactttggg aggctgaggc agaaggatca cttgaggcca ggagttcaag actagcctgg    13980
ccaacatggt gaaacctggt ctctattaaa aatgcagaaa ttaggcatgt gtggtgtaaa    14040
aatacaaaag ttacgtaggt gtggcgatgc gtgcctgtaa tcccaggtac gttagaggct    14100
gaaacacaag aatcgcttga acctggaagg cagaggctgc agtgagctga gattgcacca    14160
ctgcactcaa gcctgggcaa cagagtgaga ctgtatctca aaacaaacaa acaaacaaac    14220
aaacaaacaa acaataaaac aacttctctt taagaaaaaa aaaagatgg ccaggcacgg    14280 tggctcacgc ctgtaatccc agcgatctgg gaggccgagg caggcagatc gcccgaggtc    14340
gggagttcca gaccagcctg gccaacatgg tgaaaccccg tctctactaa aaatacaaaa    14400
attagccggg cctggtggca ggtgcctgta atccgagcta ctcggtaggc tgaggcagga    14460
gaattgcttg aacctgagag gaggttgcag tgagccgaga tcatgccatt gcactccaga    14520
ctgggcaaca gaattgagac tccatctcaa aaaataaga aagaaataaa aaattaaaaa    14580
aaaaattcca actcttggaa aattcccttt aaagagttac gaattaagct ggtttattta    14640
tgtaataaac gcttcgcaca gttcttacaa tgtgcctgcc aaccttattt aggtaggtac    14700
aattaagact tccactttac acaccagaaa ataaggcaca gagtcgacac agccactgag    14760
tgtcagagca agaattggca ctcatcccgt gagcgcctca gttcttttt tttctttata    14820 tatactttaa gttctagggc acatgtgcac aactgtggca catatacacc acggaatact    14880
atgcagccat aaaaaaggat gagttcatgt cctttgtacg gacatggatg aagctggaaa    14940
ccatcattct cagcaaacta tcgcaagggc agagcgcctc agttcttaaa ccactcttct    15000
atgctgcggc agaatcactg gaagtctcag ggagtcctga gtgcgcaatt ctaggaaaag    15060
tatctatatc tgtaagaaag aagggggcagg gaatctaacg gttctcagct cttgaaggca    15120
cattagattc attcaaggtc ctctctaaaa atacactttc ttgggcctcc acgagaaaaa    15180
ttctattcaa ttagtcgtgg gcttgcatcc gtattttag tctgtaaaag tggaatgtta    15240
tctcaaatca gtggttttca aacttttat attctgcgga ccttgacacg ggcccccaat    15300
accctgacac ggttacttac aatccgggag agagtgggag aaaggggag agagggaagg    15360 ggagaggggg agggagaga gagagaatga atgagaatga atctttaga gaggtagagg    15420 gggttggccc gtgccacaaa ccacctctca ggtttgagtg aagccttcgt tctctctcgt    15480
```

```
gcagagacca tgccatcctt ccagaaagga gcattttagg acgttttagg acgagagacc    15540
tgtaattggc ctaagactca ggtgcaggtg gaggaagcat cggatttaca acagtggtcc    15600
tgccttcttc gatgtgactt ccagttttaa attcaattct aatttacaca aatcccaccc    15660
actatgtaaa cttgttggaa aatgtcctgc actctgcact tcgtggcatt taaaacttcc    15720
acacacgcgc gcgttctttc tcgaagcccc gtgattgctt agcctcgctg ggcagcttgg    15780
cactgctggg agcttggctc gccctgccgg ggccgacgcc gcccgtcccg caggagcccg    15840
cgcggggctc agggcactca ggactccgca tgcgtcccgg ctccaggtgg gccccggcac    15900
cgccaaccgc aggaaacccg ccgagcccta aacgtctccc aagcggctgc agtctgcgac    15960
agagagtgtc cctcggtgga gcgcctgtg gctgcccagg ctacagccgt ggccgaggcg    16020
aggacacact tctgacctgg ggctccagca aagactgtcc gcgagcggcg actccatgcc    16080
cgcagccctc cgcccagctc agccgcccgg ccgcgggcac cagcagccgc gccacgaaag    16140
ggcgcaccgc gcgggcgccg tctctcctag gtgcgaaggc ggctgaggcc ccgcccggga    16200
ggcacccgcg cggctccgga gtgggccgga gggacgtccg ggggcggggc ccgggcgcgc    16260
ccgcccctctg accgggctat aacacccggc cccgccgggc ggccgcgggt gggtagaggt    16320
gcgcgcctgg gacctggtga ggctgggggt gcgcggggcc gggcgcagct gtggcagctg    16380
ccggacggcg gaggcgccag gaggaggagg agagggaggc gcgggcggct gggtcgaggg    16440
caccgaggct gcccgtgctc ccggtctctg gttgcacggc tcactcccga aggtgttgct    16500
tccagctttt gcctccttag gaggcaggga gcgtcagtgt cggagaccc tgagaccgga    16560
gtaccgagac gtagctggtg atgccccgc ctgccctcat gtgttctcag gttcttctta    16620
tttttattca tctctagaac atggacttcc cgtgcctctg gctagggctg ttgctgcctt    16680
tggtagctgc gctggatttc aactaccacc gccaggaagg gatggaagcg ttttgaaga    16740
ctgttgccca aaactacagt tctgtcactc acttacacag tattgggaaa tctgtgaaag    16800
gtagggtccg tctcgtgaac actttgccaa accctcagtc ctcccttca gtattcatta    16860
aatatgcccc agcttcctgt ctgctcttcc acgcacctac tctgagtggc acagaacaag    16920
tcaaccggta ccgtgcgtgt tggttgtttt ctgcttttgt tgggaggaat agtaggaaga    16980
actgaatttt actggacttg tccattgtaa ttcagtgtca ctgagtcctt tccattattg    17040
gagttcttct gtctttttgg atcttgcaga cattggttat ttgggatgta tgttttagtt    17100
ccttttcaag ataaactccc aagtaagtcc gtttatccgt ttcagttccc ctttgtgtgg    17160
gcttctttat atatgacttg gactgttaat gtcatttctt catgtctctt ttaaactgaa    17220
ataatgcagt tttgttggta agatttctgt gtcatctgta gttagccttt tatttaaagt    17280
tatgcaaaac tatcatttct gcaagtttct tttaatctaa gtagtacagt tctgttggtt    17340
agatttgtgt cgtgtataat tagccctatg gcttaaagtt atgcaaaaaa gtggttctat    17400
gattaaaggc tgtttttaaa atgtatccat ttgaagaaga caatgctaga taatgaatat    17460
atattagtag tgattgaaac tcttcccagc attttcatat ttatcattaa taatttattg    17520
ttctaagtta gaaactacat aaagttattt tcatttttat agacagcaag tttgaatcag    17580
ataaattaaa taatttgttc aaggtctccc agatggtgaa ttttatagcc aggactggca    17640
cccatccggc caaggcaaat aatttgatca gatatcgtta tttcatcttt ctttctttct    17700
ttctttcttt ctttttttt tttttttttt tttggtcaga gtctcgctct gttgcccagg    17760
ctggagtgca gtggcgtgat ctcggctcac tgcaacctcc ggcttcctga gttcaagcaa    17820
ttctcctgcc tcagtctccc gagtagctgg gattacagga atgcgccacc acagctggct    17880
```

```
aattttttg tatttttagt agagatgggg tttcaccata ttggccaggc tggtctcaaa      17940
ctcctgacct tgtgatcctc ctgcttcggc ctcccaaagt gctaggatta caggtatgag      18000
ccaccgtgcc cggccgagat accattatta cttaatcatc ttttattatc ctgatgttcc      18060
caaagaggtt accagaaaac ttagtcctta aatcaaaagt ttcataaatt ttatgcaatt      18120
tggatctcaa cttttttgtaa ggtgtgttca aactctacct tgattttagc tctgaacttt      18180
tgagtcaatt gagagtctca taattaccat attcttcatc attttttcaaa aaaatcaagg      18240 ctatggcttc tatattaaag aaaaagtatt atataaatgt atttatgtgc aatgcgaagt      18300
caatatcctg ggctgtgtgt aatagtaact ttgtttttaa acagcattgc caaagagatg      18360
gtgccagaat tactctatat tgctctataa tccaaaatta tagaggttgg gtgtgtgaga      18420
aatcatatct tgaatcagca tacgtattca gccttctgaa atcattttc cctagggcta      18480 gagtagagca atttaaaaag atctaggaat actaattata ttaattaaaa atatatagaa      18540
cacaactagc ttgagttatt gttcagtcat catttcaacc acaagatgat gaggatgttg      18600
ttaattttaa gtactaagtg atttggtaag gttttgtatt ttcaaacaca atgtgcttgt      18660
gacagttggg ggctctcttt cctaatatga atcagcagtt gtgatctatc ctgcatgata      18720
tcaaaccaca atcacagtga aagtcagcag gcttaatttt gtttttaatt ttaccttgta      18780
tgcactcttg cggttaaagg cttgaggagt tatcatgtaa aaataaaatc tgacactagt      18840
ggttaaatat ttgtgttgaa tatgttgttc tgaataataa ctcggattaa gaaaaatccc      18900
aaatctgcca tttggctcca actggtagat gaaactgtat gccagtaact gggagtcagt      18960
tgccaaagtg tcactgcaca ttagtgtgac aattgagaga tggtgctcct ttgttggtgg      19020 tcttttttcac tagatatttt ccctaaccat tctgccctct gatgtaagat aagtttgctt      19080
agaaaacaga atttatgacc aggcccagtg actcatgcct gtaatcccag caccttggga      19140
ggccgaggcg ggaggatcac ctgaggtcag gaatttgaga ccagcctggc caacatggtg      19200
aaacgttgtc tctactaaaa atacaaaaaa ttaaccagac atggtggtgt gcacctgtgg      19260
ttcccgctac tagagaggct gagaccgag aatagcgtga acccaggagg cagaggttgc       19320
agtgggccaa gatcatgcca ctgcactcca gcctgggtga caagagtgaa actctatctc      19380
aaaataaaag aaaataaaca gaatttatta tacacgtgtt atttatttat ttatttatat      19440
tacatgtatt aacgtgggca gtcttaccca gaagggaaag taatattcct aagtaactaa      19500
atacatgttt agttttttgta aaaacttaaa tatatgtgct atgcctatgt aaatatatgc      19560
atatcacata ttttctttgt tgtaattgtg gattatattc tgcttgttt ttcatttcat       19620 gttatttcct tagatatttc catgaattga caaagtcggt agatgtgaat tcgttgctgt      19680
ttagtattct atcctcttga ttatgtgaat tttcttagtc attcacctct ttgagcatct      19740
gtatagtttt tggttaactc tgttataaac agggatacta taaaaccatt gatacatgtc      19800
atgataatta ccttctatta ttattggtga ttttaaaaaa cgttttatt ttgaaacttt       19860 taaaatccac acaaaagtta aacacatcta tacccagctt cagccatagt agaccatatt      19920
tcagttgagc ctttgaagg aaatcccact gcctagtgac atagtaaaga aaatcttagg       19980
tgaaacaaga gaagcaaaaa agtactgatg acttagttca gaaaaatcag aaaaggtaca      20040
gtgttcatca gttcgttcgt tcaatcctcc gttcaattaa ggaagcacct cccattttt       20100 gccccaaccc ctttgtctag aaggatgcct ggcacataat caataatcta tatctattta      20160
tttaatggat caaatatttg ctgagcaaaa ggcatgggaa gcaaacaaac gtgtgtgtca      20220
ttcattccct gccattaggt agctcatttt caaatacaaa tgtatttact gtgaatttct      20280
```

```
cagggtagtc tctccacaca caccccaaaa ttagtttagg aacattttat tattttttta  20340
aaaaatgaac ccttgtgttg agggttgact atcaatagat agcaatgaaa gaactgctct  20400
gctacataca aaaccccaaa gggccatttt aaatgagatt tcctaccatc tattttaaga  20460
atcttgcatt gactgggtgt ggtggctcac gtctataatc ccagcacttc aggagaccag  20520
cctaggcaac atgggagact ccatttctta aaaaaaaaaa aaaaaattta attaaccagg  20580
cataatggtg catgcctgtg gtcccagcta cttgggaaac tgaggcagga gaatcacttg  20640
agcctgggag ttcaaggctg cagtgggcca tgatcgtgcc accgtactcc agcctggcct  20700
acagagcaag accctgtctc aaaaaaaaaa aaaaagtatc ttgtcttgcc tcctgctaag  20760
tctgatcatc attgtatctg aatacagtag gcgggataat aacaccttcc ttactagtga  20820
taatactatt agagattttt taaagccagc caaatttagt agtctctgtt atcaagtact  20880
ttccatgtag taaatagttt aagacattat ttcgatctca gcaactcaaa gtaggcctta  20940
tcctcattta caaacaggt aaaatgaggc acagagaggt taattaactt gctgaagata  21000
acatagctaa gtattagaag attcaaactc agatctgcct atttcccaag cacctctcta  21060
ttctctttta aaaagcagct tgacatttaa gtctttaatc catcttgaat taattttgt  21120 ataaggtgta aggaagggat ccagtttcag cttctacat atggctagcc agttttccca  21180
gcaccattta ttgaataggg aatcctttcc ccattgcttg ttttctcag gtttgtcaaa  21240 gatcagatag ttgtagatat gcggcgttat ttctgaggtc tctgttctgt tccattgatt  21300
tatatctctg ctttggtacc agtaccatgc tgttttggtt actgtagcct cgtagtatag  21360
tttgaagtca ggtagcatga tgcctccagc tttgctcttt tggcttagga ctgacttggc  21420
aatgcgggct cttttttggt tccatatgaa ctttaaagta gttttttcca attctgtgaa  21480
gaaagtcatt ggtggcttga tggggatggc attgaatcta taaattaccct tgggcagtat  21540 ggccattttc acgatattga ttcttcctac ccatgagcat ggaattgttc ttccatttgt  21600
ttgtatcctc ttttatttca ttgagcagtg gtttgtagtt ctccttgaag aggcccttca  21660
tgtcccttgt aagttggatt cctaggtatt ttattctctt tgaagcaatt gtgaatggga  21720
gttcactcat gatttggctc tctgtttgtc tgttactggt gtaagactta aacgttagac  21780
ctaaaaccat aaaaaccctta gaagaaaacc taggcattac cattcaggac ataggcacgg  21840
gcaaggactt catgtctaaa acaccaaaag caatggcaac aaaagccaaa attgacaaat  21900
gggatctaat taaactaaag agcttctgca cagcaaaaga aactaccatc agagtgaaca  21960
ggcaacctcc aaaatgggag aaaattttcg caacctactc atctgacaaa gggctaatat  22020
ccagaatcta caatgaactc aaacaaattt acaagaaaaa aacagacaac cccatcgaga  22080
agtgggtgaa ggacatgaac agacacttct caaaagaaga catttatgca gccaaaaaac  22140
acatgaaaaa atgctcacca tcactggcca tcagagaaat gcaaatcaaa accacaatga  22200
gataccatct cacaccagtt agaatggcga tcattaaaaa gtcaggaaac aacaggtgct  22260
ggagaggatg tggagaaata ggaacacttt tacactgttg gtgggactgt aaactagttc  22320
aaccattgtg gaagtcagtg tggcgattcc tcagggatct agaactagaa ataccatttg  22380
acccagccat cccattactg ggtatatacc caaaggacta taaatcatgc tggtataaag  22440
acacatgcac atgtatgttt attgcggcac tattcacaat agcaaatact ggaaccaac  22500 ccaaatgtcc aacaacgata gactggatta agaaaatgtg gcacatatac accatagaat  22560
actatgcagc cacaaagaat gatgagttca tgtcctttgt agggacatgg atgaaattgg  22620
aaatcatcat tctcagtaaa ctatcgcaag aacaaaaaac caaacaccac atattctcac  22680
```

```
tcataggtgg gaattgaaca atgagaacac attggacaca ggaagggaa catcacactc     22740
tggggactgt tgtggggttg ggggagcggg gagggatagc attaggagat atacctaatg   22800
ctaaatgacg agttaatggg tgcagcacac cagcatggca catgtataca tatgtaacta   22860
acctgcacat tgtgcacatg taccctaaaa cttaaagtat aataataata aataaaata    22920
aataaataaa aataaaaagc agcttgacac agatggggat gattccatgg aagttgaggt   22980
cattagtaga gggttttagg accatggttt gggcacattt gacctgaagg tatagctcta   23040
ccaaggatct agagctgttc aattcagtag ccattagcca ctaagcaatt gaggagttga   23100
aatatgacta gaccaaactg aggtgtgcta gaaagtgact ttgaagactt aatacaaaaa   23160
aggaaaatat ttcactaata atgttttata ttgattacat gttgaaatga taatatttta   23220
gatatgttaa ataagaaata ttttttttaaa ttaatttcaa ggccaaaagc agtggctcac   23280
acctgtaatc ccagcacttt gggaggctga ggcaggtgga tcgcccgagc tcaggagttt   23340
gagacccgct ggggcaacat ggcaaaaccc catctctacc aaaaatacaa aaaattagct   23400
gcgcatggtg gcatatgcct gtcatcccag ctacttggga ggctgaggtg ggaggattgc   23460
ttgagcttgg gaggtggagg ttgcagtgaa ccaagattgt aattgtgcca ctgcactcta   23520
acctgggtga tagggtgaga cccccatctc aaaataaat aaatatataa ataaaaatta   23580
atttcacctg tttcttttta cattattgta actagcagaa gattaaaatt atatatgata   23640
cttgcattat attttgatcg gactgtgctg ctatagagtg caatttgtta ttattaattt   23700
tttcctgcgt acaaaaggaa ttctagttca tttagaaaat ttggatcata caacaaagca   23760
ccaaaaagaa aattaaaatc tcaccatcca aaggaaacat ttagtagact gcaatcatac   23820
tacacagttt tgagccttt tacccccctg agtcaaatat cttatttgt ttgtccatgc    23880
aaacatgtta tctctaaaac ttgattttta atttctgttt tgtgtcctgt caatagatat   23940
tttattgttt aacttatgcc ccactggtga atatttagtt tgtttctaaa ctttcgctgt   24000
tatgatcaat gctgtagtga acatccttgt agctaagaca gcaaaaatct gagcacaggc   24060
tttggaatca cctgcccaag ttcaaattcc ggattctcag ttttgtagct acgtgaccat   24120
gggtctttag aataattcct ggcacatagt aagtgctatg taaaagctgc tattattatt   24180
attattaata catacccaaa aaggaaatta ctaagtctaa agctgttta agtatttgat    24240
atatatacca aattgccttc caaaaagatt gtgttgattt ataatttctt gggaaatgca   24300
tattaagaaa aataaaacaa ctcttctaaa acttacacta gtcataaatc aatactgtca   24360
ttagtgcttt gaaagatgat tgtagtatgt atttctcatt gttatgttgt aagtatgagg   24420
gagaatttat ttctcttgcc ccttttcccta agaactctca ccttcccatc attaacagac  24480
attcactgaa ttcctctact aggagtccta taccatttca gatgttcaga aatctcccta   24540
acattggtta agattcttgc tcctaagagg aaagtactat gttcacatac acagatctct   24600
catgatcact tgccctcaac tggatagatt ttagccggtg attaccctc agaaaacagc    24660
attgtatata aaattttggc acaacacttg gtcatccgtc acactctgct catttcccaa   24720
atatgctcgt aaaaccagtt tgcttgagat cctgtataaa atgccattg tgatgcaaat    24780
actgacatat tgaggatgaa tatgaagaaa accactaaaa tctaggaaat tcagctataa   24840
tatacatgtt tgtgatttaa agttatatgg gtttagtaag ccttcccct ttaacataat    24900
acgcagagta cctttctgag acatttatca gctatcagcc ttattcttat tcttgaaaca   24960
ttcagggttt cttaaagaca ttgccttttt ttttttctca tatggagtct cgctctgtcg   25020
cccatgctgg agtgcagtgt cacaatgtcg gctcactccg cctcctgggt tcaagcaatg   25080
```

```
ctcctgcctc aacctcctga gtagctaggg ttacaggcac ccaccattgc gcctggctaa    25140 ttttggtag  agacagggtt ttaccatgtt ggccaggctg gtctcgaact cctgacctca    25200
taatctgccc atctcagcct cccaaagtgc tgggattaca ggcgtgagcc actgcgccct    25260
tcctatcact tatcttgtca tgcttacatt attccccaca attttaggtt tttttttttt    25320
ttttttttaa gtagacacag gtgtctcact atgtagccca ggctggtctc gaactcctga    25380
gctcaagtga tcctcctgcc tcagcctccc gtagctctag gattaaagga atgagccact    25440 gtccctccg  cccacaattt tctaatgtcc tccatagggt aagatgagct tacaattatc    25500
tgagcctaaa accaaaatct tttttgtata caaatacaaa atatttcccc ccaacagttt    25560
taatatatac tgaactttc  agggatgcca ctatatgtaa attgagggga aattatattt    25620
tgttttgctc ttaacgtgac tgagagatat ttcatattca gagaatcctg acaacagtga    25680
acaaagagcc aaaccaatct gcatttgtaa tctatatgtt cacggtgact ctcaagtata    25740
gatacaagca tgtgatttct ttgtcttcta gtggagtacc caagttattg catatggata    25800
ccatatctta tgtaaattgc attcttttt  tatttctgct ttatatagtt tgaacactat    25860
attgatcttt tgaaattatg tatgtaaatg tgttagaatt gtatgccagc atgataaaat    25920
agaagttgca aaatattgga tatgaaagca agaggcatca tctgatagag ttaagaacta    25980
ttggtgtaaa agcacaaaga gagctgttaa ggacccactt gaagctcatg tggccagcat    26040
ccaaaaggtg cttagtttct gttcttaatc cctgaacgtg tgtatctgac ggtaacactg    26100
tggttacagc agtatctaca tttgagatgt gataactgcc attagtcctg attcctcctt    26160
tcagtttgtg tgtttagaac accccttct  ctaagaatgc aaagtaagaa agtaagatgt    26220
aaaaaaaaaa acaaaagaaa accttaaagt gaaattactc aaaacacaca cacacacaca    26280
cacacacaca cacacacaca cacacacaca cacacactct atatcaaata ccaacatgca    26340
tttgggttaa gggaaggaga ctaagtcaaa tttagtcaaa tcttcctgtt tggagctagg    26400
cttggtcctg tagtcccagc tacttgggag gtttacacag gagaatcact tgaacccagg    26460
agtttgaggc tgtactgcac tatgatcgca cctgtgaaca gccactgcac tccagcctgg    26520
gcaacacagc aagagtctgt ctcttaaaa  caaacaaaca acaaacaaaa aacacttctg    26580
tctagtgatt taaacaatt  gacattcttc ctagcaatta aatgtaatac tgtatagtag    26640
tttgtgaaga ggttagtaag tcctaatttg aatttgtgtt aaaataaaag acacaaaatg    26700
cacattaaaa atgtttctca tctctgtttt ctgaggactg ctgcatgtca caggttttaa    26760
aaatacacat tttctatctg tgacctttca catacatacc tttgtcaagc tcaactggag    26820
ggcttaatct ccactgcatc aaaaaaaaaa aaaaaaaat  gctgccaact tcaaacaaat    26880
tgccttggag ctggcttcac agagttatca cgcacttacc cggagttgaa gataactacc    26940
ttgacagtgg ggatacaaag gcagtaatga tagtgcctac tacccagtc  tttagtctat    27000 cacagaattc aggagaagcc aattaagtaa tccttctgtt tgtttaaaga actttcaatt    27060
agttgcttat ccagttttta aattattctg atgcaaatcc gtgaaaacta gaaccacact    27120
taaaaatcac aactaaagta tcatgaattg acagttattc aaacacataa ctaagcctcc    27180
tttcccacat aatacacacg cacatataca aatacaggca ggtgaaattt agcataacat    27240
catgttttta gagcacgaat aaatgttaga gaccatttga tcattcatta cgttaattga    27300
aacttagttc aaaatgttgc ttcctccagg aagcttttt  ctattccctg ggcagagtca    27360
gaatctcctt ccacacctct tctcctcttg agcatcttcc agtaactcta tgttcacata    27420
gaggccaagg accaggcttt gttcagcttt gtatcctagg cactaagatg tgcttattac    27480
```

```
atgtaacaga tactctcaag gacaaagatt aagagttatt atgtgcttat taaatgaaac    27540
atatgaatgc aaatatattg tatgtagtat attaaataat acataagtat ataggatgta    27600 cattttaaa  tatactttta tattgttaca tatattatat gtaactttat acacttttat    27660
atagttacct atattgtatg taagttcttc agtccctcaa gaaaatgaca ttgttttctt    27720
atgaactttt tgttaaaatt agttttatat tagtagtaaa taatatgata acttagagag    27780
gtagaattgg gggaccacaa ttatgcccca gttcaagata agtcactggc atgtaggaga    27840
aggcctcaga gaagttacgg actttcaggc agtaaaggac acagttgaat tattcactgg    27900
ctagcctaaa atgggtctac ccccacccct tgccttcagc cccctaaaac actgaccaaa    27960
catgtaataa gaaagagta  attataggag gttcaccacc atcacactca cccctgcctt    28020
cattaagaag tgtttaggct ggttgcggtg gttcacacct gtaactccag cactttggga    28080
ggctgaggcg ggtggatcac ttgaggccag gagtgcaaga ccagcctggc caacatggtg    28140
aaaccccatc tctactaaaa ttacaaaaat tagccgggca tggtggcagg tgcctgtaat    28200
tccagctacc tgggaggctg aggcaggaga tcgcttgaa  cccgggaggt ggaggttgca    28260
gtgagctgag agccgagatc acaccactgc actacagcct gggtgacaga gcaagactct    28320
gtctcaaaaa aaaaaaaaaa gtgtttaaat aaatgcctct ggctttattt gaacagtcca    28380
ggaataattc aagggtctgt cacagaattt tgacaaagaa aaaaggtggg agggatcatg    28440
tgaagaaggc cttttttccc ccaagagtta agcaggggcc aggcacagtg gctcaggcct    28500
gtaatcccag cactttggaa ggccaaggca ggccgattgc ttaaggccag gagtttgaga    28560
acagcctggc caacgtggca aaccccgtg  tgtactaaaa aaatgcaaaa aaaaaaaaa     28620 ttagccaggc atggtggtgc acacctgtaa tcccagctac tctggagtct gaggcgggag    28680
aatcacttga acccaggagg tggaggttac agtgagccga gactgtgcca ctgtactcca    28740
gcctggccca cagtgagtct ctgtctaaaa aaaaaaaga  aaaagaaaaa gaaaagaaa     28800 aaaaagctt  aagcagagat atgaaaccct tccattttaa gtgtctttc  ccccctctat    28860 actcagaaat gttgtactta ttttaggtga aggcagatga tatgtctaac tattcttgct    28920
gtgagtggtc cagaagggca cagttttgga aatacacaga tgaactgttg aaggtagttt    28980
caccttaatt tttagtcctt gttaaatatt tattcccttg tccattgttg gtgactcagt    29040
tgagcccact cgttaaaatc cttttcacgg ggatagtcac tcttatgaaa acatagacac    29100
ctagagacat gtgggaagcg tagggtcatt taacatgtgg cgattctaca gcagttttcc    29160
cattgtttaa ctggagagat ttatttacag cttgtgttag gctgttcttg ggttgctaga    29220
aagaaatact gggtaattta taagaaaag  aggtttaatt ggctaagcgt tctgcaggct    29280
gcacaagcgt ggccccagca tctgctcagt ttctagggag gcatcaggag gcttttactc    29340
atggcagaag gtgaagcagg accaggcacg tcacatggtg aaagcagaaa caagagaaag    29400 aggggtggg  aggtgccaca cgcttttaaa caaccagatc tcgtgagaac tcactcatta    29460
ttgtgaggac aacaccaagc catgagagat ccactcccat gacccaaacg tctcccacca    29520
ggctccacct ctaacatggg ggatgacatt tcagcatgaa atttggggga acaaatatct    29580
aaactattca caccttacta ataatactaa atgtgcacag ttaaatttca gataaagatt    29640
gttcaattgg ggcagacacg taattttttc cattgctctt tgggactcag atgaataatc    29700
ttagtgtggt agagataagc ctagctggtt tgtcatgtgt tactgtcagt tcctttcaat    29760
ttatgaagaa acagaaagat aaattgggaa atgtcacatt ctagccttga cgaacttttt    29820
agttggactt ggccatcttt cgagttgtaa gaacatgtac ttctaagggt acaaaatgtg    29880
```

```
tttccaaact ctatggcata cagttctagc ataacaccat gtcagtcaat tgcagaaact   29940
tccaaacatt ttttacactg agagctcttt ggtcaaataa ttcttgcttg gaagtaaatc   30000
ccagtctgtg tgtgccaggc actgtgttag gctagagaca gagtcatgag caaatagcat   30060
ctctgctctg atgtttctta catgtgctag tgagggaggc aaacaaaaaa caaggcgagt   30120
tcagattttg atcattgcta tgaagcaaat acatagttta gtataatgga gagtgacagt   30180
tactgtggaa cataggttcc atgaaagcat ggagcctatc ctacttgtca ctgtattttc   30240
agtgcctaaa acatagcagt tactgtttga gagaatgttg tatggaaaga atgacaggag   30300
gcctgcctga aaagatggta ggttaaagtg gagatctgaa aggtgacagt cagctagatc   30360
ttatagcctg attacaaagt gcacaaagtg caagtgatgt gcaaaggcct cgaggtggaa   30420
agagtagaac agaagtgaga ccagggtggc tggagcccag tgagcaaggg gaaagtggtc   30480
tttgagcaag ttggaaggta cacaggggac agagcataga gtgccttcta agccaattct   30540
aaagtggaga gtttgaattc tgttctgaga ataatgggaa accattgaag ggttttaaga   30600
agagagtgat gcaatctgat gtgggtttta gaaagataac tttagctgct gaatacagaa   30660
aatggccaga atagaagcag ggagactaat ccagttacag tagtcctggc aaatgttgat   30720
gatggtgatt tggattaaga tgctctgtta ggaatggagg caagtgaaag gattggaaat   30780
ctgttttgga aataaaacca agagtacttg ctaatgggtt gggttgggtt gggttggatt   30840
ggattggatt ggattggatt ggattagatt ggattggatt ggaggaggaa ggcgtgtgag   30900
cagaagagga aaatcaagga tgatgcttag gttttgtgct cgactgagtg tatgaagtgt   30960
tcttatgtta gatggacaaa actggaagag gacagatttg ggatgaaatc aagggctctg   31020
attcagacat tttctttaga aattgtgaac tcctcaggag gtatccagtg gagacggttg   31080
ggtatataag tggagctcaa gagagaagtt tggctgcaga agaaagttg ggagtcatca    31140 acatagaaat ggtattgaaa cctgcaggac taataaaata atctagcaag agagtagaga   31200
taaagaaaag aaggccagaa tcgagctata gcaccgtcac acagttagtc tgatagagta   31260
gaggagccaa gaatggagat gggaaaagat cagtaatgag gtagaaggaa aattaagagt   31320
gatgtcacag atgtcaaaaa ggggagtggc tcaagaaggc agttgttttg gggagtacca   31380
tgaccaccta ctagtgattt gctggaagga ctcactcacg actcaatata gaatcatatt   31440
caaggctaag atttattaca gcaaagggta tggtgcagga acagcaggat acagatatat   31500
ggtggcaaaa ctagagaagt cgtagtaggc tttcttgtcc tctctctgta gggattccac   31560
atgtttctca ggaatgcatg tttctctcca gctgtaaact gcagagacat atgcaaaacg   31620
cctccaccca ggaaagccca ctcaagtctt agggggttcag agctggtcaa gggagctggt   31680
cgtgtagcta tgtaaccagc caggatgcag acccccaaact aggtactagg atgcatcagg   31740
aatcttcatg tcaactttaa acaatgatac tgtcttgata tattttgacc actgccttga   31800
gggcacaaaa ataacataac taattagtaa gcatttcagg gagtttagtg ctcaggattt   31860
gggtcagggt cattgctgtg actgcaggtg ttcccaaaga caagcaagaa ctgagtaaaa   31920
catactggct atgttaactc tttcctctag aggtcatggt taatgttgaa tgcaggtgaa   31980
agtcaaaact gagagccata aagttaattt ctatatccca agtatagtt agtgaaatta    32040 tatttctctc cagatagatt cattccactt atttagtaaa catttattga atgcctaata   32100
tagttcatgg catgtgctag catgagacta taggggtaaa taagttagac atggcacctg   32160
ccctgaagga gttgacaaac caataaaacgc agatgtcatt agctgtgtgc gagaatatga   32220
cagaggtctc acggctgaga cctgaaggat aagagatcag ccaggtgaaa agggaaaggc   32280
```

```
gaggcaataa atagcacgtt caaaggcctg gaggtgaagg agcatattga ctttgaggag   32340
caaaagaagt tcagtgtggc tggaggggag aaaggagaag gtgagtgtgg ggtagattat   32400
ggaggacctt atacaggctg ttaaacacgt tttgcttcat ccacggggag atataatcct   32460
aagggttttt gcttgatagg aaaatgacag atttgttttc ttgattgaaa aatttctgat   32520
aattttacag ttagttttgc attgcaacag agattctctc tctctctctc tttttttttt   32580 ttttttttg agacaagagt ctcgctctgt cacccaggct ggagtgcaat ggtgcgatcc   32640
cagctcactg caacctccgc ttcctgagtt caagcgattc tcctgcctca gcccccgagt   32700
agctgggatt acagggtgt gccaccatgc ccagctaatt tttgtattta gtagagat   32760 ggggtttcac catgttgtcc aggttggtct cgaactcctg accttgtgat ctgcctgcct   32820
cagcctccca aagtgctggg attacaggca tgcaccaccg tgcccagccc agagattctc   32880
tttaagaaat ttggtgcaac agtcatttct gggacaaaaa gtagtgagaa aatacaaaca   32940
caccagggta aataaaccag agcgccacaa aatgtaatat taagtgtgta aaaataataa   33000
tccctgagag ctatcagtgt gaaaagtttt tatttgaatg ccgtaattga atggaattgt   33060
tcatttaaac cttcaagtga atttatttt atgtctaaaa cttattagaa atgtttcaat   33120
ggtgattata tgtagtttct ttttgcctt caacagagca cagatcacac agaaaggaat   33180
gatttttttt ttaatcagca attttggaga caaattctat gaatgccaac ctatacagaa   33240
actgacaagc attaattatt cagaatgtaa agagaaatgc cagagtatta aggaacagat   33300
acctagattt aaacataatt ttggaatatt ataattatta tgaattacaa ccacttatat   33360
ttgaggcagt atgtaacagc tgtgtgcgtg agcaggaaca tgagagggaa cgtaacctgg   33420
tctcattttc tagacaagcc attcaagagg agcaaagaga gtgggaaaat gaaagcaatg   33480
ccactactga ttattgaaca tctttatctg ccatgcactg tgctaggccc tttacacatt   33540
ttccttcttt aagctattta aaaactgcga taagttcctt acattcccat tttataggca   33600
agagcaaata gattttacag atgaagaaat tgatgtccca aaatgatatc ttggtaggtg   33660
atagattcgg ttcggtaacc caaatgtgtc ttttagcgat ttatgtattc attcaacaaa   33720
tattcattga gttcctactg tctaccagaa cttttgtaag gggatgcaaa gaagaacaga   33780
cccaggtctt tccctttatg aactagggca gtgggcctta cacccaactg ccgtaatggg   33840
aaaagcattg taatgggct tgttcgtta cagtcaacag tgcagtgtag ggatgctttg   33900
taagctggcc tacagggtga ttggtaaagt tgagaaaggc ttatcaggga ggctgacatt   33960
tgaacaaagg tttggatatt accaggcaga gagatggagg tggtaggaat tccaggtaaa   34020
gcgactggga aaacacatgc tgtgcttggg tggcaggagc agtccaggga ggacatggtg   34080
ggactgtgct gcaagaagcc ttgtatgcca aggagatgag acttcccttg tacatacagc   34140
caaggataag aatttgatga cgatttctaa tgtatcttag catctaagtt cccttaattt   34200
gtgctcactg gaaaccacag agttttagaa ggcttttgtc attgtggttt aaaagaaaaa   34260
aatagattgt tcaaagaaca gtgatacata gggaaaatat tttgactcag gaacgtaatt   34320
tctcactaaa attggcaata tttgtagccc catgggaact atgtttccat aggacattct   34380
gttcgctgtc cttgggaagc tatctaaaaa aagaagaaaa aaacacaata aaaagaggta   34440 tttgggatc agtaataaaa gttgtatact ttattgaatg tgttactgtg tactagctac   34500
ttatccatat tattttaaat cctgacacct attaaataat aggtagtatt atccctgttt   34560
tacagatagg aaactgaggc tcagaaaaaa gtgcttgcc tgagactact tagctagtaa   34620
ggagcagagc tgggaattca aacccaggtc tgtcaggatt caaaacccca gttcttccag   34680
```

```
tctctagagc ctggtctcta gagcctggag acttctgtgg aggtgaccta ggccacttca    34740
ataggtgagg agacagagga ccgcttgggg atgcattcct taaatcagag cagctgattc    34800
tatgaatgcc aacctaatac agaaactgac aaacattaat tgttcagaat gtaaagaaaa    34860
ctgccagagt atgaaggaac agacatctag attaaacat aattttggaa tattgtaatt     34920
attattaatt acaaccactt acatttgagg tagtgtgtaa cagctgtgtg catgagcagg    34980
aacttgagag ggaacgtatc ctggtctcat tttctaggca agccattcaa gagcagcaaa    35040
gagaatggga aaatgaaagc aatgccactg ccgattattg aacacctta tgtgccatgc     35100 actgtgctag gctcttaca catttcctc ttttaaatta tataaaaact ctgtgataag       35160 ttttttaag tatacagact tttgtgctaa attggaaaac ccgtactgga acctgggggt      35220
gggggcgggg cagaggtctt ctaatgactg gccttgtgct cttaagctg cactagctat     35280 cccactttga aaagaatgtg tgaaacacag ttgcagtcat gcatactcca tctccaaaga    35340
atggattcat tcttcaggcc atagtatact gactataatt ttctgtttgt aattacccag    35400
attccaagcc tgtttatagc atttatacct gaggaatgga atagtgagga tttgaagagg    35460
ccgcagtcct tgaggttttc tttgataata atatctgtgt agctgcatca aacacaaatt    35520
tgatattctg tgtatctgta gcacaggtca tgtgactgta aattcttttg atatcttgtt    35580
gcatactgag gtcaaggaac tggctcttga tgtaattccc cgcatcctca tgggagttgt    35640
taccatcata ctctggaaaa caaatgctga gatggattaa cttttacac tgggtttccg     35700 catgggattt tataggaata aaggttccac taccagcagt gagtagcctg aagtctgcca    35760
cattgaccag gaacctttgc aagaataaac cgaggatgtg ccctctgcag gtgaatgtgc    35820
taggctctct ggggttgcca aggagtttga gtccccatcc ttgagtcccc atcaactaca    35880
tctagttgat gtacacgtga tcctttgcaa aggttctgag ccctctaaaa ctgatcaaaa    35940
ttgcatctgt tagaaaatat taaatatatt ctatatatca agccaaatac taggagcttg    36000
tgtaagcaac agagtatctt ggtggatcac gtgggtgttg ggttaggcaa aagatcccac    36060
tgttggccct ccccacaccc acatccttac tatgctctgg gcagacagag ttactccaac    36120
tatctcaaaa tgcccagaaa cccttaacca cctctactga tttgcctgta ttcaggagcc    36180
tccttcttca cagctgagat tcagacttca ttgagggaca aggtgaatga gagggtaggg    36240
gacagtaggg ggcagaatct ggtcatcagg aactttggac tttccagtga gcacagactg    36300
agatacctca ggtgctaaga ctgcagcacc cctggaggaa gactgtacac tagacaacaa    36360
caaggctggt tggcaggaca gcatctaccc agcatcctta acatccggga ggagatgatg    36420
gtgccgtgta gggacacttg accctgccca tagcagcctc agccctgtg catcctggga     36480 gtgaagtgat caggtcatgc aagtaactac atcagtcctc accactggga tcattgctac    36540 agagggggaag gcttttccct gtgtgttgga gatggagata gaagtgtatt aatgggagaa   36600
aacaaaataa gcttttacat ctgctaaatt aacagaatcc caggctgcca aaaccctgag    36660
gcttgctcaa tcagcagtcc aaactgtatt tcctctaagg gacaaattat gagctgctgt    36720
aaaggtacac acagtctagt gagaaaccat tcaattttga gggggaaact ctagggaaat   36780
agagtaagtt aaaggagtag agtgtgccag tatgagaagg caactctcct ggagtttgag    36840
ttccaaaact cagtgggctc ataggtcatg gtgtgatctt agaagtcata agtgaccaac    36900
aaggagttta ataacgcctt ttcttatact ccctcttttt acatagcctt tataccaagt    36960
tatcatctgg cagtcatttt agatataggt ttctaagtta gacggtaggg tccaaatgaa    37020
gtgtttggca aagtcatctt aattttttaa aacttgatat gaaaaagatg gtggtatcag    37080
```

```
gtattgaaat tgaggagcta tcagaatagg gaaaaattcc ccatttatgc ccatactcac   37140
aaatacacaa atatttataa acaataatga tacaggcagg catggtggct cacacctgta   37200
atcccaccac tttgggaggc caaggcaggc agatcacctg aggtcaggag ttcgaccagc   37260
ctggccaaaa tggtgaagcc ccgtctctac taaaaataca aaattagccg agtgtgttgg   37320
cgcatgcctg taatcccagc tacttgggag gctgaggcag gagaattgct tgaacccagg   37380
aggtagaggt tgcagtgagc tgagatcgtg gtattgcact ccagcctagg caacaagcgc   37440
gaaactctgt ctcaaaataa taataataat aatacaactt attttttttcc ctttgggggg   37500 cttttccagca aaaccagaa agcctattag acaaatttta aaagagctgt aacactataa   37560
taagactgtt taataatggt tgagaacaca gagcccgaag aacacagatt gcctgggttc   37620
aaatcctggt tctgctgttc agtggctgtg atcttgaact actgtcttac cctatctgtg   37680
cctagttcct atttttgtaaa atagaaataa tagttctacc tcgtaggttg tcgagagggc   37740
taaataagtt aataaacata aagtgctcag aatatgattg gcacataagt gctatggaaa   37800
tatatgctac tcttactgca gttacataaa ttgtgatatt tggcagcctt gaagcgtggc   37860
cctgccatat gctttgtgtt taaaaccctc aaactactgt ttattgaggg catctttgat   37920
gtcaggcaca gggctaggca atgttcctgc tgtatctcaa tgaatctaca caacaccccta  37980 tgaggtaaat accaatttac agctttagat actgacttgc cagtggttaa gtaacttgcc   38040
caaggccaca aagcaagtac ctggtagatt caggactgaa gcttcaagtc tagagagctt   38100
ggctccagcc gcagctgcag tttgggctga ccttgttcct gccagcacac tttgggacct   38160
gggccataca agttatagca tcctggacag accctctatt ttatagaaaa ggaacctgag   38220
gccctaggat taaatgaatt gccagaggtc actctccaaa gagactctga ggtccagatt   38280
aggaaacctg aactaacatt gaagccgtgt ctttctgtat aagatccaac tgcttgtggt   38340
atgtttggcc aaaaagactc aggttaaagt cagataccaa ataatatatt gacatctagc   38400
atatttatgc ccagatgccg tatagcaaat catccttcac tttaattagc ttatagttat   38460
atactcgaca atgtgaatga acagagaaaa acaaggtatt tttttttcat cttctaaatt   38520
tgcttgggaa attcctccgt gtcttttaca ggtttaaaaa tcatgtttaa cgataatgta   38580
gttatcttag gaaaaagacc aacccatttt tatcactctt tatcattggg ccatcacaga   38640
tgagagcttt ctatcttata gaatcatttg cacaaagtat atatgaggat atacagcatt   38700
gtatttgtag catttcttat aatagtaaaa aaatgaaatg atacagtcat ctagttaatg   38760
ccactgagtt gtacacttag aatggttaaa taacaaattt tgttatatgt gttttgccat   38820 atttttaaaaa aataatagtt taagaaacta gtgacttgta tacttaaact gagtggattg   38880
tatagtatgc aaattatgtc tcaataaaga tattttttaa aacccataca tttatccata   38940
gagaattggt cagattatgc caaacccagt caatggagta ttttacaacc tttattaaag   39000
aattaggtag atttatatgt tttgacatgg gaggatgtcc agaatatatt gtgaagtaaa   39060
aaaaaagttg atgtgcattt ccatatgctg tatacacacg tctacagttt tgtcttatga   39120
gtaacactct tgtaaatgtc attatgcaac ttggcttttt cacttatgtg tgttatgtta   39180
gaggttagta catatagaga tacctcatttt ttttaactgt ttcaaactat tctgtggtat   39240
aatcttatct tagtttattt agtcatttcc atattgatga gtctttaggt catttataac   39300
ttttagatat ttcgaagaat gctgcaataa atactgttaa acaagcacat tagctccata   39360
atttcccaag ataggcacta ctaaatcaaa aagtacatgc attttttttcc tcaagttttct  39420 ttctttcatt gatgatgctc ttcttcctcc tcttcttcct cttcttcttc ttcttcatta   39480
```

```
ttattattat tattatactt ttaagttctg ggttacatgt gcagaatgtg caggtttgtt    39540
acataggtat acatgtgcca tggtggtttg ctgcacccat caacccgtca cctacattag    39600
gtatttctcc taatgttatc cctcccgtag ccccccacc ccccaacagg ccccagtgtg     39660
tgatgtttcc ctccctgtgt ccatgtgttc tcgttgttca actcctactt atgagtgaga    39720
acatgcagtg tttgattttc tgatattctg atagtttgct gagaatgatg gtttccagct    39780
tcatccatgt ccctgcaaag gacatgaact catccttttt atggctgaat agtattccat    39840
ggtgtatatg tgccacattt tcttaatcca gtctatcatt gatggacatt tgggttggtt    39900
ccaagtcttt gctattgtga atagtgctgc aataaacata tgtgtgcata aaggtatat     39960 gcatttttgt gcttgatgga tactgacaga ttaacctaca agaggatgta ttatttacac    40020
tcccagcccc acgtgagtat gtgtatttcc ccacatccta accaacacta attttttcc     40080 attctaatgg gtgaaaaaaa aaatctccat tttaagttgc attttcactg agcatggtgg    40140
tacacaccta cagttccaga gacttaggag gtcaagatgg gaggattgtt tgaggccagg    40200
gccaggagtt caagactagc ctgggcaaca tagcaagatc ccatctctaa cgaaaatttt    40260
tttaaaaact agccaggcat gatggtgcat tcctgtcatt ccagctaccc aggacaccga    40320
ggctggatga ttgcttgaac ccagggccat ggtcccacca ctgaactata gcctgggtga    40380
cagagcgaga acctatctct acttaataat tagtagcatt tacatgattg aaaatcagaa    40440
tgaacatgtt ttcacattaa ttcaacatta gataaacatt gaggtactgc cccagatgaa    40500
caaacacaaa cccctgcccc tgtggaactt ctgttaaact ctattggtca tttctatttc    40560
ctcatgccat ttgcctgttt ttctatttat tcatgctttg ttatgtgtgt ggcaaatatt    40620
ttcacctctt ctgtggcttg tcttttgagc tccattttca gtatctttgg ccttacagaa    40680
gtttttaatt tttatgagat cgtattcgtc agtccttttc tttatgcttt tatgttccat    40740
gcctcactta aaaaggccct ctttccccca aggtcataaa tatattctat accctttca    40800 atatttttat ggttttagtt tttatgttta gcacctaact ccatctggaa tctatttttg    40860
ggaatcgagt ggtatgtaga tagatttcat gtctgacaat atatatttt gagcactcaa     40920 attttttaaaa agtatgtatg actttggtaa gcagaaagag ccaagaggag tttgaagaga    40980
cactcagaaa gtggatgtcc attctgggtg ggcccaggag tttgcaattt tagcagatac    41040
ctccagagaa aagagaaagt gatgagaaaa aaaaaaaaa agctgtgtcc tgtggagtag    41100
attcaggtca taatggctgt aggtagagac acagcagaaa gagtagcccc gggttggcct    41160
tgtatcctgg tacctacagc accttaggaa atacataaaa tacatgaaat gtcacagctt    41220
tgcaagaact agaagaccag ccagaatgaa tcagagaagg gattcttcag tgtttctact    41280
tgtaatggaa ttttaatcc ctcatctggt acaaaaatga gtttgagata atagtccatt     41340
taaaaataac ccaagccggt gtggtggctt acgcctgtat tcccagtact ttgggaggcc    41400
gaggcagggg aatcacctgt caggagttca tgaccagcct ggccaacatg gtgaaacctc    41460
gtctctacta aaaatacaaa aattagtcag gtgtggtggc gggagcctgt aatcccagct    41520
acttgggaag ctgaagcagg agaatcactt aaatccggga ggcggagatt gcaatgagcc    41580
cagatcgtac cactgcactc cagcttgggc aacagagtga gactccatct caaaaataaa    41640
taaataaata aataaataac caacccagcc ctggattaat gatgaatttt cattctggct    41700
agcaaaggtt agcaaaagtg gatgactaca tgtaggcatg ttaattaaca ctttttagat    41760
tctggaaaaa gaatgttgtg tggcagaaat atgggtacaa atgtgcaagc cttctgtaga    41820
tgattcttta aaggcaggtg gagtgggagc cgctgggcta acctacccca aatcactgca    41880
```

```
cttcctttct tcccttgtca ttaaaaccat atgacccctt tagtgtctgt gttgcactca   41940
tgagttcaga agttccaatg catctatcaa acacatgtgt ttgcctactg tgcatgttgt   42000
tctaagtgct ccttcactgc ttctgacaac cctatgaggt actattataa gcctcctttt   42060
acacatgagg aaactgaggc tccagagagt taaataagtt gcccatagtc ccacaggcag   42120
tggtggcatt gggatttgga ctcaagttgt ctagctccag gttcgcagaa tcaccctaat   42180
aatgtgccct ccaaattggc tatttcagca actgcagtgt tcaggaaaga attatactct   42240
gatgagcctt catgaggcag ggttgaaaaa cctgtgtcag gaaagatat gacaccttac    42300 tggttatcag accatgctag aaggagcctc tttaaaatcg aacaacagag ccactgctct   42360
ggtgcaagca gcactctcac ccagccctct gacctcagtc acagtgtgag ctctatagtt   42420
cctggcaaac tttagccatg gggtcaaaaa tggagaagcg tgccttcagg tataagatgt   42480
gatgtgttca tgcagggatt agctctgttt aggcttaatt ctggaagcca gggttcttaa   42540
tttggttccc attccctgac ggaatactat gcagtcctga taatgaatga tttacattta   42600
tacaacagta tgcatggatg caccacaggg gacagtgcct ggaaataggc acaagggtgc   42660
tttgaggctg ctgtctacac aaatgtgtgt ttagtttatg aaaatccaca gtggcgcctg   42720
taatcccagc actttgggag gctgaggcgg gcggatcatt tgaagtcagg agttcaagac   42780
cagcttggtg aaaacccgtc tctactaaaa atacaaaaca attagccagg tgtgatggcg   42840
gatacctgta atcccaggta ctcggaggc tgaggcatga gaatcacttg aacccaggag    42900
gcagaggctg cggtgaacca agatcgtgcc actacactcc agcctgggtg acagagtgag   42960
actttgtctc tcaaaaaaaa aacaaaatct acagtgagct cttcagcata tagctttctc   43020
tgcatattgt attccatgta ttcattgtac tggattcaat gtacagtatt ctatgtatat   43080
tgttatttca ctgaagagtt ttttcttaat ggcgtgaatt agagtcagct gaggtatttg   43140
tgaaaaatgc agactcctga actcacgcct caagattcct gttctggatg gggcccagga   43200
gtttgcagtt ttttacaaat acctcaggta attctgctgc aggtcatctg aagatatacc   43260
tgtaagaaca tagcaaagct gcagacctgg tctgctgttg atgtgcttaa tactgggcat   43320
caataggact ctataagtag agcaaaagaa tgacttgaga atgactaggc tcacacattg   43380
ggatggtagg aaaacagcct ggtgcactgc aagggtaaca ccatcttgaa gcgaaaccac   43440
cacgatgacc gatgcttgag tcctgcatgc caaggtgttc ttgcagcaag gccaagaaac   43500
aatgcctgta gcacagataa cccctcataa acatgcttat ctgacttccc cagtggtcac   43560
cagtgttccc caggaggatc tgagacatga ccagctgtct ttactctaaa cacttgctat   43620 ataaggatc atttctggtg ggtggacaca gggactcact ttctggagca gcccaagaca    43680
tcgcttctat ttgtaagtcc ctattaaata ttttttctga agaactggat ttatcagcct   43740 cttcttaag cctcttagtt ccctctgcct ttgtgggtag gtttgcgtag acctactcac    43800
caagaaacaa ggctatatct tacatgtatc catgattttt tttaatgcac aaaaatgtaa   43860
aaagactata taaataacct acaacaagat ttctgttggc caggtacagt ggctcatgct   43920
tggaatccta gcattttggg agggtgaggc gagtggatca cttgagccca ggagttcaag   43980
accagcctgg gcaacatagc aagaccctgt ctttacaaaa agtacaaaaa ttagctgggt   44040
atggtggtat gtgcctgcag tcccagctac tcaggaggct gatgtgggag gattctttga   44100
gcccaggagg tggaggcagt ggtgagctga gatcacacca ctgcactata gtctgggtga   44160
cagagtgaga ccctgtttaa aaaaagagag agagagagaa aaaaaagat ttctctgaat    44220 ccttctcatg cgtatcatga gagatgtttt aaaatgtttc tatattttgg ccgggtatgg   44280
```

```
tagttcacgc ctgtaatcct agcaccttgg gaggctgagg cgggtggatc acctgaggtc  44340
aggagttcaa gaccagcctg gccaacatgg tgaaacccccc atctctacta aaaatgcaaa  44400
cattagccag gcgtggtggt gcatgcatgt aattccagct actcgggagg ctgaggcagg  44460
agaattgctt gaatccggga ggtggaggtt gcagtgagcc gagatcacac cattgcactc  44520
cagcgtgagc gacaagaatg aaactccatc cccccaaaaa aaccactttt ctgtatttta  44580
atgcacagtt taaaaatgcc agacctggct ctattctact taggtttctg ttcattagat  44640
aggagtcatt catgtatgac tgaatcacta tgaggatcct cctctctctc ttcttcccct  44700
tccacccaca tgccaggctg tggttcagac tgccttctgc tttctcacgg gtctctgttg  44760
tgtgatcttg tgcccacctc tctgtgtgtt aaatggagag agtggcttga acagtaccct  44820
catggttggt cttcaagagc tcatctaatt ctgaatggta gttgggcatg tctgaaggta  44880
ttagcaattc tgttgctcag cattgctgat gtattgagca atgtgaaaac cttggcgaat  44940
cttgttgcca tcttccccta agaatctgcc tcatcctgaa gcccaaccat ttgactctgt  45000
ggtaaaatga agtaacttca gtaaggtcca tgtctaccaa tttcttaatc tcatttgagg  45060
taaatagatg cacattatca gaaaggactg gccactatgt actgcaaatg atgggcacag  45120
agttgtgatt gtcccagcag acttgagatg agctagggat acatcagtcc attatgagac  45180
ggtatctgtt atagtcaaga gtgtctctgg aatggcttct tgtaattatt tggactttct  45240
accaaggttt ctgtgccata gcctatggaa aagtagattc ctttcaagag acctgacttg  45300
ccaagcatgg tggttcacac ctgtaatccc agtgctttca ggggccaagg cggtgggatc  45360
acttgaaacc aggagtttag gaccagcctg ggcaacaaag tgagaccccc atctctacaa  45420
aacattagcc aggtatagtg gcgcatgcct gtggtcccag ctacatggga gggcaaggcg  45480
ggaggatcac ctgagcccag gagttccagg ctgcagtgag ccacgttcac accactgcat  45540
tccagcctgg gcaacagagc aagacccagt caaaagaaag aaagaaagaa agaaagaatg  45600
agagaaaggg agggagggaa gaagggaggg agggacggag ggacggacgg cgggacggac  45660
agagggaagg agagacagag ggagggaggc ctgacttgta tatttatgtg cacgaaatcc  45720
gttctaggcc tctgaatatg gcacctggcc cactcttttct tgagaacagt ttgccagtga  45780
gcaatgtgcc tcatgtcctt tgtgaaactg gcagagcata aattattaat ttaaaataca  45840
caaactaaga tcaagataag atgtgcttta atgaacgggt aaactcaaat ggcttattaa  45900
caccttcatt tcctcatgct gcttctgaaa tgggcatttc tcaacttaca ttttaaggta  45960
ggagctgatc tgagatgcaa gttaattata cagtttgtcg aagccaaaga gttgggtttg  46020
ggagattttc tgacctgaaa atgttcagtg gcggtgccca tgtaatcttg ggcctactct  46080
gacagacagt tcagagcctt aacattcagt gttggtcctt tggatatatt gaacataagc  46140
tacagtttac gggtatgaga ggacattatt gactgagact tcaatagttc caaggggga  46200 aaaaagaga aagatggctt ttttaaagct actgtcttca gctcaggaaa aaacatgtga  46260
tcagccgact gtaaatgcac agcttgagaa atttagcaat tcccaaaata ggttcaagtt  46320
tctttgtgag catgtaggcc tacttgcagg taacattgac tttgttaaca acgtttgtta  46380
acaataacat tgtaggcagt taatgtctca gagctcttat agatacaaaa gaaataaac  46440 ttacaacttc cagaaagcat cttctcattg atgagtctaa ataatgctca tctattggag  46500
aagcaacttg ttaatagtga cttttttgtca cttttgtaga gtggggagag ggacatggga  46560
gatgaagctc ttactttatt tgggaagtga atgtctcaa gttctttatt ctaaaaaagg  46620
taaacatcag ttgcctctga ggtagtaata gaagaaggtc tgttttactt tggaggaaca  46680
```

```
ttaaccttag agtaaaacaa acgaaaacac agttcaaagc ccaggctgtc tgagcccatc    46740
tcgtcatttg taaaatgagg ataataatac ctgccttact tatctcatgg tgtttctgtt    46800
gaggattaaa tgataaagca ctttggaaat tatgtaaaat atctgtattt taagcaggta    46860
tgatttcccg aaatccttga gttttcctc tgattccatg attatgacat cacttaaata     46920
tgccacccct ctgctatcct aatacccaa atctcagtga aacactggaa aagtccgaaa     46980
ccaatagaga tttctaaagc agatccctt attatgcccc tcaattagtg atcattgtta     47040
gtgggtctgc tcagagcatc attgccaagt gctttgataa gctgaagaaa tctgttgata    47100
atttcttgag gcatggtatt tcagtgtgtg aatacttgg gtactagttc ttgggagttt     47160
tttaaagtaa aatacttata tttgtgttga ctttgcaaca gcaggtacag caaatttcac    47220
atggtacctt gctacagaaa ttaattagta ccactcatgg tttaaattat gtagaatgat    47280
agtatgctca tattcttctt ggctgtctta aaaatgaata gaaacaaaaa ggtaaacaaa    47340
gctcatattt acctctcctt ggaaagaggt tgagtgattg tcatgtagct tctcatttat    47400
caagtatgtg ttatgatttc gttaaaggat aaattgaaag gattcttaaa gcaacaaagg    47460
tttggtcctg cattgatgca tattaagtaa agtagagctc ctcagttggc attcccaggc    47520
tgggtgacac agaggtgcct ctttctgata ctctccttcc cagctcctgt gccatcccct    47580
cccctctccc cttctctctc ctctctcccc ttcttctcct gtaatacttc tgctacttgc    47640
tctgttctac ccagagactg aaggaagtga gtggtgatct aattgagact gaataagtcc    47700
gaacatttat tttccttccc cttcactcca tccaaagtcc aatcctgagg aagacatgga    47760
ggttatgatt aaacttgccc aacactcaaa ctttactgac tgcttattct tatgttaatc    47820
acttggcctt tgctagatta atgactgagt gaccagaagt ctcaatgatc ccataaatcg    47880
tatgatttta aactatttgt gtagcttttg ctagttgtaa taaaatttt cacatgattt     47940
tttttccaaa tagagaggtt taataaagct aatgtgcttg accaggtttt ggagagttta    48000
catactaatt tcttaacccc tttctaatat ggttagtata gctctgtgtt ttcatcagag    48060
agaagcagac tgtgaattcc tcaccttggg gcttccattc tccctccagg tggcctcacc    48120
tttcaggtga acaacctgac ctctctggct cctaaatccc acccttacaa gccgcaggag    48180
ccggtgcatg ggggcatagt ttcttacctt tacctttttc aaacctttcc ctcctcacca    48240
gctttttttt aagactttat tttcttagag cagttttaga gcaaatttgc tgtacctact    48300
gtggcaaagt caatacaaat ataaatattt acttaaaacc caagaaccag tacccaaaag    48360
caaaattatc taaagcaaaa ttgagaggaa ggtacagaga tttcccacat accccttgtc    48420
cctatcccca cacgcgcata gcctctccca tgatcaatat cccccaccag agtggtacat    48480
ttgttacaac taataaacct acactgaagt aggggtttgg acaaatgtat aatgacattg    48540
tagtatcata cagaggagtt tcactgcccct aaatacccta tgtgccatct tttcatcctt    48600
ccctcctcac tagcctttgg caaccactga tcttttatt gtctccataa tttcgcctgt     48660
ttcaaaatgt catatgcttg gactcatata gtatagcctt tcagattgg cttcttttac     48720
ttagtaatat gcatttaagt ttcctccatg tatcttcatg gcttgataga tcatttcttt    48780
tcaacactga ctcgtattcc attgtctgag tgtaccacag gttatttatc ccctcaccta    48840
ctgaaggacc tcttggttcc tttcaagttt tggcaatgat aaataaaat gtaaatagct     48900
gtataatttt tatatggacg taagttttca gttatttttg ttaaataaca aggagcttgt    48960
ttgctggatc atatggcaag agtaggttta gttttgtaag acacttgcaa actgctttcc    49020
aaattggcca ttttgcattc ccaccagcaa tgaatgagag ttcctgttgc tccacatcct    49080
```

```
cgccagtatt tggtgttgtc agtgttctga attttttgcca ttctaatagg aatgcattga   49140
tatctcattg ttgttttaat ttgccttttcc ctgatgacat atgatgtgac atatgatgac   49200
atcttttcat atgcttattt gccctctgtt tatcttcttt ggtgaaatgc ctgctgtttc   49260
catcttttgt ccatttttta attgagttgt ttattttctt attgttgggt tttcagaatt   49320
ctttctgtat tttggataac tctttcatca gacatgtctt ttgcaaacat tttctccaag   49380
tctgtggctt accttttcat tctcttgatc cctccagctt tttatttaga aaattttcag   49440
tcctatagaa aaaatacaa aaatagtaaa ataagcactc acacattatt catatacatc     49500
caccagttgt taatattttg ccacatttgc tttatctctc tcatgagctc catctgttga   49560
ttttactgaa ccattagaag tgataaatgg catgtcacat catcccaaaa aacaccaata   49620
tgcatctcct aagcatgact tcttactgcc taatcatgac acatcattat taaactaaaa   49680
ataataactc agtaatatcc aacaacatac tgcattttta aagttctcca gtagttccca   49740
gaatcaaatc aagcaaggct cacccatcgt ctacagtctc acaatctagg acagttcccc   49800
tgcctttttt tggcattgac cgattcatat tgaaccaatt ttatgtcatt ggttgattcc   49860
taatgaacca tttccttgtc tacaagctct tggcttgccc tcttacagtg atgagttgga   49920
gtctctccat gacagcacca gactggaaat tcttaacatg ctttccaggc tcattaacat   49980
tgagatagtc aaaatctaca cgatgtcctc aataattttg agaacaggcc atgaaagaaa   50040
atgttgtgaa aaatgtgttt atggttaatg attcaacaca gttaacagag gtgacttggc   50100
tttctgccct gccctcatgg caacatgcgg cttcccagtt cagcactgtc ctctgctgtt   50160
agggcctggg aattctgaat gagattcagt ccttggagtt gaaaaagtaa tttacctgat   50220
gcttggtggt gtgaatgttt gtgacagttt ttgtgctaat acatttgaa ggacatgttc     50280
tctcaaaata gccccttcca ctttctgaat ccacactcca gttttctttt taacttcagt   50340
gagtggtagt ctatttgacc tgatgtgcag atcttctggc acatacattt ctgctgtctc   50400
ttggcataac aaattggcag tctatcccta tgttatgtac actgtttata ttgaaaattt   50460
gtctttaatt ggtctgatac tacatcatct gctagggcca gtagtttgtc atcagccaat   50520
ttgtacacct gaggccctca acaaacacg tgcttacaat gtttctggca ctatttttaa    50580
agcttgtaag aattaaatga gatagcacaa caaccccatg agggtaagta ccgttaatcc   50640
cataatatgg atgaggaaac tgattcattt agagggatta agcaatttgc ccaataccac   50700
atggctagta agtgacagag ctgggtttta gctctgacac tttgattctg gaacctgcac   50760
atttcatcat tatgtcagat gccctgaaga ggatactgta tatcatctca tctcacatgc   50820
tgtgttcagg caggtgacgt gctgctcaat gctggttttg atgtctttac taaactactg   50880
atctattttt gagatttaaa tctcaaaaca gtgatactag tgagaagtag tccacctttg   50940
ttaatccacc aaatgttccg gttagggaac ctaattttgg taacttcaag gcctctcctg   51000
ctattgggag ctaagcatcc ttcactctgg actctcactt gcttcacttt agaatgagag   51060
cttttaggg taaaactcag gaagtaggat gactgaaaga aaagcctttc ttctccacag    51120
tagcttatgg ggaaactagt aaattaattg ccattattcc ttgccactaa aggatgagtt   51180
cttatggtag caataaatag acaataggc tgtgcagacc tccaacaaac tgtcttttct    51240
ggggtcaaaa ggggtctgaa ttaacctctt cttaaattac agctctgtga cacctgcagg   51300
cactcataac aaataagaac accaggccag gcacagtggc tcatgcccgt aatcctaaca   51360
tcttgggagg ctgaggtggg tggattgctt gagctcagga tttcaagacc agcctagaca   51420
gcatggcaaa accccatctc tacaaaaaaa aaaaaaaat acacaaatta gccaggcgta   51480
```

```
gtggtccatg cttgtagtcc cagatactca ggaggctgag gtggctgact tgagccctgg    51540
gaggtcaagg ctatagtgag ccatgattgc accactgcat tcctgcctgg ctgacggagt    51600
gagaccaata gggcagcaag aaacaaaacc tcaacactga accggaatgt ccatgacata    51660
ctgtaaaaaa agaaacctca aatggacaat aactgtatag tgctagttgt aatgattgtg    51720 ccttttttt ttttttttt tgaaacggag tctcgctctg tcacccagac tggagtgcaa      51780
tggcacgatc tccactcact gcaacctctg cttcccgggt tcaagcgatt ctcctgccca    51840
agcctcctga gtagctggga ttacaggcac acaccaccac gcccggctaa tttttgtaa      51900 ctttagtaga gacgaggttt ccccatattg gccaggctgc tctggaactc ctgaccttgt    51960
gatctgccca ccttggccaa gaatctctt taagtattca tttgtacttt aaggtaatgc      52020
tcgatctcgc tcttagtaca gctgaattgt ccttcaaaaa gatgatctgg ttatgtttga    52080
cctcttcctc aagggaccaa aaagggaagt tctcagcttt ttatagtatg aggtccctag    52140
aggttttcac tttggggatt taaaacaag tttcctgtag ctatatggag gaaaaaaaa      52200 aaaaaaccta aagggaaca tggaagaatt ataatgattg gggcatgata attatgtcca      52260
gtttttaaaa ctccattctt aaaaatgtct tataatttat aggttaaaaa tttaaatgtt    52320
tagaggaagc aggacaggtt tatgagtctc tgacctggga atggagtggg aggaatagag    52380
aaggtggggt tgcaagagga gaaaggcaga ggaatttcct accgtcttcc tgttttttgt    52440
tgatggttag tgattaatga gacaagctgt tctgtttctc tgggagtctt gactgtcttg    52500
aagaaaaaaa agaaaattta ttgcaaccca atgcagcttc agattttcc tctattttt      52560 tttttcaatt aaaaacgtaa ctgtccctaa tttaggaact gaaattccca aacctcccca    52620
ttcacctatt caggaagaaa tgaaatggaa cctaacatct acatttcttg ggtataaatat  52680 caaaacttta atactatggg gatgaacatg taagcaaatg caactctatc tccccataat    52740
gttggaagaa tctaacttga aaccagacat ttggtttgga tcttggcact ttcttgcatg    52800
gaaatattcc aagaaggtgc attgactctt gatttgatct agaaaactgg gttctttcca    52860
gagcccaccc aggatggcac ctcatagact aactatggac ttttccatca atactggaaa    52920
acagtttcat ctaatccccg gaccaaaggt gactcggact ccaagtgagc ttcctcaggt    52980
ttgtttgtta atttatccaa tcatccattc actcagcaaa catttatcaa tcatttgcta    53040
tgtatatgcc agacactaca ccagattttg caagcacaga gatacaaaat cccttgcttg    53100
caggaaaacc tttggtttca ataaatgata ggagaggggt tgcaggggta ctatctatga    53160
aagttcaaag gaagcatcta acttagggtg gtaggggatg gggctgagca gaaggatcag    53220
gaaggtgttg gatggcagga ggcttttagc tgagccttga aaaggcaagg ggaggttggc    53280
cgctttgatg gggtgggcta aggactatcc atgcagaaga aagagcaggt attaaaggtg    53340
tcaaggcagg gagttacctc ctttgggaac tacacataaa gaagaatggc tagggcctgg    53400
tgtatgggat tggggtggga aacccaaggc aggaagaaga cagatcccaa gaggtctggt    53460
gtgcatgctg aggggatcag gtgccatctc aatgccatgg ggagtcattg aaggaaaagc    53520
agttagagcc atgggatcca gttcacatat gatcaatcac ccaaacaaag gaaagtttac    53580
tcaacaacat gttttcattt ggacttcatt ttgtcaaagc atgaaagtga tgtcagaaat    53640
agaaatgagt gtattcatgg cacaccacca cacccagcta attttttgtac ttttttgcaga  53700 gaactcctga cctcaaatga tccacctgcc tcggcctccc aaagtgctgg gattacaggc    53760
gtgagccact gtgtctggcc taaaacacat tttctaagat ttctttactt ctgggccacc    53820
tccacaaaat tttatggttc tgggaacccc tatctgaaaa agcacaggta tcagcaataa    53880
```

```
gtataatgaa cactcactag agggaaagtc attttggttt gggttggtta tggaagcagt    53940
gtcatatgaa aagggctgga ctgtactgca gaaatagaag acccacaaat tgctatggct    54000
tataacagaa aaataaagat ttagatgtca ctcatatgtc cattattgaa cagttgtgac    54060
tctgctccct gtcaccttcc ctccaggacc gaagctgaca gagcaccctc tatccaatca    54120
ttgcctgtct tatgtcagag ggaaaggaga tggcaaatca tgcatcagcc cttaaagctc    54180
tgcccagaag tggtacatta ccatttctgc ccacatttca ctggccagag caggtcacat    54240
gatatgcctg agttcattag ggcaccagat gttgggcaac caataataca acccaccact    54300
gaggtcttta ctaagaagat gacctgggcc ttagggaatg gccatgattt acctggtaga    54360
cacagcaggg gagcaaaagg aaaatatgac aatatttta tgaaatcaag acttggccac    54420
atgaaacttt tttttttttt tttttttttg agactgagtc tcgctctgtc acccaggctg    54480
gagtgcagcg gtgcgatctc ggcttactgc aacctccact tcccaggttc aagtgattct    54540
catgcctcag cctcccaagt agctgggatt acacgcacca ccatgcccag ctaattttg    54600 tatttttagt ggtgacagtt tcactgtgtt agccaggctg gtctcaaact cctgaccaca    54660
agtgatctgc cctcctcagt cttccaaagt gctgggatta caggcatgag ccaccacacc    54720
tggccgtgac acccttagaa aactaacttc aaggcagaat gcttcacagt gacaaatctt    54780
aggatgccac tttatagaaa tattctgaag agagaaaaac ccaggtgagt cagagcagcc    54840
tggggaaact tcttagaacc aggattttgt ggaattcaga ggattttaaa aggcagaaaa    54900
tccaatgaag ccattttaag ctaaaacaat gtaaataagg tggggctgtg cctagggtac    54960
tagggtgcag aaaggaacct gcctcctgtg ggcgcatttg tgttagcagg tagtgggaaa    55020
ttcgggtgga gggcaggtga tggaggaccc tgaacaccga gggaagactc tggatgttat    55080
gtgccaatat ttatcaagaa aacgcagtcc tggagataca ccataatttt tgaaatgtt    55140 acagtagata ctaattgaaa cctacagtgc gccaggcacc gttaggttag cagtgaacaa    55200
aaccagcaac ctaaacaaaa tggtgaacac accaggcagt gcccttgtgg gttacatttt    55260
ggtgagacag atagtatata gataaacaaa tatacaatct caaagagtga aaaagttgtg    55320
aagaaagatg acacaggatt agagagtgac tagggtgtat atggtggcag tggtggtggt    55380
ggtgcagcca aggggtgggg tggaggacaa gacagctgtg aagactggtg agcatgaggt    55440
agtccctggt aacaaccagc gctccacacc ctaccctcag agtgccattg cagggttagc    55500
atactccact gagtaaagct tccttgtcca ggcaatcagt tagaagagcc aggaatgctg    55560
ggcccaaaga ggttggccag agagaaaagt gcaggggaca tggttcccag atccacgcag    55620 aaccctggg gaccactgag ttccacaacc tcaacaaggc ccagggttat actaacacag    55680
caggtggcct cattttagac cccacaccag aatctgtgca acgggaaatt ccagtgcagc    55740
agaagttgga gtcaaatgcc tgcctatttc tcattccatt tgggaagcc taaacaggga    55800 agccttctgt gttcctctca ttcccatatt aaactgaact gcaaaactca tggctctaag    55860
tagactttag aattgaccta ggcagaagaa atagcccagc cccttcatta cttcagagca    55920
gaatagagca cttactctta tcacagcagc acaagacccc tgggacacct gactccctga    55980
gacccttcct tgacaggttc ccctgtccat aaacaaagtc aggaattccc agcccactac    56040
acagaatatg acagttaagc ttcattggga tcctgtggct gacctgggc aggctagagg    56100 gcatcacatc tgtacaggct ctcagctttg cgagttcaga aacagactgg gtgttcatgt    56160
ggactggccc aaacctgaaa ctctacagaa atcgcagtgc atgccaggtg gtttgccatg    56220
aaaaaaggtg tgtgtcccag agacagggtg tgtatggtac aaatggattt tgtccacgtc    56280
```

```
tttccttccc ttgccagtcc agccaccta ctgtcttttt ttttttttgt cagttttgt    56340 tttttttaa tttaagttct gggatacgtg tgcagagcat gcaggttcgt tacataggta    56400
tacatgtgcc atggtggttt gctgcacctt atcaacctgt catctaggtt ttaagccctg    56460
catgcattag gtatttgtcc taatgctctc cctccccttg cccccaaccc tccaacaggc    56520
ccaggtgtgt gatgttcccc tccctgtgtc catgtgttct cattgttgaa ctcccactta    56580
tgagtgagaa cgtgcttacc ctactttctt ttcggtttgt tttttgttt gttttgagac    56640 gagttttgct tttgttgccc aggctgaagt gcaatggtgc aacctccgcc tcctgggttc    56700
aagggattct tcagcctcag cctcccgaat agctgggatt acaggcatgt accaccacgc    56760
ccagctaatt ttgtattttt agtagagaca gggtttcgcg atgttaggca ggctggtctc    56820
aaactcccaa cctcaggtga tccgcctgcc ttggcctccc aaagtgctgg gattacaggt    56880
gtgagccacc acgcccggcc tacctaccct actttcttag cctatttgct gactagcatt    56940
caaactgagt gcagggagaa cacctagcag cctgatccca gaagtgcagc tactccacat    57000
tccacagctc tggggcagag tgactaaggc tcacctgtag tccttaaatg gagagcaatt    57060
tgggatgtac cagctaatca aataaaacca aggcagcaaa caatagccat cacttctcaa    57120
accatcctca ttgtgcccct cgactccctc cttccatttc cagttctccc cagaggggag    57180
acagacaata acctcaacaa cagaagccag tacacagcaa gcttgcttca cacgttcacg    57240
tttcttttgt ttttctttga tgttttttct ttgatgtttt ccattttcca tctctgaggt    57300
gattagcagt acagcatagt ggttaagaac agagcaggga ctccacggat agactaccca    57360
gtcttgtcct ttgttacagt ggttcttaag ctttcaggtg actgggaatc acctggagag    57420
cttattaaaa cgtagatttc cagccgcgtg aagtggctca cgcctgtaat cccagcactt    57480
tgggaggcca aggtgggcag atcacttgag gtcaggagtt cgagaccagc ctggccaaca    57540
tggctaaacc ccatctctac taaaaataca aacatgagtt ggccgtggtg gcacacatct    57600
gtagtcccag ctactctgga gactgagaca tgagagtcgt ttgaacccag gaagtggagg    57660
ctgcagtgag ccgcgattac tctaatgcac tccagcctgg gggacaaaac aacaaagcga    57720
gactctgcct caaaaaaaaa cccaaaaaaa caaaacaaca cagattactg ctccccaacc    57780
ccagagtttc tcattcagca catccaggat ggaacacaag gatgtgcagt tctaactagt    57840
tcccaggtga tactgatact cttggtacca tgaccacact ttgagaacct ctgccttatg    57900
aagtttccaa agactgttga cttgtgtgtg aaaggataac cctataccta ccacttgtgg    57960
ctattagggt taaatgagtg aatatacgta aaatgctttg agctgtgaat aataaaatgc    58020
aagcatagct agtctggaaa cttcgcccat gccttttgtc tctgttttgt ttgttaacct    58080
ccatttgttt tgtttgtaat aaaccactta gccaggtacc tcttcctctc cttcaaatac    58140
agagggcgtg tgaactttgg agaatgagtg tttaaactga cctaaataat atgtgatttt    58200
caactcttct gtggattcac tcattattca atgtgggctt tgcgtgccat atgtgataaa    58260
cttcttgtgt gtgggtata gtgggaatgt gcatacgtga aattgatgtc agatctttgg    58320
atcgttgtta gggaagataa aaggaactca cactacagtg cagccttgcc agtagggctg    58380
ttattcccac ttacgtggaa gaaactgaaa ctcagttcat tgaggaaact ctctcaagct    58440
tggacttagg tcagaggtga cttgtaagga tacacacaga gaaacatcca agcctgggaa    58500
accagctgat ctattactct gtgtaccaga actttatgta tcagaccaaa cacacaacaa    58560
gcctcacgaa aaactggaat gtgcttcaca tcactgcagc tttgtcccaa tgactgggcc    58620
acccaaggtc tctgcttctc cctaggcatg tcccattgag actctccaca tagagatagt    58680
```

```
ctgatggagt tgtgacatta acacccaatg tggaatgtcc cggtggggtg gcctcggatt   58740
cagttgtctt gttctgtaat cagtcatagc caggaagaaa gcccagtctt gctccaggag   58800
caaaccgtag cagcatgctg ctgaaagaac tgcctggga cttttttcccc agagtggggt   58860 tggctttggc ctgtctagta cttcaggga cattgaggca gccttagatc ctcagaagag   58920
cacagatctt tggaatcaga cagacttgga tttgaaccct gtttctgcca cttaagtttc   58980
ctcaactatg cattgtggct atcacacacc tcacaggtgt gaagatcaaa taacataaag   59040
tgcttagcag agtgcctggc acatagtatc tgcacttaat gaatgatagg gtttggtttt   59100
ttttttttta aattaaaaaa actggaaaga tggaaggtg aaataatta ctcagctta   59160 tcatcctatc atttagcctc ttatccctga cagtgtgcca ttttcaatcc tgtagggatg   59220
cattcattat tattaattttt ttaagagaca ggtcttgctg tgtcccaggc tggagtgcag   59280
tggcacaatc ataattcact gtaacctcaa actcctggga tcaagggatc cttgcacctc   59340
agtctcctga gtgtaaggtt cttgtattgg ttggaaccct gagagcgcgc caacagaaaa   59400
cacgaggcgg tgtgaagcaa catgctgttt taatgagcac ctgggtacag gcaggctgaa   59460
gcctaaaatg gcatcagccc caagtgagga cagggcagag gttttatagt ctcttgtaaa   59520
caggaagtgt cctagtctga cgtaactgct atgttgtacc caggtggcct gtttctcgat   59580 cagggtaca tgtcttcgtc cagggtaggt gtcttcctgc cggctctctt cctgcttctg   59640
ctatcttgct gacacacgct gctgacacaa gtggacttgc gccttgggac tgggcctgag   59700
aagggaggag ttattcatct ccttaagctt tcaggccccg gggagaatct tataccgcgt   59760
agctaggatt acagacacat gccaccacac ccagctaatt tttaaagttt tgtagagat   59820 ggcatcacac tgtgttgccc aagctggtct caaactcctg gcctcaagta atcctcccac   59880
ctcagcctcc caaagtgctg ggattacagg catgagccac cacacctggc ctcatccatt   59940
atttaattta aggctttata tgctacgaag ctataggttt ttaatagaaa gtctgtttta   60000
catggttgta attatataat tttgcattct ttttccatac tataaaatat tttaatgtta   60060
taaattctgt acgtaatttt agtgaacatg ctataattta cataaaattc cttatcattg   60120
gacacctaac aatagagaat tgattgaata aatggtagtg cattcatata ataaaatat    60180 aatcagccat ttaaaaaggt ggattagaag tatacttctt aacatataaa catgttcacg   60240
attatgtata aaatgaaatg agtgtaccta aatatcaact acctctcaag tctgtctgga   60300
cattttccta cctcagtctc agcaactttc aaactttaat gagcctccca atcaccaaag   60360
gaacttgtta aatgccagtt tcacgcttta ccccaagagt ttgactgaga ctggggctca   60420
ggaattggca cttttacaag gatcccaggt gcctctgatg tgggaaagac acctcaccta   60480
tttctgcctg ttgaagctat acttaatttt ccaagcttct ccttcttctt tctcctgaag   60540
tcctgtagta ttttgtagca cttgtctgct ttcttgtctt agagatctta gcaaatgctt   60600
ctaaattgta aaactttcc tgatcctcca accaaaccta gttatgcacc catgtcacag   60660
ccccagaatt tgtgttaaac cctgtgtgag ttgctgaata taaatactga aatctctgga   60720
atccaaactt catttacttt gtggtggaga gagagtggct gagtacttca gaactcttta   60780
gaacacctgt tatagcagga acttttggga ataaaggtgg tctttctaac cttgatttaa   60840
aacaaaaaca aaaacaaaac cttgtttaga ttacttttac ttacctgaca gtcaggttgt   60900
gaaaagtaaa tagtttgtcc tttgtgcatt tgctctggtc taggccagag atagccagta   60960
agctggagag ggcagttaaa acccttcaag aggcctgtca ttccaaagaa tagttttctt   61020
caggtctgtt ggttggtttt cattctcaga ctgtgtcact gaggttgttc aaggtaagat   61080
```

```
tcttatcttg cagttcactt agggaccact tatgctaaaa ttgagactga gttactcatc   61140
aaagtacttc ttcacttaga tttttatcag tgtgatttcc ctccttcttt aaataatatt   61200
ggatatccat atcaagtcag gtttatgtca tcttacatta tcttttatgt aataggccag   61260
cttgcagatg catagttata aataactatt gataaatatt atattgagat gacactgaaa   61320
ttttgtcctt gcttgtaaga gaactagatc atattctgta taattagtta acacaaaaga   61380
attcctcaga aacaaacttt aaaagccagg tataacagct cactcatgaa aagttccttg   61440
tttcatatga aaatggtaac tttgtagaag taaagctcca gacaacaaag aattgacagg   61500
gttggggaat ggaaggttaa tgaaattggt taatcaaatg cttctgatgg ggaatcacca   61560
catgtagtgt acttgtccac atggcaaact cggaatcact cttcagaacc ttgtgtagag   61620
gcatcatcta taaaccctg catctgtaag gcttttcat cagccccctc cttggaaaaa     61680 atttctttt ttattctatg cccacaacag tacactacac acacatctat catatgtcac   61740
actctagtat atgcttgtgt gttactatta tccaatagat cagaaattca ttgggcatag   61800
agcatgtggc ttatttgtgc aatctgaccc aggttcagtg cctggatata gtagtattca   61860
ttaaatagat gtatgaataa gaattctgca ctgaacaggg tacataaatc atataaactg   61920
cattttgtgg gtgttttctg agaactcctg cagttaaatt taaagcatca ccttatgaca   61980
aatttccata aaatattgtt ataataaatt atgaataaat gttgaaaata acaagcccag   62040
tatctgctgt tccctgagtc cctgatggca actgcatgct ccccagtctg tgggactcct   62100
gatttaaaga gctagatctg aacttctgca gaaacctgct caacatttgc ccattggttg   62160
ctgtgaaatt cctctcctgg gctcttaaat tccacagagg cttaattatt acagatattt   62220
aaactttgta catacatgac ggatatcaaa catacccaca tctctaaggt aaactgtatt   62280
aaaagtgcca gacaatttta aaattgaaag ggacttcgtc atttttactg gttaggaaac   62340
caagcctctt aagagacaag cagttttgt tagtgggagg agcactagaa ttgaagtcaa    62400
atagaccaga gttcagttct tggctcaggg gctcaaatca cagcctctga tcggcagtgt   62460
gatcataagc cctttactta atattttga agatcagttt tttcatttgt aaagtttggt    62520
taataatccg tctcagtggg tcacaacaag ggattacttg agattacctg agccagagca   62580
gcacacataa tatctgcaca aagcaaatcc tcagtgagct tttgtctctg cccttcttg    62640 cccagatcac acagagctaa gacttagacg cttctttgg gttgtggttc ccagttcacc    62700
tgacaggact cacacatatc aaggatgctc ccaaggggct gtgtcacatc agcatttaaa   62760
tacagaattc aggatctcct gctttaaaaa caatctccct tctgagttac tcttttaaa    62820 ttttatttat ttatttattt attttgaga cggagtctcg ctctgtcgcc agggctggaa    62880
tgcagtggcg cgatcttggc tcactgcaag ctccgcctcc ggggttcaca ccattctcct   62940
gcctcagcct cccgagtagc tgggactaca ggcgcccgcc accacgcccg gctaattttt   63000
tgtatattta gtagagacgg gatttcactg tgttagccag gatggtctcg atctcctgac   63060
ctcgtgatct gcccgcctcg gcctcctaga gtgctgggat tacaggcgtg agccaccgtg   63120
cctggccctg agttactttt attgctgttg tttttttttc tttccttgta ctgcgagtta   63180
tgacaccctc ccagtcaacc atcaactata atttaacttt atataattgt gtgaattagc   63240
aagatcctag gaggctccag gatctcaaag gctccaggat ctcagggtaa tgtatataca   63300 catttagaa gagtaagatc tacatcgcct aataagtctt cagcttttaa aaatcacatt    63360
ctaaaataat aagtgaaata tttgtgctga attgaaaggg tttccataaa ttctgacggt   63420
aaacgatgag tgttttaagc atggagatgt tagtcataca aacttaagtc accatgaaac   63480
```

```
aggcgatcaa gtgggggaag cagcatcctg tttcctagtc ttaccagagt tcatttgtca   63540
ttttaagaga caacttactt ttccatcttt tcttcttttc ctgtaaaggt agaaacctgt   63600
gggttcttgt tgtggggcgg tttccaaagg aacacagaat tgggattcca gagttcaaat   63660
acgtggcaaa tatgcatgga gatgaggtac gtatgtggct tgaatttctg aaatgtcacc   63720
agagaagctt cccctagggt ctcttgagct ctgtataaat gctaccgagg aagcctggag   63780
aagtctccag catgcattgt acaaagaagc aaggcccaga gaggtcttcc tgtgaggcct   63840
gtgggaggtt aaggaatcag ggtccaacaa ccaccacagc tgtatggttg tgtacccagc   63900
accctgtcag agtagctgga gcttgttttg tgtttggggc cggaagaaca acagttcccc   63960
agccctgaac ttctgccagc caatccctgc atctcctttc tgggttaagt tttcccacct   64020
cctggtcagc atgaaggtga cccagcaaag gagctgtatt gtatccgaac ccacaaccat   64080
cagaaactcc caaatagcta cccaaattcc tgagatctgg cttttcaaat gcttttgtta   64140
ctctctctta aatctaacac tcattgtctt cagtgctcca gtttagacaa tcacacttat   64200
gattctctcc tactcaccat tcaacaaaca cttggctggg tgcagtggct cacacctata   64260
atcccagcaa tttgggaggc caaggcaggt agatcacttg aggtcagtag ttcaagacca   64320
gcctggccaa catggtgaaa ccttgtctct actaaaaatg caaaaaatta gccaggtgtg   64380
gtggcgcata cctgtaatct cagctagtcg ggaggctgag gcaggagaat tgcttgaacc   64440
caggaggtgg aggctgcagt gagccaagat cgtgccactg ctctccagcc taggcgacac   64500
agtgagactc catctaaaaa aacaaaacaa aacacaattt taaattcctt aataatatct   64560
tgcctctttt ccaacttagc agggataaac tctccttta tttttaggtt ctacaaaata   64620
ccatttacca ctgttaccta cccagccatt cttgccaggc agttgaagat gttcacctct   64680
gtttctcacc ttgcttcctc agaatatttt gagaccatga caactgaaat attttctgtt   64740
taccaggact ctataaaact gagcgatcaa agagtcccca gccatcccag taaggaaact   64800
ttgcacagga atgtgggtat taccctgtaa acacaactt ataactttag ggactttctc   64860
atttacatac atattccaat aagtactacc tgctgacttg ttaaaacact tctggatttg   64920
caatagtatg ggtggcatgc tctaatcagt gctgagcttc ctgttctggc ttaagccctc   64980
cccaaactct ataggaactg gatctaccct tcatggtaca ctccgcctgc ccttgccagg   65040
catgctgccc aacctgtcct gctgagagag gatacttctt gcagctgcag ctaagatgca   65100
agcacctgcc cctagcaaag gaataagttt ttgaacccga ttttggggtg ggtgcaagtt   65160
tagcccatct gtgactttt gagcatcacg ggcggcttct ttaaaaaga ctacgttgca   65220 aggagtctga ccaaagttag ttttaataaa acaactgttc gttatagaca gcagctcaga   65280
ctgcgtttcc cttttgctat cttgtctatt gatcgaggtc ccttgatcaa ggtccctcag   65340
aatgcttttt tttttttttt tttttttccg atggaatttc gctcttgtct cccaggctgg   65400
agtgcaatgg catgatctcg gctcactgca acctccgcct acaaggttca agcaattctc   65460
ctgcctccgc ctcctgagta gttgggacta caggcatgca ccactatgcc cagctaattt   65520
ttttttgtat tttttttttt tttagtagaa gatgggggtt tcaccatttt ggccaagctg   65580
gtctcgaacc cctgacctca ggtgatccgc ccgcctcagc ctcccaaagt gctgggatta   65640
caggtgtgag ccaccgcgcc tgactcagaa tgcatttgta acaagagaca tatggcattc   65700 attgtctta gtagttttt tattgctggc atttcagagg ttccagctat ctactcagaa   65760
attagtcctc agaactgaaa ctcccaaaga taagcaagag tcctttccgt cccctacccc   65820
cgaatttgtt tattctttcc atgcactttc ctaaatttct ggcatcttgt tgtctggtgt   65880
```

```
atcgttcaaa tcagggctcg ctagtgcgct ctgattcttt gagaaatgct gagggctgag   65940
actaggcagc ggggaaaagt cccagtgtat tttggggtgg gaatctgaag cacttttacc   66000
cccttatgtg acccagctcg tggcaatgtc tgggggctct atggggctag taagaaattt   66060
attattctga atttgagacc ttatctattc tgtcctcccc atgccgctag gagctgaaga   66120
aagtgatggc ttaacattgg agcagagaag tccttctgaa tacaggatat aacaaccccc   66180 ttttcctcc catagatctt ttgaaattga aagcatttt aagaagcaac agagctaaca    66240
ttttagggca gtgattctta acctttttg gtgtattcct tgctattctg ttataaattt    66300
gacctgactt cagggtctgt ggattaccta ggagtttatg gaccttaggt ggagaatccc   66360
agcagggaac acatacacac tgagtggcag ggtggacaga attggccaca ctattttaa    66420 aatgggaccc cacccccact gtgcgtgtgt gtgtgtttgt gtgtgtgttt ccacacttaa   66480
tactatggct agatgacagg aagcatcagc tgcatcaggg agactcagct ctgctgatta   66540
cacctgccat tttcccccat gtattttat tttacttatt tatgccttgt tttagaattg    66600 ggtcttttt taaattagaa attgtctggt ggccaaaag catatgaaaa agtgtctaac     66660
aacactaatg atcagagaaa tgcaaatcaa aaaccacaat gagatatcat ctcataccag   66720
tcagaatggc tattaataaa aagtcaaaaa ataacagatg ctgatgaggc tgcagagaaa   66780
aaggatcact tacacactgc tggtgagaat gtaaattagt tcatccactg tggaaagcag   66840
tgtggtgatt tctcaaagaa cttgaaacag aactacgatt caacccagca atcccaatat   66900
atacccaaag gaatataaat tggtctgcca taaagacaca ttcacacgta tgttcattgc   66960
agcgctattc acaatagcaa agacataggg ttagtctaga tgcccaccaa tggtagactg   67020
ggtaaagaaa acatggtaca tatacatcgt ggaatactat gcagccatga aaaagaaca    67080 agatcatgca cttgcttata gaacaagatc tataagcaaa ctaaacagaa aatcaaaaac   67140
cacatgttct cacttataag tgggaactaa acattggata cacatgggca caagaaggg    67200 aacaatagct accagcatct acttgaggat ggagggtggg aggatggtga ggataaaaac   67260
ctacctgtta gatactatgc ttattaactg ggtgatgaaa taatccatac accaaatccc   67320
cacaacacac aatttaccta tagaaccaat ctgcacttgt accccctgcac ttgtaacatt   67380 tacctataga accaatctgc acttgtaaca tttatttta aataaatgt taaaaaaaa     67440 aaaaaaaaa aaagcaggcc gggcgtggtg gctcacgcct gtaatcccag cattttggga   67500
ggctgaggtg ggtggatcac ctgagtttag gagttcaaga ccagcctggc caacatggtg   67560
aaaccccatc tctactaaaa atacaaaaaa ttagctgggt gcagttgtgg gtgcctgtaa   67620
tcccagctac ttggtaggct aaggcaggag aatcacttga acccagaagg cagaggttgc   67680
agtgagccaa gatcatgcca ctgcactcca gcctgggcga cagagtgaga ctgtctcaaa   67740 aaaaaaaaa gaaaaaaaaa ttattacaaa atcaacatat gttcatgtta gaaaaagtat   67800
aaacaaaaca ttatatactg accttcccaa aattagtgct cttaatttct tatttgtttt   67860
tccagatatt tgtgtgtgca tgtactttta ccaaaagaga tatgctattt gcaacacttt   67920
taagtaaata ctagctacct ttttgtacca ataaatcttt atcctatctt tatcttatcc   67980
cccactttct agtttctcca attgtcctca aatgtctcta aaattaccca atcaggatc    68040 cagtcctggc tcatgcatcg catttagtgg atatgttgga tctcttggat ctcatttaat   68100
ccagtatctt tttattatga tactaggctt gataaagagc ccaatcagtt gtctgccctg   68160
tagaatgcca catattctgg attttggtt tgcttcttta tagtatcact gcagttgtac    68220
ctctagtccc tgactttact tcaaactgga aattaaatct aaaggtttgt tgaatttaat   68280
```

```
gtggctaata cacatcttag gagttgtgac gataggttca tttgattgat gctgagggtt    68340
caggctaatt cacctggcta cactcaggaa tgccaaaagc aaactccggg tagcaaaatc    68400
aacttaaaat ggcccatttt cagccaagta ttgttacaaa ataagtaaag ttaaactcac    68460
tcctcatttt gcatgaattt cacgtattct cttattcttg caaggtcat tgttctacta     68520 ggatcatggc tcatactgta gatatttttc ttgtcttcag tgaccttcca ttgtctcaca    68580
tgctttctat ggcacaggct cactatgcca cattaatcag gctggcaagt tgcctcctca    68640
aacagtgctt tacaagaaaa taataacaat agctaacatt tatggagcac agatgacaat    68700
aagtgcattt taggcctcgt ttctttggat cacctctgca gaaggcatgt ttattagtcc    68760
catgtaccat gaagggggcc caggtttatg cttggtcacc agctgtggga acccggagcc    68820
tgaacaccaa gctttgccca gctgtggatc cactcctttta ctctctcttc tctgttttta   68880
aaatgttctg ttttatggtt ttcattctta agtatagatc tatgatctat ctcaaattaa    68940
tttcactggg atggatacta agttgttgca gcaccatttg gtgagaggat ttgggcttgc    69000
tgttatgtaa aagagtaaca agctcttgga gggcaacact ggaataagta tcttccagtc    69060
acctacctgt ccctttcttt cccctactct tcacttctct ctccttgact gctggggagc    69120
tgacagacat agcactcgtg gtgagccttt gtcaccgatg tttattcatt ttttggagca    69180
gcatgggaga aacatttctg gggttctttc tcattttaat aagactagta ggtgttttc     69240 tggttcatcc aggcacacac attatttgca cacatattgg catgttggat tgaagcctca    69300
attctaggtt taatttacgc aagctcctaa ttggcatcac ttggcatacc tacagttgaa    69360
tctttttttt ttaattggaa gggttgatgc cagtgcaggc tgaatggggt tctctgccat    69420
tcctgtatgc tacagatatt cagattgcct gggaacagga tccttgtccc ctcaccttcc    69480
cccatcacct cattctgctc ctggcttggt gtgtagtaaa ctataaccaa tactctaaaa    69540
tcagagctat actgaaaact gggaccatgc cctgaaacca ggagcatcta acatcctcag    69600
cctaaatgtg gatgcagaag agaagcctgg gaaaatcttc cccagccctc cctactcttt    69660
gttttgtgct tatcttctat cccatgtttt tcaaattttg cagaaaaaat actttcttg     69720 ggtaatctct aggttggtaa gacatcttta attcctgcct aatggaaata ttgaagcaag    69780
gcatgactgt gtgcttaaag aattgggtgc ccaggccagg catggtggct catacttata    69840
atcccatcac tttgggaggt caagctgggg agattgcttg aggccaggag ttcaagacta    69900
gcctgagaaa catagtaaga ccttgtctct aaaaaaaaat ttaaaaatta gctaggtggg    69960
gtggtgcata cctgtggtcc cagctactca ggaggctgag gtgaaggat tgcttgagcc     70020 tgggaggtcg aggctgcagt gagccatgat cacaccactg tacttcagcc tgggtgacaa    70080
agcaagaccc tgtcttaaaa aaagaattga atgcctagag ttttaagcca accctagtaa    70140
cattaagcaa agtatcatag gtcagagcct gggttcaaac ccaggtttcc ttgacctcag    70200
tgccaagggt cttaaatact gtactgtagg agtaactatt gaatatgctt gtaaataat     70260 ttaactaaat tgcaattatt ttttatttta gagttgggat ctcgctctgt aacgcaggct    70320
agaatgcatt ggtgtgatca tggctcactg taacctcaaa cacctgggtc caagcaatcc    70380
tcctgcctca gctcccaca tagctaggtc tagaggtgtg tgccaccaca ccaggctaag     70440
ttttttattt tttgtagaga tggggtccca cagtgttgct cagactgttc tcaaactcct    70500
ggcctcaagc gatcctctgg ctttggcctt ccaaagtgtt gggattacag gcttgagcca    70560
ttgcgcccag cctaaattgc aattctgctt ttttggggag atggggggta ggaatttttt    70620
taagccttag tttcttaaag agcaatgaag tatttttact aagatagact taatatgggc    70680
```

```
ttttgtaact gcccaacagg ttcattttgc ctgttgtcca gatagagcag atttatcaag    70740 acagggaat tgcgatagag aaagagttta attcatgcaa agccaactaa acaggagacc    70800
ggagttttac tattactcaa gtcagtctcc ccaaaaattc agagactggg agtttttaag    70860
gataattttg tgggttgggg gagagacagt ggggagtggt gattggtcag gtcggagacg    70920
aaatcatagg gtgtcaaagc tgtcctcttg tgctgagtca gttcctgggt gggggccaca    70980
agaccagatg agccagttta tcgatgtggg tggtgccagc agatccatcc agtgcagggt    71040
ctaaaaaata tcttaggttt tacaatagtg atattatccc tctgagcaat tggggaggct    71100
tggaatcttg tggcctctgg ctgcataact cctaagccat aatttctaat cttgtggcta    71160
atttgttagt cctacattca ggaaaaggct attatcatct ttgtttcaaa gttaaactat    71220
gaactatgtt agtttagcct atgcccagga atgaacaagg acagcttgaa ggttagacgc    71280
aagatggagt tggtttcatc agatctcttt cattgccata atttctcac tgttatgatt    71340 tttgcaaagg cagtttcact tttgaaaaat tcgcatcaca tttagaattt tatgattgtg    71400
gcattggttt atagtttatt gtattccaga aatataggtt gaaaagagaa aacattccct    71460
gggtaatagt ggccatattt gtcaacctga aaataaagag ataaaggata aatgactttc    71520
acacaccttc taagtataag agacagttga tgagatgtag tttgcatgtc taaatgtttt    71580
acttaggggg tattttaatg gtttacgcag acagtgggac acaatatctg aaattatggc    71640
cgttctggaa aatctgggaa gtacagtcaa catgcagtag aggttcccaa cttatcatta    71700
aaccaaaaca caacattaaa gcttgtcttt ctaaatgccg ctgcccaagc tcctttttcct   71760 accactatcc tcaggtgata gtaaaatgtc ctcagtaacg ctctgtggtt tgaataatta    71820
aattcttcct ttttagattt aggcagagct cattgttttc caggtgaaat atctaattca    71880
ttttaagcat gttttaaatt aatgaactgt ttggtgacca gatatcccaa gtccctgtca    71940
tgagcgtaat tgttagcctg tgcctctata aaatgtgttc ggtatttaaa aatccttcag    72000
ataaaatagc ttgatcattt gtacatctcc ccttacaaag caccttaagt cctcatgtga    72060
atttcagaaa gttcttcctc aggatagtct tgatcttata atgaattttc aacagtagtt    72120
tattagcaat tatttattga atacatgata taccaggagc tggacaagct acaccaagaa    72180
cacagggata cagagaaaaa ccgtgaaggt ccctgacttc ggggcttcga tggtggagtt    72240
agagaaaggg aggtcagtca aggtcagcca agtgattgta acgtgtgtga cccgcattag    72300
ataacacagg tgtcatggtg aacccagact tgggaggtca agaaaagtat gctagataaa    72360
tgtcatgttt aggctgatat ttgaagaaga aggattagct aggcaggtca gacaaataac    72420
ttaaatctat aacacacaca ccactgtgga gccccacagc ccgatgactt tcccccccaga   72480 agctgcatca cagggtagca tttcaaaaac agattccatt gttaggatag ctgaagattc    72540
tctctctctc tctctctcac acacacacac acacacacac acgcatgc gcgtgcacac      72600 acacacacac cacacaacac tgcctgggtt gtagattgtt ccttcaaaaa ttttttttctg   72660 ttttttttaa taaacattct gtgaagaacc agaacactca tttgtatctg tgtggcaaat    72720
tccaacttga ctgaattgaa ctgcagctga tagagaatgt attttctgct ttctgggtga    72780
ctgccatttt aaccaccgga tgaaggagat ggagtgagag tctccggagg ccggtgtgtc    72840
catcaggccc ccgtttcttc atgagggctt ctccctgaag tctgtgctct cacaggaagg    72900
aagccagcat gctgggtgaa aggctgcctg ggcaattgga gactcttttg accacattct    72960
tttttaaaat ttggactctc cagggtttcc tgtcaaagac ttaattttca atgaaggag     73020 gtttatacat aaaacatgaa tgagtgtttg aaacatttat attaaggttg ggaagaatta    73080
```

```
atttgaataa tatttggcat aaatctgctg ttacagaggc aggaaaagat ggcccaaaaa    73140
gaaaggagga ttttgtttaa ctgcctctga aatttcatct gtttatctca gcatttaaaa    73200
aattatctga tgcttagttg gttctttatc ttattttcaa gattttatt tacccttgca    73260 attgagaact tgtgatttgt tgtggactat tgagacacac aaaaaatact ttggttacat    73320 acttgttttcc ctgaaagaat catgattta ttattttttgt aaaaatgaca taggttttct    73380
ttaaaaagaa taagaggaaa taaaaatcat tcagaatact gtacccagaa atagccatca    73440
ttaatatttg tcagacatca ttgtagacat ctatatattt ctgtagtaag agaatgagag    73500
gaattaaaag aatataaaat aaaatgtctc atatgttata ttgtatgaaa ttttatttta    73560
tttgaattaa cagaagaata aaactgaagt gaaactaaaa taactggtga aattgatgct    73620
ttctcaaaat aagaaattga ttatcacatt tgtctttctt tttttttttt ttttgagaca    73680
gagtctcgct gttgcccagg ctagagtgca gtggtataat ctcggctcac tgcaacctcc    73740
aactcccagg ttcaagcgat tctcctgcct cagcctcccg agtagctggg attacaggca    73800
cctgccacta cacctggcta attttatgt ttttagtaga cagggtttt caccatgctg    73860 gccaggctcg tctcgaactc cctacctcag gcgatctgcc tgcctcagcc ttccaaagtg    73920
ctgggattat aggaatgagc caccgcgccc agcttgatga tcagattttt ctaaagttaa    73980 gaaaaagat tattaaaaac tttgaaattg tagtcatttt atgtgtatat attttaactt    74040
ttgatagtat tttatgtccc cttactatga aatgtgaagt aattaacact ttgaaaattt    74100
ctccctcaac ttctttttttt tttgaggtgg agtcctgctc tgttgcctag gctggatgga    74160
gtgcaatggc acaatctcgg ctcactgcaa cctctgcttc ccaggttcaa gcgattctcc    74220
tgcctcagcc tcccgagtag ctgggactac aggtgcccac caccatgccc ggctaattttt    74280 tgtatttta gtagagacga ggttttacca tgttgcccag gctggtctcc aactcctgac    74340
ctcaggtgat ctgcccacct cagcctccca aagtgcttgg attacaggca tgagccaccg    74400
tgcccggcct caacttttat attttgttct atacccatac taccaagact gcttaatcta    74460
attctgtatc taacagaata ccaactcaac ctagcctcct aatcatggtt tctttactct    74520
tccttttcac tttctttcgg ttgggtgaat ttcattgcca actcgtgtcg tgattgtttg    74580
catgctggag agtgtatgat tcagatagct aagagacaaa ttcacattta gagtcacatg    74640
gggattctga tatcacttcc tctctgttct tgacttggga ctcagatagg ccagggattt    74700
ttgccgattg aaccatacta tggcctctaa ccagcattta gacatttaag gaactatggg    74760
actcctggtc acttcctcct caccttcctg tacctattcc tccccaaacc cttctgagaa    74820
agcttcttaa accaacgatc tttttcacat tttttttggtt tttttttcgag atggtgtgtc    74880 tcactctgtc acccaagctg gtggcgcgat ctcggctcat tgcaacctcc gcctcctagg    74940
ttcaagcgat tcttgtgcct gagcctcctg agtagtgggg attacagtca cctgccacca    75000
tgcccagcta attttttgtat ttttagtaga gatgggtttt caccatgttg gccaggctgg    75060
tctcaaactc ctgacttcgg gtgatccacc cacctcggcc tcccaaagtg ctgggattac    75120
aggcttaagc ctcacgcccc agccccttttt cacatttaaa gttactgtca cagttttatg    75180
ttaccagctc ctccccactg gctttagggg aggtcataag tagctcatca aggttacttc    75240
caaaggtgct ggaccttcaa aaacctatta tatcttaaaa ttgaaccca gtggggtgta    75300 caagtgactt ttttggttat tagcttgtaa ggacttttc cagtgacaat tttgactata    75360 aaacaaaaa tctggccggg cgcggtggct cacacagtaa tcccggcact tgggaggct    75420 gaggcaggca gatcacctga ggtcaggagt tcgagaccag cctggccaac atggtgaaac    75480
```

```
cctgtctcta ctaaaaatat caaaattagc cagacatgct ggtgggcacc tgtaatctca   75540
gctacttggg agggtgaggc aggagaattg cttgaatcca ggagacggag gttgtagtga   75600
gccaacatgg tgccactgca ctctagccct gggtgacaga gtgagactct gtctcaaaaa   75660
aaaggtagtg gaagaggaag ataaaaaatg agtaggaaaa aaagttgaag tcaggattgg   75720
acataatctg actctaaatt ttatggttgc ctatgaatct ataattcata tatcccaaat   75780
tttctttctt tcttttttt ttttttttt gagacagggt ctcactctgt cacccatgct   75840
ggaatgcagt ggtgcgatct cttctcactg ctgcctcaac ctcctgggca gcacaagcga   75900
tcctcctacc tcagcctcct gagtagttgg ggccataggt ctgtgtcacc atgcctggct   75960
aatttcttat tttatgtagt gatgggatct cgctatattg cccaggctgg tctcaaactc   76020
ctgggctccg ccttagcctc ccaaagtgct gagattacag gcatgagcca ctgccaccag   76080
ccccaaattt tcttagtccc aatttcaatt attctgtgtt cattaggata acaaatgttt   76140
aaaatgtggt ctctttatgt gccagtgagg gaatcaagtg agaagtggtc atccaaggac   76200
cgcttatcct ttgtcacaat gttgaagtcc tacagtgaaa tcatgactgg aaattcttct   76260
gaggctccat gaaatctttt cttgcacagt gtctacatga atgtgcctgc agcactctcc   76320 tgatttctc acctgctgcc cctgagttct catttactaa cccctcaaca acatctgttc   76380
ttctgaagca gattccttga acctaaaatg ataggagaa tttgatgtag tctaagcaga   76440
tcttcctatg ataaggctga catttaaatt acttttttta aataagaaaa ataatgactc   76500
tctctcctgg ggagggatta taaagcaagt tctctcacag gccttcagtt tcccaagcct   76560
tattgatact gcaagctaat ttaggtggat atgacagctt ttaacatttt aatagtcatg   76620
cttttactta atatatatta gaaatatata tctagaaaag tgataatgat atgaagtttc   76680
tcaggagttg gaagccagcc ttagcaacat agcaagaccc tgtcttaaaa aaaaaaaat   76740 ctacaatgtg atgattttaa gtctgttatc caccaataca tacatgataa gcttcatatg   76800
caccatgcat tctcatggaa atacgtgatt cctgtgcttc tctgtaactc aacctcttgc   76860
tctcccactc cagaagatac tttggaaggc aaccaaatga aaaatgttgt aagaatcatt   76920
attgcggccg ggcgcagtgt ctcatgcctg taatcccagc actttgggtg tctgaggcag   76980
gtggatcact tgaggttagg agttcaagac cagcctggcc aacatagtga aaccccatct   77040
ctactaaaaa tacaagaatt agctgggcgt ggtggcacac gcctgtaatc ccagctactc   77100
aggaagctga ggcaagagaa tcgcttgaac ccaggaggcg gaggttgcaa tgagccaaga   77160
tcgcgccaat gcactccagc ctgggtgacg gagttgagac tgtctcaaaa aaaaaaaaa   77220 aaaaaggaag cagcagcagc agcagcatta ttccactcta attcattttt gcaatatgta   77280
aactatttac aaataggtac tttcactctt actagcattt ttcagcatac ctcaggactg   77340
atcgccacct gatggccact tggcagagca taagcatgct tgagaaagag tgatcttaca   77400
aactagtttg ggtctgagat atcatgtgta gagacccta ttggggaatt tgtaccgtag   77460
ggagtgcttt ccttattgcc tctgacctaa taatgtcctc ttttctcttt aacacatata   77520
gactgttggg cgggagctgc tgctccatct gattgactat ctcgtaacca gtgatggcaa   77580
agaccctgaa atcacaaatc tgatcaatag taccccggata cacatcatgc cttccatgaa   77640
cccagatgga tttgaagccg tcaaaaagcc tgactgttat tacagcatcg gaaggtaaag   77700 agggggctggt ctatctttac ttgaaaacaa cacaacacaa aggctcccga caggcacctg   77760 ttggcccttgg caagaggaga tgtgtcatgg tgagagccct cagagccggt gtcatgtcgc   77820
tgatgtgcca aagctcaagg cacatcaggg ctgcctccgg cttgcaggaa gaaatgcaaa   77880
```

```
taaggctact tgccccggt gcccacctag cctctccatc ttcatttgcc actccttctc   77940
tctcccctgc ctcctcccct ctaggcctcc ttcctggaag taccaggtgc tttcttacct   78000
cagcatttta cacacaccgt ttccctgcct aaatagcatt tcctccaaga ctctttctct   78060
cgacctgtca tacactagat cccctgataa actctcacat cacctggcac tttactgtca   78120
gagcacaact tttaatatct aatttcttgc ttcatgtctc tccccccact acactgcaag   78180
ctacctgcag gcaggaatcc tgtccattgt gtttgtcgtt gttagatccg cagtgcctgg   78240
cagagcaccc aggcccttgg taatgaccgg ttgatttatt aggccagtag tccaagaact   78300
aaccataagc aagaacgggt cttgaaggag ctctgattta aacagtttat tttgtttcaa   78360
gctgccttgg gaggtttgga atttctcaga tgtctaatat acattcatat gtatgcaatt   78420
tacatatatg tgtttgcttt accaaagctg aacaaaatct caccacttga ttccctccaa   78480
ttttaagttt ttcaaatata tttaaacatg gctgttccac gtttcacaag tacttctgtg   78540
taatgtgttt agtgttgttt ctgttatcag ttgctactta acgaaccacc ccaaaattag   78600
cgacttaaag caacagcctt tttatttact gttgattcca taggtcagga atttgggcag   78660
ggcagagcag ggatggctac tgtccgtgcc acaggtctgg ggctcagctc tggtcttttct  78720 gagacaattt acctggagcc atggactctc cgtggactct ccacgtggcg accattggga   78780
tctcaaggtc ccaaaaggga gcatctaaga gcagaagtcc caaatacaaa cacttatcaa   78840
acctctgcct gcatcacaat agctagtatc tcattggtga gagcagatca cgaggcaggg   78900
gatgccatgg gatgtaagtg ccaggtgtgg gtcatggcag gccacaaggg cagccatcca   78960
ccacacccat actcacgttt ggaaagacac ctggagccta aaccaaaggg caagacactg   79020
taagaatcca ctccctcatg ccctatcaat aagccctaaa atattctttc ttttaaaggg   79080
aaaattataa ccagtatgac ttgaatcgaa atttccccga tgcttttgaa tataataatg   79140
tctcaaggca gcctgaaact gtggcagtca tgaagtggct gaaaacagag acgtttgtcc   79200
tctctgcaaa cctccatggt ggtgccctcg tggccagtta cccatttgat aatggtgttc   79260
aaggtaagca ggtgcgggtc cagttctggc ttcttaagtc cagagtgggg ctgaaaactc   79320
tctgcctctg gatggggatc agctctccct tcccctctta acttctctgg cagggtgaaa   79380
agagcttcat gttcccaact ctagccatcc ttcctgtgat tcttcaacag cagatgggca   79440
gtgtggctga actgacaacc cacagctgga catgcatcag tgaattagtg aaatttagat   79500
tctagaaaat acaatctaaa tagtcagatt ttgattctct gacaagagac aacatggcta   79560
aaataacata aaactggaac aactcacttt tttttttgct aatcatatat gaacaataat   79620
tgttgactct tcttaaaact ctgtgggatg aggacccaaa atattacagt agctttattc   79680
acccctataa tacctaaaga aattgtcctt acctccagaa attagcaaga gtgactgaga   79740
ggacacttaa ttttttaagct gatttaggag tttggatttg tatctgactt atttgggggc  79800
tatcaccttg catatgttta ttataaagta gaaagaagaa tagaggaggt ggatgaagga   79860
tttctctcta gggaaattag agcatgtgtg tgtgatgcga ttatgtcttt gctaatatgg   79920
tgtttgtgtt tcctcttact ctcaagtcag tttaaaggtc ttggttcatc ttttaaatgc   79980
agcaactggg gcattatact cccgaagctt aacgcctgat gatgatgttt ttcaatatct   80040
tgcacatacc tatgcttcaa gaaatcccaa catgaagaaa ggagacgagt gtaaaaacaa   80100
aatgaacttt cctaatggtg ttacaaatgg atactcttgg tatccactcc aaggtgagtt   80160
tctcttcatt tcttccattc tccttattgc cttcacccag aagtgccagc tggtttattt   80220
tgatccagca gttgttaaaa gaactttagg cacaataggc ccttcactct gtccttatca   80280
```

```
gctaatatca taagagcagt ggagatgact gattgtttga gagatgctca gacatgttcc    80340
tcattaccaa gggccttctt cattcattca ggtacttatt ctgtgtctgc ctactgtgag    80400
ccaggaactg aaagatgaac aagacacaca cctcaccctg gagttgaata ggggagacag    80460
acacgcagat aagtaattgt gatagcagtg caattagaat aaaaacagat ttagagaagg    80520
tgcagtgtac cccaagggtg cacagagcca aaatacaata gggagtagtg aagagcttgg    80580
agaaatgtga tgcttacatc ccatctaaca gggacagctg ctactagatc tagctaatta    80640
ttgtcatgca gccttgggga gccaatactg ccagatcttg cagtttgtaa agagaagctg    80700
aatttgtaca tgaagtatca tgattttaaa gccattttgc gggctcaaca aaagagctct    80760
tcagacagga tacagtggga ggagggcccc cagttctcca atcttggaat aagacagccg    80820
ggtaagggac aggatgagat tgtcatgtag gcaacatgga aggagagata ttcttattag    80880
agggaataat ataaacagaa acccggggta ggagggacct agggtggaag gacaggagga    80940
gagacggact ggaactggat ttccatgcct caggggaaaa cattcccttt tagactcgtt    81000
agcctgaccc caccaacagc aagttgcggc atgcatttct gcgtgcaggc cacttccaaa    81060
ggtgccttcc ctaattgtca ctttggatgc acaggctttc aggtaatctt tcacaagctg    81120
gtatttttat gcctgggtgg ctctctgtca gttttcctgg taatataaat aagcatagac    81180
cacaactgat aggcaacagg tccaggcagc attccaaacc tctctctggt gtccaagata    81240 cagcccctc tcctacctta gggcttctgc atcgtccctg ctctccacaa tttgtagcta    81300
agaaagggcc catcctgtcc agtggcagag ctgtccttca tgttcactgt ctaactttcg    81360
aaggcaaatc cagatgtgta ggaaattagc tagaaacggt tgctgctggg aattgttccc    81420
cagtgtgcct gtgtgtgagc tgtgtatcct tctcagacaa aaaacaggtg aagccagctg    81480
ccttgaggag cccagaagaa tgtgcctggc ctggcctgga tgttttgttg gccaggcctg    81540
acccgcctta tccagaactg cccctccac gcttggcatt tcagttctg ctatctgct     81600 agggatccat aatgcctgcc tgttttgcta tttaaaacaa acccttttgaa agtaagggac    81660 cagaggagag aactgaaaag tcagcatgag cagtggcagc ctgggctcca caggggccg    81720 ggccgttcac ctctgagagg cagtgcagca ctctttcttt gatccccagg agcactctgg    81780
catattgggg aagcccacag gtgctggcgg aaggtggcct gcactccagt gtctgtcatt    81840
tactggccaa aaccctgag cacttttctt taacatctgt gatcatgttt cctcatctgt    81900
aaagtagggg caattgctgt gaggattaaa tgagctgata caaagcactt catatggtac    81960
ctggcaatag tgaatgttgg cccatgattc ccccaaatta gcatgcttag ctttgcttag    82020
taagtgtatt tataaatgat ttgtagaaat attttaaagg aatcttattc tagcttatat    82080
ccatgtaaaa tgtaatttaa gaaagaaatg aaattcaaag aatcattttt gtaatgtagg    82140
atttcaaaaa ataaaaacaa aaaaggaccc ttccttcacc cgtcacttaa ttttgatgca    82200
cagttgaact tcagtcagct ctgatccagt tacccatatg gaatattta ggattgtcta    82260 gtcacgcctg ggtaatagaa tgtcaagccc tgattttaca agctaatatg tcaaattcat    82320 ttttttcctgt ttacatgtag ctgtctgatt catttgtccc cgaggcacgt gatacttggc    82380
tccactccaa ttttagaccc taacaaaaat taaatatgct tgtgtttagg tggaatgcaa    82440
gattacaact acatctgggc ccagtgtttt gaaattacgt tggagctgtc atgctgtaaa    82500
tatcctcgtg aggagaagct tccatccttt tggaataata acaaagcctc attaattgaa    82560
tatataaagc aggtgcacct aggtttgtaa aattttctta ttaattccct attaatacaa    82620
aatagagcat ctggcaagac ctctgggttg actaaacgca agcctttatt tatgctttgt    82680
```

```
agttatagcc tcatttcagt gccagatctg atggttaaga attctctctg catgagtatc    82740
tgcagtgtgt gagaaatgca gtgcccactc attcatagaa aaggaagcat gatgcatgtt    82800
cctttaatat gagggtataa aaatccagag taccaggtgg tcgtggtggc tcatgcctgt    82860
aatcccagca ctttgggagg ccgaggcagg tgtatcacct gaggtcagga gttcgagacc    82920
agcctggcca acaaggcgaa acctcatctc tactgaaaat acaaaaatta gccaggcgtg    82980
gtggcacacg cctgtagtcc cagttacttg ggaggctgag gcaggagaat cacttgaacc    83040
cgggaggcag aagttgctcc ctccgccaag gagccaagat ggtgccaatg tactccagac    83100
tgggtgacag agtaagactc catctcaaaa acaaacaaac aaacaaacaa acatccagag    83160 tcccctaat tttacatgtt gaatgatcta gaaatctggc aaaatatcag gaaaataggc    83220
tgctactctg ttacatcatc tcccatttag aaaaatacta tgtttgcttg tcactcacca    83280
cgcagtacca aggaccctga gaacactgga cataccactt tgcatttttt ccagaattgg    83340
ggtggtgagc tagcaccatt accttcaacc cctctcacct ccgaactctg ccagatgtcc    83400
tggtgctaga atcttgcca gcctgtttgc tgaaggctgg ctggccctta tcacagatag    83460
acagactaaa tgtggcagag agtgatagct ttcaaacgtg cagtggactc accgggagcg    83520
cttgctaaaa cagattgcca ggccccaacc cggagtttct gtttggacca ccttaccacg    83580
tgatgctgat gctgctggtc cagcggctat acttagaaag ccattgcact agagaaacac    83640
actgctagag atgatgatgg aatcttgtac agttcaagtt tattaaccag gtggtgtctc    83700
tttgggcaag gtgtggaagg ctcttctata tttacagagg tgaagttatc tttctccatt    83760
cagaatggct tggggagaga aacatatcag gaattggcat aatagctatg ataccacatg    83820
gagagagaga gagagagagt gtgagtgtgt gtgtgtgtgg gtgtgtgtgg gtgttgaaaa    83880
ggtttgctgc atgggcctac tgcataactg cataattccc ggaattttct gcatgattca    83940
cagcaaagct ttcctcctgc tacaaagaag atggagaagg atgagggaag gtagcacagg    84000
gccagagggc tgagtgcaag gatgattagg acccttcctc ggcacacatc cctaaaggg     84060 atgcccctgc cctctttcat acctgtatcc ccagcctcca tgccctgacc tgaagagaag    84120
tacacaaaga ttactggtaa actcacaggg ctatgtctaa ctggctgagt cgttcatgga    84180
ctaggttgac tccctgtgat aggggatgtt atgaaatatc gttctttctc accagcatct    84240
taataaagat tataaactta ttattgggac tttcaccttc ttcattatgt catcaaacgt    84300
tgtcttgggt tctctcttgc ttagtattct ggtaattctt tctccactag attttcctca    84360
tgaggcatgt catgtattag tctaacattt ctattatatt tctacctcta ttgatccttt    84420
agtttgttaa tctattacta ttattatcat tatcatcatt ttagagacag ggtctcactc    84480
tgtcacccag gctggagtac agtggcacag tcattgccca ctgtaccttg aactcctggg    84540
ctcaagtgat ccttctgcct cagtgtccca agtaagtagg actacaggtg cacagcacca    84600
catccagcta atttttaaa caattttata tagagacaga atcttgctat gttgtccagg    84660
tgagtcccaa actcctgggc tcaagcgatc cttctgcctc agcctcccaa agtgctggga    84720
tcccaggtgt gagccaccgt gactggctct gcctatcctt ttctgaaatt cattcttcac    84780
cagtatcaac atgggtatgg gcgtgcaagt gaacatcaaa tatgctctgt gtaactgcac    84840
tactattttc agaacctcaa tctagctgta aagattattt accaagcact gaattaaggt    84900
gggctttgaa gtatcatgtt gatgtaatat tgccagggaa agggcaatat aaattgcagt    84960
atacctatta ttatttttaa taatttggaa ggcttaccag tccatttgca ctaggttttg    85020
tttttttgtt tttgagacgg agtctcgctc tgtcatctag gctggagtgc aatggtgtga    85080
```

```
tgatctcggc tcactgtaac ctccgcctcc caggttcatg tgattctccc actcagcctc   85140
ccaatttgct ggaattacag acacccacca tcatgcccgg ctaattttgt attttttgtag  85200 agacaggggtt tcaccatatt gcccaggctg gtcttgaact cctgacctca ggtgatccgc  85260
cggcctcggc ctcccagagt gctgggatta caggcatgag ccaccatgcc cagcccattt   85320
gcattaggtt ttataaagaa tgtgtatctg cctgtctcta taatcagatg caaacaactc   85380
actcaaaaaa tacatatatt ggcacatcaa ccctgccccc ttgtggttta agacagatgc   85440
ataacatggt ttaataatga aaccatattt caaaatacca atacagtgtg gttattacta   85500
cttaatagaa aggttctctc cctactagtg cccaataaga aactaatgaa tattttgttt   85560
gtgaagaatg gcagcaaaca ccccttttatt ggtattgctc tggttttaaag acattattga   85620 tattcgtcaa actgcattgc atttactggt tccatttttac caattgctag gatgcttctg   85680
agtttctgag gttttgaccc atctggaagt ctctgagcca ccttgtctgg gaaggaaagg   85740
ccttctgctt tagtggaagg gccttgccaa gagggtagag gcttaggtag agcccaagct   85800
gttttgtcat ctggcgatgt ttgcaatctt gagcaagcac ttgtctgaat ctcagtgtag   85860
tcaacagaaa gttgagagta atagcatcag ccttgcctcc caccagcctg ttctaaggct   85920
tcagtggtgt tattccttca attagaactc actgcagacc tcaactgaaa ctcgggcccc   85980
ttggtgctgt gttgtcctgc ttagaggatg atttactagg ttcaagttga gatgagggtg   86040
tcggcagaca ttaaaaccaa agtagcaaag gagggcaagt ctgaattcta gaggcttaaa   86100
atgtcttgct tgtcccggtc tctgaggaga agcaaagatg agccagacac ggtgttacct   86160
gcctgctgcg gccctgtctt tcccctggac tcctcaaagc agatctgaac ctagagagca   86220
agggaatggc tcacagcatc cagaaaccta agcaacctgg gcataaaaga atctggtatg   86280
tgctgagttc cagaagcctg tgagccacag atgtggatct gttatcacat ccaaaatagg   86340
aggcaactgt gaccatgcgg tggggacatg ggcacaaaca agcagtctcc taagtactgt   86400
cccagctccg actctaaatt gtggccaaca gatgcagaat tctagtgctt gcccagccaa   86460
gacttttcat tcatgaagct ctaatccatt tccaagggaa aaagagcttt acatttctcc   86520
catgtatctc cccatctggc cacagaattt atatctcaga ttttatgtct tctcatttgt   86580
attgtatctg agcattttttc aaattttcct tttttttttt ttaatatagt gttggctctc   86640
tctgcgtctc ttagggtcta ccagtctttt tttcaatgtt tcaacttcag catatagaaa   86700
taaatcacat tttctggtaa aacaattact tccctcttaa gtaaaaggtt tggtggtatg   86760
tagacaaaat attgtaaaga catatacaag ctaaagcacg cttttatttg gctggtggga   86820
ggggttttcc tttgaatata aattccatac ataagcatgg tctgtgtttg cccagtaaca   86880
gtgatattcg catacccccag gcttccatag ctggaagaac catctttagg tttaggtaag   86940
agtcatatga aagtgagtct ttgggcctgt aatcccagca ctttgggagg ccaaggtggg   87000
cggatcactt gagatcagga gttcgagacc agcctggcca acgtggtgaa acccatctct   87060
actaaaaata caaaaattag ccaggtgtgg tggtgggcac ctgtaatccc agctacttgg   87120
ggtgctgagg caggagaatc gcttgaaccc gggagatgaa agttgcagtg agccgaactg   87180
gtgccactgc actccagcct gggcaacaga gggagacttc aatttaaaaa aaaagaaagt   87240
gaatctttgg gttattaggg gatgacgaat gagggtcaaa ctggaatatg aagattttca   87300
gacatttctt caaatgcaaa ttgttcttcc ttttttctatc tttgagggta ggcagaccgc   87360
aggttgactg gagccttgat tcagctgcag cacacactga tacgtaggtg ttgttcaagt   87420
ccctgaggcc atccaaaatc actgtcatgt gactgtcaaa aaagtcaaat ctgttctatt   87480
```

```
aaagtgtaac tgcttctagc caagaagaaa tttgctgcct ttttttaaag ggtaccatga   87540 ctttttttttt tttttttttt tttttttggt gtcttctgcc aactactcat tactagtacc   87600
ctgaattcta tttcatcatt atctccaatg ttaaagaatg gtgtaatgtt agccgggcgc   87660
gatggctcac gcctgtaatc ccagcacttt gggaggctga ggcgggcgga tcatttgagg   87720
tcaggagttc aagaccagcc tgaccaacat ggagaaaccc tgtctctact aaaaatacaa   87780
aataagatgg gcgtgatggt gcgtgcctgt aatcccagct acttaggagg ctgaggcagg   87840
agattgcttg aacccgggag gcagaggttg cagtgagctg agatcgcgcc attgcagcct   87900
gggcaacaac agcaaaattc catctcaaaa aaaaaaacaa aaaattgtgt aatgtcagtt   87960
tcaatgatag ctctgcttca ttttttatgc acttgatttt cttcgatttg gttggttttg   88020
gggaagtcaa caaaaaatac aaaagatgcc aacagacaca acaccatcca gcacaagtta   88080
ccttgctgaa acgcatggat tttctaagtg gcatgaagac tgtaaactag ctcagagccc   88140
tggaaaagga aataatatgc atagcttctt ccctcacata ttcctgcttt gtggaacaaa   88200
gttgaattaa gactccagaa attcatctaa tatattctcc ccccgccaca ccacatagtt   88260
tttcttaatc caaataagag gaaaggaaag aaagccaggc ctggtggctc acacctataa   88320
tccctgcact ccagcacttt gggaggccaa ggtagatcat gtgagctcag gagttcaaga   88380
ctagcctgtg caacatggcg aaaccccacc tctacaaaaa aatacaaaaa ttagccaggt   88440
gtggtggtgt gtgcctgtag tcccacctac ttgggaggct gaggtgggag gactgcttga   88500
gcatgggaag tcaaggctgc agtaagccct gatcacacca ctgcactcca gcctgggtga   88560
cagagcaaga ccctgtctaa aaaaaaaaaa agaagaagaa aggaaagcaa gaattaatgt   88620
ttgttgatcc tcctgttctg tgttacttac atttaatctt cacaaccatc ctgggtggtg   88680
gtatattatc cccatttcat aggtgataaa attgaggctt gggaatgttc agtgacttga   88740
gaactagaat tcaaatcaaa acctgactag gttctttctg tcacaccaag ctatgatgat   88800
gggtacacgc tatatttatc acatatcaaa ggacctccta aggggggcac agtgtaaata   88860
gctcttcaaa ataatgccat tgaagctgag tgtggtgcct cacacctgta atcccagcac   88920
tttgggaagc ttaggcaggt ggattgcttg agcccaggag ttcaagacaa gcctgggcaa   88980
catggtgaaa ccccatctct acaaaaagtt aattaattaa ttaaataaaa caaaataatg   89040
ccactgaaac ccaaggaata aatgcgtaat caggttacca aattattacc aatttatgat   89100
tgggtactac ctaaacatca aaaggatatg tatcaagcag taggaataaa tataaatgga   89160
actgtgttta aaaagagag ggcaaagagg aacacacgaa gtgaaaatag aagtttacac   89220
agttgtatag agaaagggag aaggaaatgt ggcattttcc tcctcaggag acaaaaaatg   89280
aagagtcagg aactaaatag gacagaaagt ataataaaag gcaacctagg tcagatagaa   89340
gtttgttgaa gttcaagata aacattgttt tgctaaatgc caaaattttt attttcact   89400 ttaaccgttt ctgggggaaa ctgttacgtg tgcctcgtat ttttctgccc taataaataa   89460
ttattgagca taactgtttg gggagagttc aagatcatct tactattgta gctcttcatt   89520
ctcatttatg ttattgggga cttaggcagc ttcaccttaa ggtaatatga tttgacgctg   89580
gagtaaacaa actagatgtg acacgtagga tctaaaataa gaaaggtctt aaaatataaa   89640 tggctttta aaaattgtac tcctgaaatt ttgagagggg ctgtcgagac tatcatgggt   89700
tgacggctag gctgggccac ttcgttggct gtgtgagttt gaggaggtta ttttaataag   89760
ccagagcctt agtttttttc atctgtaaaa tcatgataat aattgatgac acagagctga   89820
tatgagaatt taatgagaaa atgctcattt ggtagttagt acagagcctg gaatatacta   89880
```

```
agtgctcaat aaatattggc tgctgttact ggccaatcga ttccatgctt ccaagaagcc   89940
ttgtgattat aattttgctt cccatgtagt tgcactacaa gacaaaacta ttgagtccct   90000
cgcacacgta aatattttgt tgtaactaat acattgacac cgttttatt taggatttta   90060 tggaatccac caatggttgt agtacagttt ggtgactgag taaataactt ggaagtgaca   90120
ggaatggatc ttaggttgtc atctgtgttc tctcactgtg ataatacgta ctaatataaa   90180
tgggctattc aacaacgaac aaatttaagc tataaatcag attgtaatt ttgactgtat    90240 tttaagttac atcaaaaata agttttttcc ctctctaaca cttaatatta actcacaaca   90300
ttgagttagc taataaatat tgcatatatt gttcttaaat atttataata atttttatat   90360
gccataaaat atggtattaa tatttaattt tattttgtc ttgcaggtgt aaagggtcaa    90420 gttttgatc agaatggaaa tccattaccc aatgtaattg tggaagtcca agacagaaaa    90480
catatctgcc cctatagaac caacaaatat ggagagtatt atctccttct cttgcctggg   90540
tcttatataa taaatgtaag tatgcaatgc tagttattgt tattaaaata ttatagaact   90600
cataatactt attcacccag aaggaatcca aaataagtct aggaagttca aaagtagatc   90660
catcgagaca gaaagaaagg atagtgtcag acttgcaatt ggcaggaggt ggaagaggtg   90720
gaaattatat gaaaaaaaaa aaaaccacaa aaattcatat tttttccctg atggcaattt   90780
ttaaaaaatg gaagccaaat cctatctctt gtgatatctt ttatgattaa aatgtaaccc   90840
gattaataat aaagaataag caatgtagca aaggtagttt atagtttccc aggatacgac   90900
acaacaccca ttccacggca tacactttct actataaaaa atgaattgga taagttcct    90960 tagaattcat tttataagtg aaatctgatc cacaaatttt aacactatat tcagcaaatg   91020
ataaacatat tttgcagccc tttttcatc gatgcaagta aaatttcagt ctttaattcc    91080
ataaaatata tatttctgag tcattttatc cgaagacagg aaggcatgga ctaatttgag   91140
cctgagtgga tttatgtgaa agaactaaat gaataagtat tgatatagtt ggccagattt   91200
tgcctctttc tctttgatgt gaatttctct gagaaattca ggattcttct attttgctta   91260
gtggggctta tgccaaccat agcagtcatt ctatatagag ctaatcctgg gagaaggtag   91320
tcatctcttc tgtagtgaaa actgagttgg tattttatta tttcatcttg aggacatcat   91380
ggaaaaaaca tggtttttag tttataaaac tatagaattc agagcctcca tgctccatgg   91440
gttctcccca aggtgcctag atgtgaggct tatcaattgc taatccttt aggaatttct    91500 actcctgccg agaaaatgga tagagcttga aaaatctcaa ctcactgtga atctttgtct   91560
aaaaaggccc tttattttcc tcctatttac tgtgatattt ctattctatt taaaaatatg   91620
attttccctg tagtgaatct aaacttatat gcaacctcat aaataagcca cacctttaga   91680
ataaagttat gaattgttca tttcccatta gttagactaa cacagtacac attgaccta    91740 gatattagtt ctaggataat atttgaaggt aagactctgg acattgaaat gaatgtgtaa   91800
aatacatacc aatgagtggt tatgtaaatg tcattcccca ttttttccct tctccaccat   91860
atataataaa agcatttctc agtagacatt gcctgtagtt agtttagcat ttgtcttgtc   91920
ctgatcattt cctccactaa aaaaaaaag aaagcctaac caaagattca ggctgatatg    91980
aacaaaacca ggtaaaatca aagctttttaa aggagggtgg atgtggtggc tcatgactgt   92040
aatctcagca ctttgggagg ctgagaggca ggtggatcac ttgaggtcag gagttcaaga   92100
ccagcctggc caatgtggtg aaaccctgtc tctactaaaa atacaaaaaa ttacctgggc   92160
atggtggtat gcacctgtaa tcccagctac ttgggaggct gaggtaggag aatcgcttga   92220
acccgggagg cggaggttgc aatgagccaa gattgagcca ctgtactcca ggctgggtga   92280
```

```
cagagcaaga ctctatctca aaaaaaaaaa aagaaaaaag aaaagaaaga aagaaaagct    92340
tttaaaagaa gcaataggct tgtaggtcag ctgaaaagaa attagtaagt tgagaaaata    92400
attctacttg aaaataatct tgatatccaa ggaggatgtt aaatacacac ttgggacaaa    92460
gggaaagagt tatctcttta cccttctgcc ccacgaaaag gatggtggca gaaacatctg    92520
ctgcttcctt ctcttgactt acattgccag atgaggtacc catctgtcct tatttcattt    92580
tgtaattctt ggcaacagca ttcacaacgc tggtctctgt caacaggcat tggataactc    92640
agcctgcagg accaaatctg ttgctggccc agaggtctgg tagattgtta catgcattgc    92700
acaaaggctg cattttagtg atggatatca gtgttttcag tgtgggcacc acgaaccatc    92760
ttaagtcact catataattg tctcttgttt cttctcaggt tacagtccct ggacatgatc    92820
cacacatcac aaaggtgatt attccggaga atcccagaa cttcagtgct cttaaaaagg    92880
atattctact tccattccaa gggcaattgg attctatccc agtatcaaat ccttcatgcc    92940
caatgattcc tctatacaga aatttgccag accactcagc tgcaacaaag cctagtttgt    93000
tcttattttt agtgagtctt ttgcacatat tcttcaaata aagtaaaatg tgaaactcaa    93060
cccacatcac cacctggaat cagggattgc tcactccagg ttactgcaac cctaactcac    93120
tctagtggga ccttgactgg agaaactcca cgatcttcct gaagaagaga atggatgtt     93180 tccaaattcc acaataagca atatgtggtg ataatgaaaa gaatgattca gtcttgacgg    93240
tgaatggaag acacttacct aacaagtact gctcatttac actcaaatta atcttgaagt    93300
agtcttaaaa tgtgtaagaa gttaaaactt gagaagcaaa aaaatgcctg caaaagaag     93360 atcattttgt atacagagaa ccggatgaat ataagcaatg aagatgaaca tttattgatc    93420
ttctacatac aagacttcac cataaggcca ggagcagtgg ctcacacctt gtaatcccag    93480
cactttggga ggccaaggtg gcggatcac cctgaggtta ggagttcaaa accagcctga     93540
ccaacatggt gaaaccctgt ctctactaaa tattagcggg gtgtggtggc gggcacctgt    93600
aatcgcagcc tttcaggagg ctgagacagg agaatcgctt gaaccctaga ggcggagttt    93660
gcagtgagcc gagatagtgc cattgtactc cagcttgggc aacagagtaa gactctgtct    93720
caaaaaaaaa aaaacaaaaa caaacaaaca aaaaaaacac ctcaccatga gtgctacatg    93780
tgaatagata ttaagtgcca tatataatta gttctcagaa gaagggagaa atgatcatag    93840
gactgggaat tgttttgcaa acgttctagg agatgtgaga gaaaatatgt aaccacatct    93900
tagtggccca agaaaataca ggcctgaagg gataagattg tgtctctata gagcttcaaa    93960
gcatacaggt caattaagaa agcccctctc tctccagagc cgtttcccta gcttttggca    94020
cctggatgcc acagtcctcc attaggctga tgactccaaa gatgtaactc tagcctcttg    94080
cctgagcttc agactcgcgt cccactgccc acaggacaca tccacctgga tgtgactcac    94140
aggtacctcc aacccatcat gtggagatac tcatcctgtt cccctagag ctgctcttcc     94200 tgctgcattc tctctctcaa ttactgggac caccaagcta ggaacctggg agtcatcctt    94260
gatactttct cttcctccctt aatcctgtgt attcagcaag taactaaagg ttggtgttgg   94320
ccaggcatgg tggctcatgc ctgtaatccc agcattttgg gaggccaagg cgggcggatc    94380
acttgaggtc aggagctcaa gaccagcctg gccaacatgg tgaaacccca tctctactaa    94440
aaaaaaaaaa aaaattagtc gggcgtggtg gtgcatgcct gtaatcccag ctactgggga    94500
ggctgaggca ggagaatcgc ttgaacctgg gaggcagagg ttgcagtgag ccgggattgc    94560
gccattgtac tccagcctgg gtgaagaagt gagactctgt cttaaaaaaa aaaattggtg    94620 ctgataaaata ttgatgaatt ctgctctctg ctctctatgg ttgtcaacac tgcagagttg    94680
```

```
aggcctcata tctcacctgc actgctgcaa cagcttactg gtcccttgct cccagccttc   94740
tcctcttcag tccatcgtcc acacagcact ggggaagggg agccacttga aacaaaagtc   94800
aacaactggt tgtagttcat aaacacagag ctgtttgtgt ccctgtatc tggaatgcca    94860 ttatgaccca ctacattttt tctttcctac ccctcttaaa actcagttca ggtagcagct   94920
ccactaggaa gccttggctg accataatcc cattcaattc catttcacct cttcgcaggc   94980 agtctgggt tagggaccct ttctctttgc tccccaaaat aaactggtta tctctactat   95040
tggatttaca acattgtatt ataatcttct ccatgtgtgc cttctctagt agaatgtgag    95100
ctctttgagg ccaaggtcta tttaatttgt ttgaaaaatt cattgttata tcctcaaagc    95160
ctagcacata gtaggtactg aatgaatgaa tgaacaaggg gtgccaggag actgctactc    95220
ccagtccttc ccagaaactg cctagggctt tgagtcattt tatgaagcta ggtcttaatg    95280
cgtaggcaac ctcccagctc actatgaacg ctgacagaag agtgttttca tgtctataat    95340
caagaattcc agatacattc cttttactga accttgaatt gatcctaaga ttggtagtaa    95400
aggtattatg ttacctccta acagcactac aaagtacctt tttttatcag aaaaaaattt    95460
taccattagg actcaatttg aagtactaat gcttctcaag ttctccacta tgagagttac    95520
cctgtattag accgttacct ataagaatta aggggtaaag cactaaacag aaaagaaaaa    95580
aaaaatagca actctggtga gcagatttct ttcctttctt ccttccttct cctcttccta    95640
ccttcctccc tcctttccct ctcctcccct tctctccctt tccctcccct tcccttcctt    95700
ttcttctttc ctccgctccc ctccccttcc ctccccttcc catccttctt tctctttttt    95760
ttacttaatc cccagtgtga cagtaatata ggctgatttc tagaagtgtg gtgtattact    95820 catgaaagt gagttgcctt ggttattact ttcaattgaa agttctatgg gatctagaaa     95880
tgagacatac tggcatggag agtgagaacg acaaaggaat gaagagctac aggagcattt    95940
aggccatttc tatgccaagc ttattctaca tgcacaaaat catacatgtt aataaatata    96000
aacaaattgg aggcttattt aaaccaatta tgaaatctgg taatttgtgc agcagcaata    96060
gatgataacc aaaaaaaact cataataatc tgaatatctt gatcatttgt atttaaagaa    96120
gcagtaatta tatacttgaa agtacataat atagtattgc aaaaatgact ttggtatatt    96180
acaaattaaa agtatataag atgaaacttg atttgctatc aagccccaag caattttca     96240 actgggcatt gaattctaac ttttctaaga tagcaatttt tgaagagaca cgaacaaaaa    96300
tctgaattag ttcatgagcc ttaatgtaaa tctcttgctg aaatagtttt taaaatcaga    96360
atttagttat ctatcagact caaaatcatt taaagactaa caaaacacaa tcatgatatt    96420
ctaactgtgg tcaaaccagg tacccaagcc acctccctgc ccaacgcctt tccggctttt    96480
cccctccctc ttgggctggt ggttatgctc ctccagctct agttcagcta taattccttt    96540
tatagagaaa ccaacctgat acacactttc atgatgggag aaaaatgtgg gagtgaaatg    96600
gtatttagaa agcagcagtc aggcacggtg gctcatgcct gtaatcccag cactttggga   96660
ggctgaggca ggcggatcac ttgaggtcag gagctcgaga ccagcctggc caacacggtg   96720
aaaccccatc tctactaaaa aaaaatacaa aaattagccg ggcgtggtgg caggcacctg   96780
taatcccagc tacttgggag gctgaggcag gagaaatcgc ctgaaccag aaggcagagg    96840 ttgcagtgag ccagatcac atcactgcac tgcactccag ccggggtgac agagcgaacc    96900
tctgtctcaa aaaaaaaaaa agaaaaaaga aagaaagaaa aaaggcagaa gccctggatt   96960
caaatccgcc acacattcag tttctttatc tgtaaaatgg agaccacccc ccgccacgct   97020
gaacggtgat tctgtgactg gtaagagatg ctacattttt ggtgcttgtt caggtggagg   97080
```

```
aaagatgata gttaacactc aggtaataag tattttgaag gcagtataat ataccttctt    97140
aaagagtata cctactcaaa tgttggtaaa tgttgacatg attgaatcta aatggcaaag    97200
agtattttag aaaaacatta agtccctgca gataaatgac agtgttgatt tggatgctta    97260
attacattca gacatgaact gttggatgta tctgaaatgt taaaagcttt ttctcaacat    97320
ttccaaaagt cttccaaga aatcaatgtt atgttttgtt ccagaagcaa atttgcattt    97380
gtgatctgtt tctaaaaatg gtacaagtta gctctgttta gaaagtaaaa atatctgatg    97440
ttagattgga agtatctctt cctggggaat ccagaaagat aagcatagca tattgtctta    97500
ctgcaataga taagttgctt attgagaagt ctggttgtta ttctatatgg taacaataca    97560
gttgatgtat attttatgat agatcccttta tattttcctc atgactttag aaggggggaag   97620 ggggagaaaa ttatgatgac cagactagtt aaagagcatt gaaagtccac agtactgtag    97680
ctaaagtaga agtttgggtt tgttatagac tttacattat atcaactaat aagcagatac    97740
tgtacagtat tgctcaccat tttatcatac ttttgcatat gaactactcc attgcctttt    97800
atagatgttt tatagctgat cttaccagtt ttcctggtaa cttttttat ttctttttt    97860 ttttttgag acggagtctc gccctaacac ccaggttgga gtgcagtgcc gtgatctcgg    97920
ctcactgcaa cctctgcctc ccgggttcaa gcaattctcc tgtctcagcc tcccgagtac    97980
ctgggactac cggtgcctgt ctccacgccc ggctaatttt ttgtatttgt agtagagacg    98040
gggtttcacc gtgttagcca ggatggtctc gatctcctga cctcatgatc tgcctgcctc    98100
tgcctggacc tcccaaagtg ctgggattac aggcgtgagc cccgcgccc agccactttc    98160 tttaatacta taactaagaa tttattaaaa tgcacaaatt gtctaagact gtaaagttta    98220
tgggggagag gccatgacta cctctgaatt tagtaaattt aaaatatttc tgattctcaa    98280
taaagaacta atatccatat aaataatgct ttttcccat tatgttacct gaaaataagt    98340
acttatgcaa gtataacaaa gtccactaaa aataactgat taccaccaaa taaagcttgg    98400
gaaagaccaa acttaatgac cttttatgag gcaataacat tgcaacaact cttcaaagtc    98460
cagatagttc ttccagaaca agttacatat gctatatgtt atatatatta tatataatac    98520
attccaaatt aatttgtgtt gtggggcagt gtgttccatg gacaagatga tggatggaaa    98580
gtatgccttc tggtcagaaa aaatatttga aaattcacaa tttatattaa tgtaataaag    98640
aatctgagaa atgcagaaaa gaaatggatt tcccaaacat gctaagctat gggaccattt    98700
ccttaaataa tacagcctcg taccatccct ttggattaac atacctatat ttccaaacac    98760
attttgggaa atactgatat atagagaagg cttttgttct gaataacaaa ttttattgat    98820
ttccaggtgc ttttgaaata cagagaacag tggtaaacaa agaatttgcc tccagtagga    98880
actgaaaaac taacagtcct aaccctgct aatatcgact tagtcatagg acagaggatg    98940
ggctcaagct tacatctgct ctttgaaaca cgctaaacaa ataatagttt aaatgagaca    99000
ttgctgagta ggaaatggct aaattacagg taccaatttt taaaaagtga cgtctcaatt    99060
tagaaaataa acaggaaata gtttctctgt tttcaagaga atttcattac atagaagcct    99120
cttaagcaga agttccctgg tatatttacc tagacttcaa cgtttaaatt tgcagctttt    99180
tttttttttt ttgggacgaa gtctcgctct gtcacccagg ctggagtgca gtggtgggat    99240
ctcggctcac tgcaacctcc acctcccagg ttcaagtaat tctcatgcct cagcctctcg    99300
agcagctgga attaacaggc acatgccatg acgcctggct aattttttgta ttttttagtta    99360 agacagggtt gcaccatgtt gcccaggttg gtcttgaatt cctggcctca agtgatccac    99420
ccacctcagc ctcccaaagt gctgggatta cagggggtgag ccatcacccc ccagccaagg    99480
```

-continued

| | |
|---|---|
| gtttttttgtt tgctgtttga caactgagaa tagaactatt atttctctgc tctcttggag | 99540 |
| tggtctctca gcgctgttaa gagtctacca agcgtagtga ctcacatctg taatcccagc | 99600 |
| actttgggag gccgaggcga ctggatcacc tgaggtcagg agttcgagac tagcctggct | 99660 |
| aacatagcaa aaccccatct | 99680 |

<210> SEQ ID NO 4
<211> LENGTH: 51039
<212> TYPE: DNA
<213> ORGANISM: Homo sapiens

<400> SEQUENCE: 4

| | |
|---|---|
| tggtctctca gcgctgttaa gagtctacca agcgtagtga ctcacatctg taatcccagc | 60 |
| actttgggag gccgaggcga ctggatcacc tgaggtcagg agttcgagac tagcctggct | 120 |
| aacatagcaa aaccccatct ctactgaaaa tacaaaaatt tgccaggcat ggtggctcat | 180 |
| gtctgtaatc ccagcacttt gggaggccga ggcaggcaga tcacgaggtc aggagttcaa | 240 |
| ggctagcatg gtggctcatg tctgtaatcc cagcactttg ggaggccgag gcaggcagat | 300 |
| cacaaggtca ggagttcaag gctagcatgg tgaaccccg tctctactaa aaatacaaaa | 360 |
| aattagccat gcatggtggc atgcgcctgt aattccaact actgggaggc tgaggcagga | 420 |
| gaatcatttg accttgggag gcagagtttg cagtgagctg agatagtgcc actgcactcc | 480 |
| aacctggagt gagagactgt ctcaaaacaa acaaacgaac aaacaacaac aacaacaaaa | 540 |
| aaaaaaacgg ccaggcgcag tggctcacac ctgtaatccc agcactttgg gaggccaaag | 600 |
| caggtgggtc acctgaggtc aggagttcga ccagcctg gccaacatgg tgaaacccg | 660 |
| tctctactga aaatacaaaa actagccagg tgtggtggtg gacccctgta atcctagcta | 720 |
| ctctagaggc tgaggcagga gaatcacttg aacctggggg gcagaggttg cagtgagccg | 780 |
| agatcgcgcc acttcagtct agtctgggcg acagtgaaac tccatctcaa aaaaaaaaa | 840 |
| aaagggtct accgttagtg gacacccttta gtcttccaac gagatacttc cacctcccac | 900 |
| cttgtggtta aaaaatgctt aactttgggc tgggtgcggt ggctcatgcc tgtaatccca | 960 |
| acactttggg aggcagaggc aggcggatca tgaggtcagg agttcgagac cagcctggcc | 1020 |
| aatatagtga aaccctgcct ctattaaaaa tacaaaaatt agctgggcat ggtggcaggc | 1080 |
| gcctgaattt ccagctactc gggaggctga ggcaggagaa ttgcttgaac ccaggaggca | 1140 |
| gaggttgcag tgagccgaga tcatgccact acactccagc ctgggtgaca gaacgagact | 1200 |
| tcgtccccc caaaaaaaca aaaagcttaa cttttgaagag atttggtctt ctcagatgcc | 1260 |
| tcctataaaa agaaacaaat gtgagaaaag gtagaaaagg cctttttgt agggagcaat | 1320 |
| ttttctaaa aaggcttttc agccaagacc ctctctctta caattctgac accatatcaa | 1380 |
| cttttaagac tacttttttc ttagaatgct tcttttttgc catttattgc acaaacaata | 1440 |
| atttgggggg ggactttaaa aaatcataat caggccaggc acagtggctc aatgcctgta | 1500 |
| atcccagcac tttgggaggc cgaggcaggt ggaccacatg aggtcaggaa ttcgagacca | 1560 |
| gcctggccaa catggcaaaa ccccatctcc actaaaaatg aaaaaattag ctgaaataac | 1620 |
| acagctactt gggaggctaa agcaggagaa tcacttgaac ccaggaggtg gaggctgcag | 1680 |
| tgagccaaga tcacgccatt gcactccacc ctgggcaaca gagcaagacg ccatctcaaa | 1740 |
| aaaacaaaca aaaaatcaca atcagtgaga ttaatgttta atgaacatac tgttattttt | 1800 |
| tattttttta agagacaagt ctccatctgt ctcctaagca gagtgtagtg gcgcaatcat | 1860 |
| agctcattgt aacattggac tcctgggctc aagtgatcct cccacctcag tctcccatgc | 1920 |

```
atgccaccac aattttttgg atacagggtg tcattatgtt gcccaggctg atctcaaact   1980
cctggcctca agtgatcctc cttccttggc ctcccaaagt gttgagatta caggcgtgag   2040
tcacagagcc tggcccagga tgttatttta aaattgtctt tttgtcttct aaatcaacaa   2100
gaacttgata gttgctttca atgccaatca acatccttta ctactgtata cacaatgtat   2160
ttatttgaca tttgaaagga gatacggctg ggcgcggtgg ctcacgcctg taatcccagc   2220
actttgggag gccgaggcgg gcggatcaca aggtcaggag atcgagacca tcttggctaa   2280
cacggtgaaa ccccgtctct actaaaaata caaaaaatta gccaggcgcg gtggcgggcg   2340
cctgtagtcc cagctactcg ggaggctgag gcaggagaat ggcgtgaacc tgggaggcgg   2400
agcttgcagt gagccgagat tgcgccactg caatccggcc tgggctaaac agcgggactc   2460
cgtctcaaaa aaaaaaaaa aaaagaaag gagatacaaa aggatgttac aacctgctat   2520
ggcaagaaga tacaaggaa catattggta tgaacagaat acctcagagt tgagtgtata   2580
aaaaaggctt aattcaccag atgcagtggc tcgcacctgt aatcccagca ttttgagagg   2640
tcaaggtcaa gacacgagga ttgcttgagc ccaggagttc aaggccagcc tgggcaacat   2700
agcaggactc tgcctctaaa aaagtatat atatatat aatgtacaca cacatacata   2760
cataaacaca tatgtattat atatatatat gtaatatatg tatattatat ataatatata   2820
tattagccag gcatggtggc aacaggcctg tgttcccagc tactcaggag ctgcagtga   2880 gtcatgtttg cgccactata ctccagcctg ggtgacagaa tgagaccctg tctcagcaaa   2940
aaacaaataa aaaacttcaa ggtggagtag gggttaattc aaggctacct agctggatt   3000 tggggtgatt atggtcgagt ggatgcaaac agaatattaa acttccattc attaaaagtg   3060
cttactacct gccagacccc atactaggct ctatagattt attgtctcta aggtcactag   3120
gcgagtaagt accagatctg tgactttgaa cttcccacta caataagctt atgaactttg   3180
tttaagcaaa aaaggtttga aaagtgaaaa gcaagcaccc atttcatagt gttctaaaag   3240
tctaaaataa tccagtagaa catcagagat aaaatccaaa aagcaagttt ttccccaat   3300 atttaaatca gggaagcaac atgatggtat ctgtaaacta taactgaacc aaaaatagga   3360
ccaaacgtag tgaaatccat ttagggagat attactgtga tcttgaagga aggcctactt   3420
aatacaggac agtgggctgg ggaggtgtga accaaaaata gacacaggca aaagcgctaa   3480
aatttaaccc tgagaaataa atgaaattca cctacaaaat aaatggaata aatttaaaag   3540
gtgaaatttt gggcttggcg tggtggctta cacctgtaat ctcagcactt tgggaagcca   3600
agacgggcag atcacttgac cccaggagtt tgagaccagc ctgggcaaca tggtgaaact   3660
gtctctacaa aaaatacaaa aattaggccg ggcacggtgg ctcacgcctg taatcccagt   3720
actttgggag gccgaggtgg gcggatcatg aggtcaggag ttcgagacca gcctggacaa   3780
catgctgaaa ccccatctct actaaaaata caaaaaaaat tagccaggtg tggttggcga   3840
gcacctataa ttccagctac tcaggaggct gaggcagaat gcttgaacc tgggaggtgg   3900 aggttgcaat gagccgagat tgcaccactg cactccagtc tgggtgaaag agcaagactc   3960
tgtctcaggg cgggtggcag cggggtcggg ggaggtgggg ggaaggttag ctggacctgg   4020
tggcttgcac ctgtggtccc cagctacttg ggaggctgag gtgggaggat tgcttgagcc   4080
caggaggttg aggctgtagt gagtcatgtt tgcagcactg cattccagcc tgggcgacag   4140
agcaagaccg catctcaaaa caaaacaaac aaaaggtgaa attttggaat taggaaagat   4200
gctattttta taaattggct ttaagctgtt ggctggacat ctaagttgta gcattctgaa   4260
ggcagcagag atgtgggatt gtaggactga acatgaaaa tgcctatcga atttttttta   4320
```

```
aagtctttaa aggagagctt taaaggaaag caatacgaat tcaagtatgt ttcagtacca   4380
ctcctctctc taaagacaat caactatggt tttcattcaa atactatta ctctaacgtt    4440
aaatatttga gtacagcaat catttcgat gcattatgaa taagttactg aacacgcctc    4500
ccatctgctt gctttacggt tttatttttgc ctttcgtttg ttagctcatt ttataatttg  4560
ttacttctga acaccttcca agtgctggtg ctttcagata tctacctcaa agtattattt   4620
gtaaatgtca aaagtccct cttacatata attgaaagct ggctacatgg tagacaatat    4680
gatcacaaac ttttaaacaa ttttttaagc tgaagaaata cttttttcttt ttataagtat  4740
caaatcaaaa tgtaattcag catccaccca taaagcgcaa ctaaaaactt ttcacaatgc   4800
cattaacaac ttgtggttac catcataagc ctacagacct acacactaat tatctttaaa   4860
acccttatta ggctgggcgt ggcggctcac gcctgtaatc acagcacttt gggggggccaa  4920
ggcgggcaga tcacttgagg tcaggagttt gagcccagcc tggccaacat agtgaaactt   4980
catctctgct agaaatacaa aaattagcgg ggcgtggtga cagggtgctc taaccccagc   5040
tacttgggag gctgaagcag aaccacttga acacagccag gaggcagagg ttgcagtgag   5100
ccaagattgc accactgtac tccagcctga gccacagagc aagactccgt ctcaaaaaat   5160
aaataaaaat aaaataaaac ccttattaag gatttaaaaa atcttaatta tataatgcca   5220
aaagctagtc cccgtctggc ttaggggccc acaagctcct gctttaaagc cagtttttt    5280
gttttttttct gatgtactta catttgtgcc tcacaatcaa gaggttccca gcttggtgga  5340
actttcaaag atgaggcaga aaactaaaca ggcaattaca atcttacttt tcacgctgac   5400
aagtggtacg gtggctagcc caaactcccc tccctgtccc agctacctcc cttatagacc   5460
attcacgatc acttaggcca ggctgccatg tgacctaaga aagacaggg agaacacagc    5520
atttcttact cctactaact tgcaacatca ttctctcaag ttgctctcat tggaggctcc   5580
caactgcttc aagctgccca gtgatatttg tatttctaaa gtgggcaggc atggccattc   5640
cagaaaaaga aacacattca gacttgtgcc ttttgttacc caaatatatg atattcaaat   5700
aatttctatt ttaacaactc ataaaaattt aagatcaaat aattgcattc ttgaaacaat   5760
tcttaatcat ttattttcaa cacgtgtact ataaagaacc taagaaatca gacaattta    5820
ataacccata aacatgttga atccatttgc agatttaaat tttgtaaaaa tagctgtcac   5880
tgcctccata tatcaagtgt actatgttta taatcacatt tatgctaccg atactcctca   5940
gaaaaaaaca gattctgctt ggttctagct tcagtattat gaactccaat aatgctttga   6000
ggacctccaa aggaaaaaaa cagattctac taggttctag ctgaaatatt atcaactcca   6060
aattgaagct gaagtattat caactccaaa taatgcttcg aggacctcca aaaaaaagag   6120
attctgcttg gttgtagctg aagtattatc aactccaaat aatgcttgga ggacctccac   6180
aggtaaacta ctaatcccctt tggccattta ttgagacaga cagagagaga gagagagagt  6240
tttgaagcaa caatgtacca ttagtaaagt tgctgtgcag aattacctca gtcctattct   6300
aagcttacag ttcagttgat tttattgtct tcacctaagt atatacaatt cacatatggg   6360
agaaaaacac taaatcaaga tggttatttt cactgttttg cttaagattc atatttaaat   6420
ataaatcaag aagttaatcc acagtttgag agatacttat attagaaatt ttaaatgtta   6480
aatacataat tgtaaatatg gtgtatgtac tgtttcacat acaatgggta ttgatcaaat   6540
cagtgtaatt agcacaccca tcagctcaaa tatcatttat ttgtagcaag aacattcaat   6600
acattaacta tagtcaccct actctctctc tctctctctc tcaataaatg gccaaaggga   6660
ttagtacttt taccctttgga ggtcctcaaa gcattatttg gagttcataa tacttcagct  6720
```

```
agaacttatt ccttcaaatt taactctgta cccattaaaa gtggttttgt gtgcaattaa    6780
cagacacatg ttctacccat acattgtttt ccaaaattat tgtgtggctt taaaaaaaaa    6840
aaaacccaca caacaaattg caaaaggcac tgagataaca tctgcttcta gatcattgct    6900
aggctcgaaa aataaagctt gttctaccag gaatgacaag ttagaactta gtatttgcca    6960
aagcagaaat tatatagtgt cagttatttc aggcaaacct tattcggctc tcatccccaa    7020
ctatctgtca gaacaattaa aagagatcaa aacagtccag cataactagg cttcattata    7080
taaggccatt ttgttctaag acactaataa accaaaataa gaaatattaa aatcaaaata    7140
aaagatatta tttgagctat tttcatacaa actgttggtt ccttatatcc tcccttctat    7200
aataaagggc atattttact gcaaagaaaa ttttacttta tatatatcac tagccataaa    7260
tttttgaatg tcattaatta catgttgtct agtaccatta accaaatagc gtaactattt    7320
tatgtccaca tttcacttct gtatttacaa acatatcagt aaagagttaa caatgagatg    7380
cgatcaaaca tccatattat ctgttttgta gacagcaatg tagatgattt tgtaatcacc    7440
tttcatcgga gtgaccttat ataaaaaata agtcaataat ttagaggttc taagtctcca    7500
aaggagattt tcaaatgtaa atatagaaat ggttatagat aatgagattt ttaggaaacc    7560
tctgccatgt ctgcatcctg ttaactgtta tatcatcttt tcttccagct gcgttccttt    7620
gcctgcaaca ggggtcaaga tgagttttgc ctgacttctt tgatgtcctg aactttccgt    7680 agtcctttt cttgaatttg ttcattataa atatagcttg gcatttgttt gatcttttca    7740
actgtcttca ctgcatcagt agttttattc catagttctt gcagatattt gacaggcttg    7800
ttactatatt tttcaaattc aaatccactg taagctcatt attagcagtt gctttacaga    7860
atgctttagt ccacctaacc ttttgagaat tgcacttctt ttaaagtttt tgtgacatttt    7920 atgtttatac aatctgaaca ccttgcaaca gctgcagatg aacatcatga tgtggtcagg    7980
gtagatgggt cccaaagaaa ctaacacttc tcagtgctga gctcggatgg gcctccactg    8040
accaaacacg gagcttgaga ggaagtcaag aggtatcttg gaattccaca tgctgaccct    8100
gtcattcttg aaggaaaatg atgcataatt tctgaataat tcagaaagaa cttaacaatc    8160
tttccagtta gttttttaaat aacaattctg tttatcaaat ttctgaatta acttttctga    8220
attcacgggt ttctaaaact ggccttaagc aaaagtctga aacctaggct gggaaccatg    8280
taacccaggc caagaaggta ctttaaagtg tcttagagtt gttttttcaac ttaggggggaa    8340 acaacagatt ccattaaatc ccataaagga ttttttttgtg tgtgaaaaag ggcctgatgt    8400
aatctaggtt agactcagga ggctttaaca agttttgtct tacgggtaaa tggtggctat    8460
tttcacagat aacatcatta ctcccatccc ttactatggt ttatacaaaa gaggctggag    8520
aataagtaca ttttttacagc cgggtgtggt ggctaacgcc tgtaatccta cttagcactt    8580
tgcgaggcca agacaggagg atctcttgag cccaggagtt cgagaccagc ctgggcaaca    8640
cagggagacc ctgtctctat tgttaaatca agaaaaccta aaaaacatttt tcatttacat    8700 agcaccaaat ataagagcct tttttttttt aacctagaaa gagtattttg gagagagaaa    8760
ctaaggatca gaaggtttaa gagtatcaaa aatctgaggc caggtgcctc acatctgtaa    8820
tcccagcatt ttgggaggct gaggtgagta gatcacttga gtttaggagt tcaagatcag    8880
cctggctaac atggtgaaac cctgtcttta ctaaaaatac aaaaaaatca gctggtatgg    8940
tggtacatgc ctgtaatccc agttacttgg aaggctgagg caggagaata gcttgaaccc    9000
agaaggcgga agttgcagtg agccgagatc actccactgc actctagcat gggtgatgga    9060
gcaagactct gtctcaaaaa aaaaaaaaaa aaaaaaaaaa aagagtatct aaaatttaaa    9120
```

```
tactaattct tggctggaca tggtggctca catctgcaat cccagcactt cgggaggccg   9180
aggcgggtga cctcacttga ggtcaggagt tcgtgaccag cctggccaac atggtgaaac   9240
cctatctcta ctaaaaatac aaaaattagc tgggcatggt ggtgcatgcc tgtaatccca   9300
gctgctccag aggctgagcc aggagaatgg cttgaacccg ggaagcggag actgctagat   9360
catgacactg cactccagcc tgggcgacag agagactcat ctcaaaacaa acaaacaaac   9420
aaacaaacaa aaaacaaaa aactaaatct ttcacacatt ttctctttat atcaaaggta    9480
ctaagtgaca tttaggccgg acgcggtggc tcatgcctgt aatcccagca ctttgggagg   9540
ccgaggtggg cggatcacga ggtcaggaga tcgagaccat cctggctaac acggtgaaac   9600
cctgtctcta ctaaaagtac aaaaaattag ccaggtgtgg tggcagatga ctgtaggcca   9660
agctaattgg gaggctgagg caggagaatg gtgcgaaccc gggaggcaga gcttgcagtg   9720
agccaagatc acgccactgc actccagcct gggtaacaga gcaagactcg gtctcaaaaa   9780
aaataataag ttacatttaa atgtcatata catatttaag aaaaaaaaaa accaagtact   9840
tctcatttaa gacagagtag aaattattta aaattaggag ttggtgtaaa ggatgagcta   9900
catattcaag tcaaattata gtaagtattc actattccac taccaaagta ggtcaattat   9960
actaaagaga agaaatctat gtgaattgag gcattttctc actttgatat atgtgaataa  10020
atttcaggtt gtctaaattc ctagggttat atagttagaa atatataatt ctcttataga  10080
caggtcaact aggggaaata agttagcaca atcatttgaa ttggttgtct acatactggg  10140
cagggcttat tccttttctt tagcttcttt gcacatgtaa agcaggccat aagatgtcct  10200
gttttgccat ggacaatgca accattttta ggtcgacctt gacaaatcac acaaggttca  10260
atggcattaa ggggcaaact agattccaca ctctcttctt tgtcttgggt ttcttcccctt  10320 tcaaactctt tcacatcttc ttggctgcta taaataatgc tactagaagt tgatggctga  10380
gaatagtctt cactttcttg tgattgtgaa gcttgtgtaa ttttatcatc attttcctca  10440
acacatgact ctctggaatc attcactata gttttttttac aatcaggaac atcaaagccc  10500
tcttcagctt gtgttgagtt ttccagtttg gctttctcag agatttcccc tttatctttc  10560
cctttatctt caggaagcca attctcacga agggcccaac atctgttgca atgtgatgga  10620
agggggggat tcatttcatt gcatgaagtg catttccaat agtccttcaa tgaaataaga  10680
cacacagtca gtttctgtaa ccctttaact gctcagtcac aggaatgcta gcaactttgc  10740
tatgtctaag gtaaagtata tcataggggct caatattcag tgtttcatgt tttatataaa  10800
atagtcactg taaacagcat gaggactata gttagttata tattggtata ctggaaattt  10860 actaaagaa tagattttag gtattttaac catacacaca agaaaggtta actattcaag    10920
ataatggatt acattaattt gcttgactgt agtgatcatt tcactattta catgtgtgtc   10980
aaaacatcac gttatatgtc tcaattatac acaaaacaga ttttttaaagg tcaatatgta  11040 acagtctctc ctaaagtaga gtaagtacac ccatttttt cacccttacc atcctgaaaa    11100
attctaaact aaaatatat taactgtgat gtgatattaa tcatgtacct ataaagttat    11160
ctgtttcagg atacaaatgc agttgcttcc tttagttgaa gcaagtctat gggatctttt   11220
actctgtcat gcagcctata tccactccct taaaggctca accctaggcg ctattccaag   11280
agtccatccc atcaatctag atgaaacctg cctcctcgag aaagacttcc taatccacca   11340
gtgactagaa ctaccttaga agtactctaa aaccatggct taactgagta ttccctaact   11400
ccatccacaa gagaaatgct aaaacatttt tcacagcaag tattgctgct aaaacctatc   11460
atccttggtc actaaccgta atatcctttc ctttacctgt ctatccttc ctgtgttctc    11520
```

```
atctttgtaa ctgctcaatg cttcttcctt ttcccaacgt tttatcccac aaacctttcc    11580
accatgcaat ttggataaca aactctccca catcccagc cttttacat aacctatctt      11640 cttgccttag ctgaagcatg gttcttgcct gaggacattt aacaagtgaa aactcttaag    11700
taagaggtat ttccgtaacc attttgagat tgcctcacaa atgatgttaa gacaggagca    11760
ataaagatag actattcatt cttctttttt caagttatag aagggggttt ttcacagctc    11820
ataaaaccaa agaaaaaggt cttgcaatat gggagtaaaa gtgcatcaaa aagtccaata    11880
aattccaaga tgaatatcta aaataatttg agtcttaaaa tagatttaaa aaattaaaag    11940
tatctaaaat attttactca acttgacatc aaatgattca attagttatt tattttctaa    12000
tacagtaaaa attttggaaa ctcttgaatt ttcatccttt tttgcacttg aataattagt    12060
aactgtctat aactcagaaa aaatggaatt tatttcctat tcaaatataa taaaggcaat    12120
attaagaaca aaaactaaag cacaatagtt ttaaaaaaac ctataatacc tcaggaactc    12180
agtgaagtat gcatgagatg taaacattta agtgttaatt tctttaatgg caaatcctac    12240
cacattctat aatacaaatc agtaataaaa atgtttacat ttggctgggt gtgatggctc    12300
acacctgtaa tccttgcact ttgggagact gaggcaggtg gatcacttga gcccaggagt    12360
tcaagaccat cctgggcaac atggtgacat ttctacaaaa aatacaaaaa ttagctgggg    12420
tgtgatggca tgcacctgtt attccagcta ctcaggaggc tgaggtggga ggatcacttg    12480
agcctgggag gtggggctg cagtgagcca tgatcacatc actgcactcc agcctggaag    12540
acagggcagg accctatctc aattgaaaaa aaaaaaagtt tacgtttgac aaggttggca    12600
aaatgttggt aatagttaaa gctgggtgat gagtatactg gagatacact gaaattttcc    12660
aaaataacat caaaatgtac aaattcagct gggcagtgac tcatgcttgt aatcccagca    12720
ctttgagaga ccaaggtggg cagatcactt gaggtcagga gttcatgacc agcctggcca    12780
acatggtgaa accccatctc tactaaaaat aaaaaaatta gtggggtata gtggtgcatg    12840
cctgtaattc cagctactca ggagactgag gcacgagaat cacttgaacc tgggaggtgg    12900
aggctgcagt gcactgagat tgcaccactg cactccagct tgggagaagg gtaagaccct    12960
gtttaaaaaa aaaaaaaaa aagttcaaat tccagcacct aaaaataaaa attatagcta    13020
caggtctcat cacaacaaat aaaagaaaaa tgctttaaat tattcagact ttacaaaaac    13080
attttaactt tataaaaatc agttcatttc agaaagaagc tagatatagt ctcctaatct    13140
tgaccttaat gaaattttta tttcttaaaa aagtagatgt atacttacag ctaaggaaat    13200
ttcaggatct tcttcaaatg aatctgtatc actctcccct gcctgataca cagtaacttg    13260 atataccaa taaaacacat tcattagcat caattcatcg ccctatttcc ttcaatcaga    13320
aggcttccta gtaataagtc ctaaacaaat atcatgtact acaatatatg agaaagcctt    13380
agacaatatc aaatagagta agtgagtgta aaggggaaa aaatggagga gagagaaatc    13440
cttacccaca atggtaaaag tcaatacaaa ggatgtttag gatgaataaa acaaaacatt    13500
cagctaggtg gttttacttc ataaataact aatatggaga tattaaataa tagggaaata    13560
gctagaaatg ttaaaggcag tcacttctgg gaaacagatc tctaagggta ctacttgact    13620
ttaactgtat gcatgtttta cttttataga aagtaagtta atattaaaac agtagttgaa    13680
ttatatgttt ttaaaagtga acagaccatt ataataagca tgttcattga ggtctattga    13740
cttcttggca attagtagta atataataat ataaatcaga tgataaagaa ctatgaaatc    13800
ctcaagtcca caaccaatg tgttagttta aacaaatcaa gaggtaaaga tttcaagtga    13860
aatctgaata atattatttc aatctcaaag tcaatgaaca tagaaaatat ttaataattt    13920
```

```
tccaatataa ttagagggga aaaaaaatac tacctcatca tcttcatctg agagttcttg   13980
tccttcttca ctaaggctat aatcttctga gtcgagagat tcaacttcaa attctacact   14040
aaactgatct gaaactgaat cctgatccaa ccaatcacct gaatgttcac ttacaccagc   14100
atcaagatcc taaaacaaga aaaaaatata taacttaata aacatcacct cttgacctct   14160
gtatctgttt cctaactcat ccctgtgcct ctgctgctgc cagcagggtg taacagttgg   14220
gggatgggcc tgctgctctg atccgggact tcccgaggga gatcggcggg cagaagacta   14280 ggcccccag ccagccatcc cggagccggt tgccacgcac atttcctcct cagatccatc    14340
ctgcatactg aaactagatt aaggtttcaa ggttattact acattatttt ccctgttcaa   14400
aaccccactg cataaaggaa aaacaccaaa gcctcttggc atcgaaagta cctacagtgt   14460
gactgtatta acatcttcgt ctgtcttcaa ctagacaccc ctcctccctt actaaatatg   14520
gataatcccg ccagatctag attgcttcct caactaatct tggcatttca acttccacac   14580 tttcccctc taactagaat aatttcagtt tcaaaatcct attcatcctt ctttgactaa    14640
gcctttgtca ataccataac tgaaaaggct cttccacctt taattatcct tactacttgt   14700
ataataatga attatatagt ctcacacata aattatgcaa aacataattt tgcaggcatg   14760
tttctcatct gaattatata tactttgagc taaaacctgt cactcatctt tctatgtcca   14820
aattggtaga atacacgtaa caagacacaa cacttgtaat acttatgggt ttttttttctt   14880 agaaaaatgt ctcgagtcat agatacttat gttttttaat aaactttgag attttctttt   14940
aaagagcctt tagacaatta aaaaaaattc tgtagctgct catctgattc ttcgtttcag   15000
gacttcaata aattgtataa gaacctagta agaccttcag ggcaataata tttgctgtca   15060
gtggctaagg gtaggagcat atataagcag aaggctacaa ttggaaaaag tctagaagtc   15120
gggatatggc ttattctaca cttgccacta agtagctaat ttaaccttaa acaacatcat   15180
ttaacttatt ttatttattt tgagatggaa tcttgctcca tcacccaggc tggagtgcag   15240
tggcctgatc tcagctcact gcaacctaca cctcccaagt tcaagcaatt ctcctgcctc   15300
agcctcccaa gtagctggga ctacaggcgc atgccaccat gctggctaa ttttttgtatt    15360 tttagtagag gcagggcttc accatgttgg ccaggctggt cttgaactcc tgacctcaag   15420
caattcaacc gccttggcct cccaaagtgt taggattaca ggtgtgagcc accatgcccg   15480 gcccttttt ttttttgagac aagagtcttg ctctgtcacc caagatgaaa tgcagtggca    15540
tgatctcagc tcactgcaac ctccgcctcc ggggttcaag ctattctcct gcctcagcct   15600
cccaagtagc tgagattaca ggtgtccact accacacccg gctaattttt atgttttag    15660 tggagacggg gtttcgtcat gttggctggg ctggtctcga atcctgacc tctagtgatc     15720 cgccacctcg gcctcccaaa atgctgggat tacacctgtg agccacctcg cccagcccat   15780
atcatttaac ttctaaaggc tgtagctact tcatctagaa aaggagctta gattaaatga   15840
tttccatatc tgtatcagtt ttaaaaacag aaacaaagta tattatttta cagcctctga   15900
catcaaaaga ctttttaga gtaatgttag gaaggagagt aaaagcaaca ttcatcaagt    15960
tgcagctcaa attcctaaca agggctctac taccaatcag attagaatca caagtcaagt   16020
taggatacaa ttaacactaa caaagtaacc caacaaacca aatacttcaa ctaactaaag   16080
tctttagtgc actaattta gaataagggg gtaaatcaca agaaacatta aatctcagaa     16140
aacatactct acggtagggg tctgcaaact gtggcccatc acccatcgac ttttataaat   16200
aaagttttat tgaacacagc catgcctatt tgttgacttg ttgtctacag ttgctcctgc   16260
attacaagag cggggctgag tagctgtgac agaaaccatg gcccggcaga gcccaaataa   16320
```

```
ttaactatgt ggctctttac agaaagtttg ccaactcctg tcctaggata ctataaaaat   16380
actataaaaa ataccatgaa aaaatgcaat attgggagtg gtttttaaag ttttggctaa   16440
tgttcgcaaa agaatgcccc agaaactatt aaattatctc tctctatata tatttttaaa   16500
atatataaaa taaatattta aaatatatat ttatatttat ataaatagta atatatataa   16560
tatatacagg tgcctgccca tttatattta cataaatata tattttata tttatataat   16620 tatattttta tatttatata aatatatata tttatattta taaaatata taattatata   16680 aatatatata acaatgtaat atataatata cattaatata taatagattt ataattatat   16740
attatatatt tatacattat ttaaatataa atatatatat atatatattt tttttttttt   16800
tttttttttt tggagacaga gtctcgctct gtcacccagg ctggagtgca gtggcaccat   16860
ctcggctcac tgcaagctcc acctcctggg ttcacgccat tctcctgcct cagcctcccc   16920
agtggctggg actataggtg cccgccacca cgcccggcta attttttgta ttttttagtag   16980 agacggggtt tcgccgtgtt agccaggatg gtctcgatct cctgaccttg tgatccgccc   17040
gcctcagcct cccaaagtgc tgggattaca agcatgagcc actgcaccag acctaaatac   17100
tatatattta aaaagcatca ggctggaggt ggtggctcat gcctgtaatc ccaatactct   17160
gggagccaaa gcaggagaat cacataagcc cagcggtttg agaccagcct gggcaacagg   17220
ccaagatctc atctctgaaa aaaaaaaagt aaaaaaaatt agccaggtgt ggtggtgcac   17280
acctgtagtc ccagctaact ctcaaggctg aggaggaagg attgcttgaa cccaggaggt   17340
tgaggttgca gtaagccatg atcatgcgct gcactcccgc ctgggcaacg gagtgagaga   17400
ctgtctcaaa aatttaaaaa atatatattt ttttaagcat cagataggct tgctctgcaa   17460
agatcttaga tctttgtagt caaaaatacc tagaattgtt tgaattccaa ttgtgacaat   17520
tagttgtagg aaccttaaac aagttattta aaaccccagt cttagctaaa aatggaatct   17580
gaggctgcaa agatgacaga agatcataat ataaactgca tggtgtacag tctagaacac   17640
agtcttagtt tcccacaatt tattaaaccc caaagaaaga aaagatggga gaggaatgca   17700 cttttccttta actcccttca caaactggtg aatgatgaca cccaatgatg actacaacat   17760
tctcaaatga gggaaattaa acgaagaag aaaaaaaaac tggccctacc aaaagctttc   17820
acaactaggg acttaacctg aaaaacgaga ttttgttgtt gttgtttgag atggaatttc   17880
gttctcgttg cccaggctgc agtgcaatgg cgtgatctca gctcactgca acctccgcct   17940
cccgggttca gcgattctc ctgtctcagc ctcctgagta gctagattac aggtgcccgc   18000
cactatgccc agctaatttt tggtattttt agtagagatg ggttttcaca acatgttggc   18060
gaggctggtc ctgaactcct gacctcaggt gatccgcccg cctgggcctt ccaaagtgct   18120
gggattacag gcatgagcca ccacgcccgg ctgagatttt ttatagatag gatttttaa   18180 gagaatgcag gacaggacta acaaaaagaa aaaagaaat acccctctac tccacacgag   18240
ttattaagaa attattttag gcaaatggag aggaaaagtg gtccttggaa ggttttttcgt  18300 agctccagaa aaatttcttg tctagcataa aagccctggc tcttaaaggc tggcaacctt   18360
taagatgcaa atgcaagagg gtccacccaa catggcgatt cccaccgttg tcctcttgcc   18420
cttgctccat caggtaccta acagcatggc cgcccccaca taaccccgtg tgtaaaatgt   18480
catggcatcc tgcatttgtg tattaaagga ctggggtggg agggccagtt ttcttgaggg   18540
ctaaatgaca tgcctggtca aaccaatcct ctgagcccta tgcaaataag acaccacccc   18600
ctccagccgt cacataaaac tggctagtat tgtcagaatg taaggtctcc tctttcagct   18660
ttagagcccc cctccctctg tctgtgtaag ggggagcttc ttccttctgc cttctcccctt   18720
```

```
cttgcctatt aaacgctctg ctccttaaaa ccactccacg tgtgtccgtg tcgttttatc   18780
taattcaact caaaacaaaa aacctggtgt tcctctactc ctcaaagcca tatcagtaac   18840
aaggcagtgt cccaggtaca aagcaggaac aaggactcta aatatcattc agctagaatt   18900
ctgatataac tttaacaaaa actatacatt aaatagggt ccgggcaggt ggctcacatc    18960
tgtaatccca cactttggg aggccaaggc aggcagatca cttgaggtca ggagctcaag    19020
accagcctgg ccaacatagt gaaaccccat ctctactaaa aatacaaaaa ttagccaggt   19080
gtggtgatgg gagcctgtaa tcccagctac tcaggaggct gagacatgag aatcgcctga   19140
accggggagg tggaggttgc agtgagccaa gattgcacca ctgcactcca gcctgggaga   19200
cagagagact caatctcaat aaataaataa atagggtata ataattctct ttttaaccaa   19260
acttgtaggt tggatactca tcaagtttta attggattca attttatcac atatatttcc   19320
gctcaagagc ctattttttc cactggattt attaaatgtt ttcattttg tcattaatga    19380 tctatctccc aatgaaggca agaaccatat ctaccttgac taccactgta tctgcagtgc   19440
catctcaact gtatggaatt tggtataaac ttaaatatct acaaatgaag aacctgctct   19500
cagactgagc aggagctcat catgccatct agcggtctac ataagtaaca gctccgttag   19560
gtacagtaac tctagagggc aggtatgcgt tcatacaatc actgctttgg aagagaaaaa   19620 aagataaatac aggaagtaac aagaataggt aaaagactag gattactatc acaattggtt   19680
ccacttccta catcttctag agtactatac aatgattact aatacccaga ataatggcca   19740
tgagacactg ccatattacc aaaaaatgta tccaatcctt tggtttccgt gggcgacatt   19800
ggaagaattg tcttgggcca cacataaaat acactaacaa tagctgatga gcagaaaaaa   19860
aattgtaaaa aaaaaaatca taatatttta agaaagtta tgaatttgtg ttgggccaca   19920
ttcaaagcca tcctggcata tggcccacag gccatgggtt ggacaagctt gattaaagac   19980
atacaaaaca aaatattcca tttgtcaagc attcttgtta acaaaaaaat ttttaccaa    20040 acttctttca gtgacatctc ttaagaaatg ctgctcacta atattttgga agtctgtatt   20100
agtaatgaga aagtactgat actctcccgt catccatgca ataataaacc tgcattttt    20160 tttttttttt ttgagatgga gtctcgctct gtcacccagg ctagagtgca gtggcacaat   20220
ctcagctcac tgcaacctcc aactcctggg ttcgagcgat tctcctgcct caggccccca   20280
agtagctggg actgcaagca tgcgccacca cgcctggcta attttgtat tttcagtaaa    20340 gacatggttt catcttgttg gccatgctgg tcttgaactc ctgacctcag gtgatccacc   20400
cgcctcagcc tccgaaagta ctgattacag gcatgagcca ccgcacccag cccagtataa   20460
acctgtattt tacagcataa gtaaatagaa cttacctgat gtctagacct atttggcaaa   20520
tgttaagttc agactatgct gactttttg ctgatggctg taataaaata tatttttact    20580
ctaaatagtc aaatttgcct taaaatgcta aaatatttaa ctgaaccaaa ttttggttt    20640 tgttcctttt ttaaaaagtg taactctcaa attctcaaac aactctatac tccaatttat   20700
ttgactgtac tattggtgca gtggtccaca aatattctct aatacataca gtgacattga   20760
taattactaa tactactact aattttacca ataccggtgt tactccacta ttttccacat   20820
ttctcacaat accttgggtt gaaggtggag atcaatatag tagttttatt ttaaagtaaa   20880 attagcact gtgttttcta tcaatctcgt aagcacatg tacattctat ccgtatcctt     20940
attaggactg ccaggactag actttgaaca gtaagagtct tgccttactt aaaatgagaa   21000
cattaccgga ttcgatggcg tccctgtaga ttcactgcta ctgcttcttt cacaacatat   21060
ctcccttatt acacacagag ccaggctttc atcaaaggaa agggaaatac tatcagattt   21120
```

```
gtggcgtttt ctttgtcgtt caccagataa ttcatctgaa ttttcttctg gatatgtaag    21180 gaaaaaaat  aaattgctgt actgtgattt agaaaattga gctgttttga gtacctattt    21240
gtacagaaac ttagtttcaa taaaattagt tcaaaagtta acactgtttt attgaatctg    21300
tccaactgtt acagcagaac actatctgtg tgtatttatt tatttgttta tttatttatt    21360
gtctgagaaa gggtcttgct ctgtcaccca ggctggagta cagaggcaca atctcggctc    21420
actgcaacct ctgcctcatg ggctcaagtg atcctcccac ctcaacctca gcctcccgag    21480
tagctggtac cataggaacg gtaccatagg aatgcaccat tttgtatttt ttgcatagac    21540
agggtttcac catgttgcct aggctgagaa tactattttt aaaaagcttt ctattcttct    21600
ttcagaactt tatctccata catcacaatt taatctatct aataaagttt ttattaacca    21660
aaaaatctag gattttttt  ctgtcaaaac caaactttaa aatataagag ctcatctgtt    21720
tttttccgaa aagagccaaa gtgtttaatt tactcatatg gtattcttaa tgtttcaatt    21780
tcttcagtac cctacacttt ttcttttgag acagagtcac actcgaccac ccaggctgga    21840
gtgcagtggt acattctcag ctcattgcaa cctctgcctc ccaggttcaa gtgattcttg    21900
tgacttcagc ttccaagtag ctgggattaa aggtgcacac caccatgcct ggataatttt    21960
tgtatttttg gtagagacag ggtttcacca tgttggccac actggtctca aactcctggc    22020
cttaagtgat cctcctgcct cagcctccca agtgctggg  attacaggcc taagccacta    22080
agcccggctc ttcagtaccc tatattttaa acagaaatca aaccagtaa  aaagtttcca    22140 tttcatttta aataataaat tatctctgaa tgggtcagaa tgttagacaa atccgttaga    22200
cataaatgag aatactacct tatactagac ataaaaatga attccaggtg gattaaagat    22260
ctaaatataa agaacaaaac cattcaagta cctataacaa atatattctta taatgctggg   22320 gtggagaagt atttcataat actgcaaagt cctcaataaa aagactatca agattagacc    22380
atgtcaaggt ttacatgaca aaataaaata ccaaacaaaa gttaaaaggc aaaggtcaaa    22440
ttcgaagata atatctgcaa catatatagt aaaaattacc catagtatac atattataca    22500
aagtcctacc aaatcaagat agactgtatt ttcttttaag gaaacaggaa aaagcaagtc    22560
acagaagaaa tacaaatgac taataaacat atgaaaaatc ttgagtcatg tacttgagta    22620
atagaaaaaa aaactcttac ctcctaggga tcaaagaaat gcaaagtgaa atgatatcat    22680
ttttcaccca tgagaatgac aaaaattaaa atgagatagt atcacagatt tctgaaagga    22740
ctttttttat cattttcttg agacaaagtc tcactcttgt cccccaggct ggagtataat    22800
ggcacaatct cggcacactg caacctccac ctcctgggtt caagcaattc tcctgcctca    22860
gcctcctgaa tagctgggac tacaggtgcc caccactgtg cccggctaat ttttttttgta   22920 tttttagtag agacggggtt tcaccgtgtt agccaggatg gtctcaatct cctgacctcg    22980
tgatcctccc tcctcggcct cccaaggtgc tgggattaca ggcgtgagcc actggacctg    23040
gccgggattt ttacgtttta tcgagatcac aagttctgca cgtgagttct taatcatgtt    23100
tgtgttccct atttttaaaa aggtgatctt ggccgggctg caattataaa taatgctgta    23160
attagtatct ctacatataa atctttgaat ttttattac  atccttagga tagattacta    23220
gaaatggagt tactaggata atgttaagaa ctctaagact tttttttctt ttctttttt     23280 ttttttttta agagggagtc tcactctgta ccccaggctg gagtgcagtg gtgcgacctt    23340
ggttcactgc aacctccaca tcccaggttc aagcgattct cctgcctcag cctcccaagt    23400
agctgggatt acaggcgcct gccaccacac ctggctaatt tttgtatttt taatagagat    23460
ggggtttcac catgttggcc aggttggtct cgaactctta acctcaagag atccacccgc    23520
```

```
ttcggccttc caaagtgctg ggattacagg tgtgagccac cgcaccaggc catctaagct   23580
tttttataat ccgaaaaatt taatcaattt ttacccactt ttaccaattt acagaccaac   23640
agtttatcag tgctaataca caagttatta gcactgatga gtaaggatga gtaaaaattt   23700
tatttttact aatttgatag atcaaaagga caccctttg gcattttta ctatctgtaa    23760 agctaaaaat caccaaaatt caccctctcc ccatatttat tagtcattcg tatttactgt   23820
gagaaatttt tgtgaactgt ctgccctttt tgctatttga agttttaatg ttttccttat   23880
tgatttggga agactttta tgtaatacag atattaacag tcaaatttaa agtgactatc    23940
tttcaaatat gttgtattct attttcatt taacttttaa actcatttga aattcatttt    24000
ggcataaggt acagatctaa cttcaccttt tccccaagta actaccattt gttctagttc   24060
cacctctgcc ctagacacct ctgcccttcc tgtcttctgc ccgcatgtac gagattctgg    24120
tctgggttca tttattctgt ttcactgatc tgacattctc tttcatctga atcatacggt   24180
cttagttact gcgacttcct caggcaacag ccttctcgtc tactacgtct actaactgtt   24240
ctcaactatt ttctctctgt caactatttt ctctctctct ctttttttta gacagtctca    24300
ctgtgtcgcc caggcggagt gcagtggcgt gatctcggct cactgtaagc tctgcctccc   24360
cagttcatgc cattctcctg cctcagcctc ccgagtagct gggactacag gcacccgcca   24420
ccacatccag ctaatttttt gtattttag tagagatggg gtttcaccat gttagacagg    24480
atggtctcga tctcctgacc tcatgatcca cccgcctcgg cctcccaaag tgctgggatt    24540
acaggcgtga gccactgcgc ccggccctta tctcttcatt tctaaaatgc tatttacttt    24600
ctgttttaaa actcataggt atgtactacc atttattaaa aataacaatt taaaaattta    24660
actgttaagg tgactaagaa taatggtgaa aatagagttt atatgcctgt ctcctattat    24720
cttttctttt agacgaagtc tcacacggtt acccaggctg gagtgcagtg gcgcaatttc    24780
ggctcactgt aacttctacc tcccgggttg aagtgattct ccttcctcaa cctcctgagt    24840
agctggatta caagtgtgcg ccaccaggcc cagctacttt ttgtatttt tttagtagag    24900 atggggtttc accacgttgg tcaggctggt ctcgaactcc tgacctcgtg atccgccagc    24960
ctcggcctcc caaagtgccg ggattacagg cgtgagccag gcgtgagcca ccacacccca    25020
gccacctcct actatcttaa cagagagttg gctaactata aactccagtg gggcacagta   25080
aactgtgcct gctgtagtca gccagaaaaa tattgctaaa taagcaattt gtaaatcaaa    25140
taaaatcacg aatgaaaaaa actcagaggt taattcatct caaccaaaaa aagggaacaa    25200
tttaattaag tctaaaagca ctaatttcat tagagaaaga atatcaaaaa gctgtgtgaa    25260
tgcgtcaaat aaatattcat atataccgtt ctcactaatt gctctccttc tagatgaggt    25320
agatggtcta gaaaccaaat gtgaagatga aggtttctct tcctgaagct cttgtacaag    25380
gtcctaagca tttaggaaaa aaataaaata caacaaactt aacataacca gtaagctaac    25440
ttgttgtaaa taacctttcc aatttgcaaa taatattaca ttagaatgag aaatttactt    25500
agattacctt ttgatcactc ccaccttcaa ggtgacacct gttctcactc acagatgtac    25560
ctgagtccga tgattctgag agaaaagaaa aaggatcaga aacttggtgg tgggcggggg    25620
gcggcggggc gctactcagt agatatgcta tcagtctaac acaaacccett atgcaattta    25680 acctttcaat aaacattaaa catgtatttt ccaggtggca tcctcatact aaatgttgca    25740
gatgtaaata aaataattca actttaatgt agaagagtaa agtataatca agacattaaa    25800
agactgttag ataaattagc agagagacag gagagtcatt attttggtag ggacagggag    25860
tgtctgagaa acaaagaatc aggaaatatt ttgtaggaca atatgaaaat agggctagga    25920
```

```
aaggccattc cagaccaaga aaacgccatg tgaaaaagta tccaaaagca aactaacaac   25980
agttcctgtt gcaggacacc acaagcagtt cattattact ggaatgtagg caggttcaga   26040
ctgtaaagga tcctgtggtc tagccaaagc aggactcatg ctgtcattcc cttatcactg   26100
cattcttccc cgcagatact tcagaatctt ccttaatgcg atgttgcagc cactcaccat   26160
taaaaaggat ttttgtccaa gaaatgaaac tgatttctag ctcacagaaa atattcatc    26220 cagagagcaa taatgaaccc ctaaatggta attttaagca gaagagtgac aaatcactct   26280
agcaaaacat aagaaaaaga gggcagaggc aggaaaacca gtattagaca attgcaataa   26340
tacaaactaa aaactattaa agcctaaact aaggcatgga aaacaaattc cagagaaatt   26400
aaataggtaa aaaccaacaa gacctggtat ttgatataga aggcaaggaa gaaggagtt    26460 aagatgattc caagattcca acttgggtga ataaatgagt ggtaccattc actaaaagag   26520
aaactttaga aagataaaca gattggatgg gaagataaca aactgagtta ttcaggcaca   26580
taggtttcat ttgtagttgg atatacagac tttgagctca aaagtcaaag tttcagagtt   26640
gggatataca gacaattatc atcaaatacc ctttactacc cccttggaa acattttcat    26700 cttaacagtg aactcatgcc tggacattaa cattttgaaa ttatgcatta tcatagatta   26760
attttctctt tatactatgg gtaaggcatt acactaattt tcttaagttg tacataatag   26820
gttatattgt ccaggaattt tggattagta taaacagatg ctacaaaaaa gatgtaataa   26880
aaaggaagcc ctaggctggg tgggtgcagt ggctcacact tgtaatccca gcactttggg   26940
aggccaaggt gggaggatca cctgaggtca ggagtttgag accagcctgg tcaacatggt   27000
gaaacccttt ctctactaaa aatacaaaaa ttaaccggac gtggtggcag gcacctgtaa   27060
tcccacctac tcgggaggct gaggaaggag aatcacttaa acccgggaag cagaggttgc   27120
agtgatccga gatcgcacca ctgcactcca gcctgggtga cagagtgaga ctccatctca   27180 aaaaaaaaa agtgacaaag ttgagaacat ggaataggag ttctgaagtt aattctactg    27240
atatctaaac caaactcaga ctgcaaataa gtaatttgta agtttccatc tcaataatac   27300 aattttctcta gtaatgtgcc aaagtttatt taaacaaatg aaggaatgaa tacatcaggg   27360
ttacatactt cagaaaactc aaactactac tacaaatact acaattgtat atttagctat   27420
cacacaattt cttaaagagc tttaaaacaa caggtataca tatgtaacca acctgcacat   27480
tgtacacatg taccctaaaa cttaaagtat aataattaaa aaaaaggaa ataaaaagga    27540 tacaatctaa agctcaaaaa aaaaagagc tttaaaacaa taaatgcca aatcatcagc     27600 ctaataacta ctttattt gggataaaat ggagatactt ttctgggctt taaatcctaa    27660
ctttggaaga ataagtattc aattcaacac atttattaaa taccatatta ataaaacact   27720
atagtgtgtg atgcacaatg caaacctgaa taggacacag gtaacaaaaa tataaacaag   27780
tgcaacagcc agacgcagtg gctcatgcct gtaaccccta aactttggga ggccgaggtg   27840
agaatatctc ttgagctcag gtcaagacta gcctgggcaa catagcaaca ccgtctctac   27900
caaacataca gaaaattag ccaggcgtgg tggagcacat ctgtagtccc agcaacttgg    27960
gaggctgagg gggaggatca tttgagccct ggaggtggag gatgcagtga gccaagatta   28020
ccactgcact tcaagcaggg tgacagagtg agagcccatc tcaaaaacaa acaaaaaaac   28080
ccacaagtaa aacaaagcaa ttttacaata aaatctgaat atggaataga ggaagtacaa   28140
gggagtggtc aattcattct aggaactaaa caagctcctg agaggtgttt ttttgttttg   28200
ttttgttttt gtctttttta agagatgagg tcttgctctg tcacctggac tggatggcat   28260
gatcacagtt cactacagtc ctgacctccc agcctcaaaa aatcctcctg cctcagcctc   28320
```

```
ctgagtagct aggactacag gcatgcacca ctataccaag ctgattttg tagttttgc    28380
agagttagga tttgccatg ctgcccaggc tggtcttgaa ctcctcggct caagtgatcc   28440
tcctgcctta gcctcctaaa gtgctggaat tataggcatg agccatcaca cctggcctaa  28500
gagcatttct taactgtagt tcgaggatgg gctttaggag cagtgtagtg tattagagac  28560
agctctaagc agcactcaaa agcaaactgt gagaccgggt gcagtggctc atacctgtaa  28620
tcccaggact ttggaaggcc gaggcaggca gatcacaagg tcaggagttc gagaccagcc  28680
tggccaacat gctgaaaccc cctctctact aaaaatacaa aaattagccg ggcgtggtgg  28740
catacgcctg tagtcccatc tactcgggag gctgaggcag aagaattgct tgaacctggg  28800
aggcggaggt tgcagtgagt cgaaatcatg ccactacact ccagcctgag tgacagagca  28860
agattccttc tcaaaaaaaa aaaaaaaaaa aaagcaaact gtgtacatct cttcccaact  28920
ccatgttttt agccttcaaa tgagagtatt atactatgga agtcagcaag cacataaatc  28980
agggcttttc tcatggaaag taggttgtaa aacacttatt gacttaccca tgtatatata  29040
catgtgcatc tttctggaac aagaacccaa tgctttatc agcttattaa agagagatgt   29100
gacccaaaaa taaccagtta agaaacggaa gtaggaacat aaaattccac ttccacaaat  29160
tggtaaacaa aattttgtct ataaccaaag aaaaagactc atccttcatc cttacacatg  29220
gtcctaccta ggtaacaata ttatttccca agcctttca atacattttc aaggtagatc   29280
actcctaaac aggagctttt gaaattacag acctttcaaa ataaatccta actctgatat  29340
cccaagtcta aattgatcta acaggatatt taacttaca ttagaacctc agtatgtggt   29400
tttagttcat atgtacttct aataaattta tcatactttt attacaatat ttaattaaag  29460
caacttttaa agagaatcac aattataaaa catatgcaca taaacaaaaa tgtctttaaa  29520
acgtttttat ggtatttatc catgatgctc aaaattaact taccctgctg attgactact  29580
accaagttcc tgtagatcat ggtatatatt ttccttgtag acagaaaaaa aaaaaataac  29640
aagagatgta cattttagaa taaaaatttg tattaagctg gatctaacca gacttctaca  29700
tacatactta gtatgaacta ctgcacacat tcaaaaccaa atttatcatt ggcaagcttg  29760
taggcactta aaagcacaat aattagtagc acaatgatta tgtacagcta cttttaataa  29820
ttactaaagt ctctctagct gaaagatttc acactaccaa ttcctgaaat gtgctttgtt  29880
tggactttac cagaagaccc ccaaaaaatg agtatgcaag caggaagagg ttgaacatac  29940
ttattttcaa acaggaatgt ttttagctct gtgcttagta gcaaactgcc aaaaaaaagc  30000
attgagttat gcaaaatcca ttaaatacaa actgccaaaa aaactattga gttacgcaaa  30060
atccattaaa taggaatttg attataatct tgactttcat caagcttcaa cttccttct   30120
tgatcttaaa acgtattaac agaggccggg cgcagtggct cacagacacc tgtaatccca  30180
gcacttcgga aggccgagtc cggcagatca cccgaggcct ggagctcaag accagcctga  30240
ccaacatgga gaaaccccat ctctactaaa aatataaaat tagctgggca tggtggcgca  30300
tgcctgtaat cccagctact caggagactg aggcgggata tcacttaaa cccgggaggc   30360
agaggttgcg gtgagccaag atcacgccat tgcactccag cctgggcaac aagagcaaaa  30420
ctccgactca gggaagaaaa aaagaaaact tattaacaga taaagcagta ctcattcatt  30480
caataaaatac agactgaaaa cctaccacgt accagtcact ggtactatgt accagacacg  30540
ggggaaaaca aagaatgaaa cagaaatgta tatgccctca tgaagtttat atcctaacag  30600
gaggataatt catttacccc agtattcgtt gatgtcacaa tggatttttc cttttgtttt  30660
taaactaagg atttaagaga gtgtttgtca caaaatattg tttctcactc aatattaaga  30720
```

```
ggaaatatga atcccaacta tcttttttca tccttgggaa taaggataca gcaacctaaa   30780
cccacaatat ttttaattca tatccttttc aagtcagtaa tttctcctat ttcttatctc   30840
tcaacattta gaattcaagt ccaaggaaat catacttcca aacattatcc gaagattcaa   30900
tattcagacc aggcacagtg gctcacgtct gtaatcccag cactttggga ggccaagaca   30960
ggcagatcac ttgaagtcag gagttcgaga ccagcctggc caacatgca aaaccccatc    31020 tctactaaaa atacaaaaaa ttagctgctc atagtagtgt gcacctgtaa tcccagctac   31080
tcaggaggct gaggcaagag aatcgcttga acccaggagg cagaggttgc agcctgggca   31140
acagagcaag acttcatctc aaaaaaaaaa gaaaaaaat agaagattca atattcaata    31200
ggtaaagaaa tcaccaatat accaatatag ttatttttaa aatttataaa attaaaccat   31260
atataccaag gccacgtata aaatgacaac atatatggat attaaacaga agtgactcat   31320
caataaaaaa taataattat acatatattt gtaatatata taattatatt atatgtatat   31380
tataatatat aatatacaaa ttataataca aattaagaag ctagatgaaa tttaaatata   31440
gtactatatt cataactagg ttaaaacaca cagttgcaca taatacacaa atgactggta   31500
aaaataccct ttgttaacaa actacagtcc ttttttttcc tttacttttc ttagttttct   31560
gtcatctcct aatgttcaat aataatatat actatgttta caataataag gttgttttaa   31620
agttataaaa tcccttgctc agctgaggaa gttatgtttt ttaataaaat aaaatcccat   31680
ttaattatca tcttttcagc tatactattg agcattaaat actagcagaa gctagttaat   31740
tgtctcaggt gaacgtattc attccattta ttaatgtaat gaatgctaag gctcaacacg   31800
gattgcctgt gctaaaccaa atgtgacaaa gaattccaaa tgtaggccgg gtgtggttgc   31860
tcacatctgt aatcccagca ctttgggagg ccatggcagg tggattaccg aaggttagga   31920
gctcaagacc agcctggtca acatcgtgaa accctgtctc tactaaaaat acaaaaatta   31980
ggcatggcag caggcacctg taatcccagc tactcgggaa gccgaggcag gagaatcact   32040
tgaacccagg agacggaggt tgcagtgagc caagatcatg ccactgcact ccagcctggg   32100
ccatagagca agactccctc tcaaaacaaa caaacaaaaa aaagaataat tttagaaaaa   32160
tatatattaa aaaaattttt ttttcagatg cagttttgct cgttgcccag gctggagtgc   32220
agtggcgcaa tctcggctca cctcaaccac aacctccacc tgcctggttc aagtgattct   32280
actgcctcag cctcccgagt agctggaatt acaggcatgc accaccacac ccagctaatt   32340
ttgtattttt agtagagaca gggtttctcc atgttggtca ggctggtctc caactcccaa   32400
cctcaggtga tccacccgcc ttggcctctc aaagtgctgg gattacaggt gtgagccacc   32460
gcaccaggcc tatttctaga aatattacct gggttaaatt ctgctggtta agtgccataa   32520
tgataggtga caatgaaaat gatctccaaa ataactaagg ctcaaatgta agcctttacc   32580
acgtggtggt atactgtttc tggaataaaa agttataata gctacagcta atacttgaat   32640
gctttgtatg tgcccaaaac tatgcttttt tatacaacgt ctctcttcaa gagctttaac   32700
ctccacatga agtatttaat tatccctatt ttataaatgg ggaagcaggt ttaaaaaggt   32760
taatttatct agtcacaaaa ctagtaaatg attgggctag gtttcaaaca ctggtttata   32820
agatgccaga gctcaggttc tcaaataata tgccgcagag ctaaaaaatt aagtttcagc   32880
atgtctttaa tatgtttcaa cagttttct ctgacaaaag tgaatgaggg tagaggtgaa    32940
ctgaaatgtt agcccagatg gcttttaca atggactaaa ctgaagaatt acctgtgctc    33000
tttcacagag aagcttggca cgccaaacaa atctcctaga agatcatttg aacaatatac   33060
aatatgttgt tgcttctcat catataatcg tttagtcata atatactggc caagataaaa   33120
```

```
aagaacctga aatacaaata tgatttctga gcattaaaga aaactaaatg ttagttgtaa   33180
atacatttaa taatatccta tttatctgaa tagggggtaaa caaccaggaa ccatatccac   33240
aactatgtag aacaaccatt ttgtacttag aagctacttt tggctgggcg cagtggctca   33300
cacctgtaat cccagtactt cgggaggccg aagcggatgg atcacgaggt caggagataa   33360
agaccatcct ggtcccatct ctactaaaaa tacaaaagtt agccaggcat ggtggcagac   33420
acctgtaatc ccagctatta gggaggctga ggcaggagaa ttgcttgaac ccaggaggtg   33480
gaggctgcag tgagccgaga ttgcgccact gcactccggc ttaagcaaca gagtgagact   33540
tcatctcaaa aaaaaaaaa aaaaaaaaa aaaaagctac ttttaagcct tttccattta   33600
atttgacaga agcagaaata actgcttctc tatttactta agcaaacctt aaaatgtgag   33660
gtttttttcc ttgtagactt taactctgcc cagatactta gatactaaca tattaggaag   33720
ggaaaaggca gcaaaataaa aaactgtatag ccaaaaaagt tgcagaaaca aaaatcaact   33780
aaaatatggc agtggtctgg agccacttag taaatagtca taaatactat aaacctcaat   33840
agcctctgag gtcaccagag gaggaagaca gaaaaacaat caatcaatga cagctacaaa   33900
acagtttgag agaattctga gaatgaaata aaccctctaa ggtatcaatt tactccatat   33960
tatgataaat aatcaaaata atgactttga accattaata aaagttaaat tatattccct   34020
gtgctgcatt aagacaagaa gttggcaata cattttaag atatccagat ataaacctat   34080
taacaactac ctaaatacat atggcatttt acagtttaca atgtactttt ataagtatta   34140
tctcattctg atatttcata agattattat cactgtatta gaaatgaaga aattgcgttg   34200
ggcacagtgg ctcacacctg taaatctagc actttaggag gccgaggtaa gcagatccct   34260
tgagcccagg agttccagac cagcctgggc aacatagtga aactccatct ctacaaaaaa   34320
atacaaaaat tagccaggca tagtggtaca agcctgtagt cctagctact gcagacactg   34380
aggtgggagg atcacctgag cccacgaggt ccaggctgca gcgagcagtg atcatgccac   34440
tgcactccag cctgggcaag agagtgagaa actgtcacat aaaaaaaaaa aaaaaaaaa   34500 aaagaagaa gaaactggcc ccagctcttc tgactcttaa tccaacgctc tttttactac   34560
ccatactagc tttcactacc ttcctgtgtg ccccagaaca aagatcctat aactgagaac   34620
tatatcagac aatacataca ctactgttac atagtttagc ataagcattc taagtctttta   34680 tgatggcctt ggccaatttt ctcatttcta tctactgcta aatccatact tttttgtttc   34740
cttaactgat tatccaatga taataaggtc aatcccaaat tagccttaaa aataccatttt   34800 aacctggccc tttcctacaa acactgtctt tggatttaac tggctaagca ggcatcggcc   34860
ttaaaggaat attcttatgt gactgtggat tggacagatt gctgtccagc agtgggaaag   34920
gaaaaaggaa gagaacttag atttattcta ccaaacatcc tttaaggaag tttctaaaag   34980
tatagctgga gaggaaaaag aaaaatgaaa gctcttcctg ccccactata ccgttgtaag   35040
aaagaaactt aaatgttta agtaatctga gtcccataaa ctaagtggga gagacagaga   35100
acaggcatat ttcaatcaca ctgaaattct gcctaaggtt gctcaatctg tcactgaaaa   35160
tcatgcttct gtgcacaaat ttaaaggtgg ggaatgcatt aaaatgctgg aaccattaga   35220
tagaatatat ggtcatgaat cagctcacct ctatcccaga aagatcagta tactgtactc   35280
atgtatctct agtgcagaag ttcttaacct gggatccagg gatgcccaag aagtccttgg   35340
atagaattca gggggtccat taatttggat ggggaaaaaa aaattctatt cttattttca   35400
caaacttcta actagaattt agcttttcct tcgattataa atgtaggcaa caaatcacaa   35460
cagtattaat acctgtgatt tcatcaccaa caaaaatcag aggtgttttc ctatcatact   35520
```

```
gtacttatgg caaacatttc aaaatatgac ttatattcct cactatatca agataatatt   35580
tattggccag gcatggtggc tcatgcctat aatcccagca ttttgggagg ccaaggcaag   35640
tggatcacct gagactagga gttcaagacc agcctggcca acatggagaa acccccatctc  35700 tactaaaaag acaaaaaatt agccaggcgt ggtggcaggt gcctataatc ccagctactt   35760
ggaagggtaa ggcagaagaa gggcttgaat ctaggaggcg gaggttgcag tgagctgaga   35820
tcgtgccact gcactccagc ttgggtgaca gagcgagact tcgtctcaaa aaacaaaaaa   35880
acattatatt tattatatct tcttctaaat cttagtattt attatgttaa taacaaaagc   35940
acacatatca caaactagtt tactattttg gtaaccgtat tttagtatgt ttcctttgta   36000
attctataca ttttatttca tacatttaaa aacatgattc tgggaaggag tctaccaaag   36060
ggttgacagc ataaaatggt caagcaccct tacggggctt ccatttatct gagttcctag   36120
ctgagaaatg aaactcgagt ataattagaa ttttcagctt taaaatatag tccaaacgac   36180
cacaaaatta aatgttgctg cttaatgaaa aatccttcta tatggccaat ttctccacat   36240
ggtcttgaaa actttaagta tggctacatg taactagtga gatactactt atctcttgat   36300
tcagcttacc tctttcatag tataagtgtc tttttgtgca ccaacagact ttaataactt   36360
caaaagcaat ggctttggtc taacctataa agagaaaaga actgctatta tacttccaaa   36420
attatcccag aactataggc cctgcagcaa acatatccat caagttcaat aaaggggatt   36480
tggaaaaaat gctggggagg atcaatcat tatgcaagta tcatggaatc atcaagtatc   36540
agttgtgatc acagacagta tccaatccaa aagagcaaag attactttt cttcagcta    36600 tttatattac ctgcttactg ccttacaaac aaccataaat tactgagatc caatgagctt   36660
accgtactga tccaacgagc ttattgcaag ctaacttaga gaatcaaaga gaatgaata   36720 aatctttaga gtgggtcctg ttatcaatct tctctttcta aagattaggt tcctgaaggc   36780
tagagaacct aactaactaa cccaagctga caagggtaat taagaacaga tcagagataa   36840
caacccaggt ccctcaacta caactcagca ttttcttcct actatatcat gctgcctctt   36900
agttagtcta catttcaaat atctacttga caaacattta ttgagcttct actatgcact   36960
ggacagtggt aggtactgca aaagaaatta caaataagac atatgacctg tatgcaagga   37020
gcctgccaac tagattaggg gtcaattttt ttctgtaaag agccagactg taagtatttt   37080
aagcttttca tacaaatggt tctatccaag taaaaagcat ggctactatg taaaccaacg   37140
ggcatggttg cattccagta aaattttcct tacagaaaga aaggcagctg gctgggagag   37200
gtggctcttg cctataaccc cagcactttg ggagacagtg ctagaggttt gcttgaggct   37260
aggtgttcaa gaccagcctg gccacactg agagactcca cctctacaaa aaaatttaa    37320 aaactaaaac aaaacaggt aacaggccaa agttggctga caggctaaca tttgcctgcc    37380
ccttatctag aggttttaca aatggtcttg agaaaaataa ttgtcatggg ggaggggaat   37440
gtaatatact atgcactttc tcccttcctt ttggtttatc aaaatctgca aaactcaagt   37500
atctttacag cttgccacta ccacacaaac tggtacctct gcacctctct ttaatatgcc   37560
ccggtcctct gtctaacttt aaaatctgac agcaccccca ttggggatgc cttaaaaaca   37620 gattttaaa aattgcctat ttccagctaa tcaataaaac aaatattatt taacaattga    37680
aaaatttaaa atacatatag aattgaatta ttaattttc tgatcacttt tttttttttt    37740
aactgtgctt acatatgcac tttactttca ggctaaagaa tggactctct caaaaaagat   37800
ttaaaaataa cctttttct cctgaatttt tattatatgc tatattagct tcaaattaga    37860
taaaataatt caaagtaaaa atctgtaatg gaagccaggt gcagtggctc aggtctgtaa   37920
```

```
tcccagcact tgggaggcc gaggcaggca gatcacctga ggtcaggagt gtgagaccag   37980
cctggccaac acagtgaaac tccgtctcta ttaaatatac aaaaattacc caggtgtggg   38040
ccaggcgcag tggctcatgc ctttaatccc agcactttgg gaggccaaga caggcagatc   38100
aggaggtcag aagttcaaga ccagcctgga caacatggtg aaaccctatc tctactaaaa   38160
gtacaaaaat tatccgggtg tggaggtggg tgcctgtaat cccagctact cgggaggctg   38220
cggcagaatt gcttgaaccc aggaagcaga ggttgcagtg agccgagatc atgccactgc   38280
actccagcct gggcaacaga ccaagactca gtctcaaaaa aaaaaaaaaa aaaaatctg    38340 taatggaaag ccatcagtat attagtgact taaaagacat gtattaatga gaaaacagct   38400
ataaaagata atagcatttg taatcttaca ttgaagaaca agaaggtaaa ttacaggtga   38460
agatctaaat atttaaaaaa tttaaatcta gaagaaaata taggaatata tttgcaagat   38520
cttgggacag gagagttctt ccaaagcatg atatgaaatt caaaagccaa caaattttac   38580
ttcacagaat tgttctcaat ggggaaaaga caacataaaa ttaaatgcta cattagtaaa   38640
caacaaaagt taaatatact tgaaacacat agagctactc caattactaa gaaaaatttt   38700
aaaaaactaa aaggaaaatg gacagataag actaggcaag tcccagaaga aataaatgac   38760
ttaacaaaat ggaggcctgg tgcagtgatt cacgcctgta atcccagcac tttgggaggc   38820
cgaggcaggc agatcacctg aagttgggag ttcaagacca gcctgaccaa catgaaaaa    38880 ccccatctct actaaaaata caaaattagc tgagcgtggt ggcgcatgcc tgtaatccca   38940
gctactccag aggctgaggc aagagaatcg cttgaacccg tgaggcagag gttgcaatga   39000
gacaagatct cgccattgca ctccagcctg gcaacagga gtgaaactct gtctcaaaaa    39060
aaacaaaaac aaaaacaaaa aggaaaggtg cccagcctca ccaagaaact agagaaaaat   39120
gaatttaaac aatggtacag tacctttttat caaaaaaata gtaataataa taaagaggc    39180 caggcgcagt gactcacgcc tgtaatccca gcactttggg aggccgaggc gggcggatca   39240
ccaggtcagg ggatcaagat catcctggct aacatggtga accccgtct ctactaaaaa    39300 tacaaaaaat tagccgggcg tggtggtggg cgcctgtagt cccagctact cgggaggctg   39360
aggcagggga atggcgtgaa cccggggaac ggagattgca gtgagccgag attgtgccac   39420
tgcactccag cctgggagac agagcaagac tccgcctcaa aaaaataat aataataata    39480 attaaagatt ggtgatattc agtattggca ggagtgaaac tgttagagcc ttttggtgag   39540
caagttacca gtagcaatca aatagtaaaa ttgagaactc aggagttcta attctctaaa   39600
atctttttct tttctttttt ttttttttag acggagtttc gctcttatcg cccaggctgg   39660
agtgaaatgg cgcaatcttg gctcaccgca acctctgcct cctgggttca gcgattctc    39720 ctgccccagc ctcctcagca ggggattata ggcgcgcgcc accatgcccg actaatttt    39780 gtattttag tagagacagg ttttcaccat gttggccagg ctagtcttga actcctcatc    39840
tcaggtgatc ggtccgcctt ggcctcccaa agtgatggga ttacagggt gagccaccga    39900 ggccagccta taattctata aaatctttct tacagaaata gtcacacggg atgcatgtac   39960
aaagcggcac tatctgtaat actcaaaaac aggaggcaat ttttaaaaac ctatcagtaa   40020
aggcataaat aattttttaaa atggtatact catgctgtgg aatactatgc agccattaaa   40080
aagaattctg tagactttat ttattgacaa ggatgcaagt cacagaacaa ctacagtttc   40140
atcttgttag tacaacaaac aggacaataa catagattta aattcaaatg taaatatatg   40200
tgggtacgca cacaaaaaat ctaaaaggaa acatggagca aaaagcctgg aattttcagg   40260
ttttacttta aaatttctct aatgacaaaa atctttaaaa caagcacgaa taactttttt   40320
```

```
gactttttaga aaccattttt aaaaattaaa tactgggagg tcaaaaagga aaaaaaaatc   40380
agtcacgtaa caaacgtaac ttcaaccacg cttaacaatg taatggaact aattttttaaa   40440 gcaaatgtgg caaatggcta aaaaaatact gaccagttct taacagttttt taactccacg   40500 cagttacgcc agaggtagca cactttaagc tatgcacata caatttttatt tacagagcca   40560 tgctacaatt gaggtatacg aaatttagtt tatcacttca taaaataaat tattcttaaa   40620
agttacacga gacaaaaata ctaaccaggg tctcttgttc cgaagctgga atctgtgagg   40680
tggttacagc accatcagta ggtacagaca tgttggtatt gcacatttgc ctacaaggaa   40740
aaaaaagaca cgatgaaaac tggaaatcat gaaacatctg tggaaaatac atcatatata   40800
aagaacataa acaacagtta aaactaaagc tacaagcaag tcggtgctta cctggatcag   40860
cagagaaaaa gtggcgtgcg tccgtgccca caggtctacc ctccaatcgc cactgaacac   40920
agctgggaaa atgcatggtt taaatagccc cagctggaga caagtcagga cttaactcct   40980
tttactgcag tttcggaacg tgtctgaact tgaccagctc aagaggaaaa gctgagtcaa   41040
cctgcccact gaaccggccc aatcccgccc agactacgcg cagcgttcac actagtgacc   41100
cgacaggcac ctgcgatcat ccggacctcc cgcgccaag cggccccgca gccccggcc    41160 cccgtgacct ttaccctgaa ctcccgcgga gacctccgaa ccaccccac ccccaccgcc    41220 gcgagagccg tccgaaatcc cgccctcctc cctggcggcg actgcctagc cccagtccaa   41280
caaaacctcc gcaaagccac gtgccccatg ccccgcgccc cgcgcccga gccccagcc    41340 acgaaccgca caaggctgc gaacgggcag aggctgggaa ccagcgatag aggggacacc    41400
gtcagagccc agacccaaaa gtgaccgctc gctgccgggc cagtacctgc tcctcaccat   41460
ccggggtttt cgcgcttgga gtcggggtc cctcaagact ccccagtttc cttcacgggg    41520
cgcgcggaag cacgacgccc tgggcctcgg ggatcattcc actctccggg ccagggcact   41580
gggcgctcgt acgcactaat ccggggaggg acggtgctcc tggctgcgaa agcagcagga   41640
tctcggtcag aggggtcgcg gccgcccctc gggctcggct tcttgctcca tctttccgac   41700
acacagggcc acacaggccc cagaagcagc caagctcgcc gcggtgcctc ggtgcgcgcc   41760
ccctaccgcc cgaggggagc gcgcgggtcg tcgcggcgca tccgggcatt tgtgcgcgcg   41820
cacacaaccg gccccgcttc cgccaattgg gtccggggct cggccgcacc acctccggga   41880
tgatggagtg gggggtgtcg ccccgcgggc gcggcgggct gtgaggcggg gtggggtgt    41940 tggccgcgag ctgagagggt ggggctcggc ctggcgcgga gccagcaagg tttggcgctg   42000
tgacactcct ttagccgttg cgctatgttt gtatttcttg tgtttacact tcccgcccgc   42060
ggtggaaact gcgacaaatg cggatctccg tgtcgctgtt accaaaaaga aaccaaaatt   42120
aacagctgtt taatatatta agcccactcc accagccgct ggagttgtac ccaaatgagt   42180 tatttttaagg cctgttttta aaaaagatta aaaatagcac ttaaggcagg cttatacacc   42240
ggtgcataca gctgttctgg ttggagaacg aagatgctgg ttaccgttgg cggggagggg   42300
agcggttact ctgcgctttt agaatgtttg ggtttggctg ggcgcggtgg ctcacgcttg   42360
taatcccatc actttgggta ggccgaggcg ggtggatcac ttgaggtcag gagttcaaga   42420
ccaacctggc caacatggga aacgccgtct ctactaaaaa ctacaaaaat tagtcgggcg   42480
tggtggcggt cacctgtaat cccagctact ctactccgga ggctgaggca ggacaatcct   42540
gtgaacccgg gaggcagagg ctgcagtgag ccaagatcat gccattgcac tccagcctgg   42600
gcgacagggc aagactctca aaaaacaaa acaaagtttt gggtttgtta atctacacat    42660
tcattatcat taaaatatat acttatatat tatgcactca ttctgactca cctactttcc   42720
```

```
cacagagatg tggcaaaaac gtttttgatg cggtctcata aattgaggac ataaagaatt    42780
gagttagcta aacccaaaaa cacagccatt gcaaagaagg aacacgtttc ttctctggcc    42840
agtaagtgat tagctccttg tgaacaagga cctttttta taaagttata tccttcccctt   42900 ctgcagcttt ttttttttta taaagttata tccttcccct ctcccgcttc ccagcctacc    42960
agaaaggaaa cttccttaaa catagtggtc actcagttga tttaagttga ttgccaatat    43020
tattaactta agagatttaa tatgtggctt ttaaaaagat aatctcatct tcatcagatc    43080
atatacagtg gggtttctaa tagactcagt gcttgaccct ggatgaaaga aaatctcaag    43140
cagtgagaaa atgtaagcat gaaaagataa gtgataggct gcgcacggtg gctcacgctt    43200
gtaatcccag cactttggga ggctgaggtg ggtggatcac gaggttagga gttcgagacc    43260
agcctggcca agatggtgaa accttgtctc tactaaaaat acaaaaatta gccgggcccc    43320
gtggcgggcg cctgtaatcc tagccacttg ggaggctgag gcagaagaat cgcttgatct    43380
cgggaggcag aggttgcagt gagcggagat cgcgccactg cagtccagcc tgggtgacag    43440
agcaagactc catctcagaa gaaaaaaaaa aaaaagaga taagtgatag aggttgatat    43500
ttgttaaata tcaagtgaac gaatgggttt gtgctataaa agttcagaga cagaattaat    43560
tgcttagtaa atgctggagg cagttcacaa aggcctcaga gatcacacat attttgtgtc    43620
ttgaaagatg gtgagactta aataaaagca gagaatattc caggcacaag aaaattatca    43680 aaaatacag aaggaaaat ataagaggac tgtttgagat acaataaata aatccgtttg     43740
acttgcatga aagtcaagaa gaagttttaa gaacttggag tctccttaaa tgccaagcaa    43800
ggaaatttgg gctttcgaca gagtagacat tagaagcata aaaacaagtg atttgcttca    43860
aactgtattt taacaggacc accaagagta gattcaaact cagaatagtc gggccggctg    43920
ccttctggac cgactttccc ccttctcatt ggccttgtgc tttgaaaaaa ttatcttgac    43980
aaaattatta gagcagaaaa aaaaaggcag aactgataag attagtccctt ttctaatgga    44040 accagaaaag aagggtcaga aatgaaggca gaagggagaa gcgggggtgg gggagagaga    44100
gagaagtaaa aaggattcac tcaagaacct ggtattcaaa actacgtgta ccagcactac    44160
cacagcagta tgactcagtg tccacctaaa gcatgatgat actgcttacc aaaaaaagtc    44220
tggagggaat gaaagttgg gttagttta agttatgggt cacagaacag aattcggtgg      44280
taaaaagctt aggctgggaa cagagcttga aacagcaaag gaatgagagg aacgaccaaa    44340
aagccaagga ccatatagtg atgtctgaaa aatcagaatc aggtaataat attgaatact    44400
gcaaaagtca gagaaaatgt ggaaataaga aagcaagcga tctggaaagt ggcgagtaag    44460
atggaatatg aggaggttgc tgagagctgg gaggagacgg cagacagcgg ggaaatagac    44520
gtctggaaaa aaaactgaag atcacacaga aagcaggaaa ttcaaatctc ccaaagtgcc    44580
cattgtgatt caggatgata atttccccc gggaccccct ccacaggtcc gcatcctcaa      44640
gaggcccacc agcaacggtg tggtcagcag ccccaagtcc gctagcaggc ccgcccttcc    44700
agtcaagtcc ctggcacagt gggaagccga gtacaccgag gccaggaagc ggatcctggg    44760
cagcgccaac ccgaggagaa gcaggagaaa cccatcctcg ataggtcttc ctctgatctt    44820
cttcccttca ggccaaccag gatctcctaa cccgaagaca gcagacagcc caataatgtg    44880
atcagacagc ctctgggtcc tgatgggtca cacggcttca aacagcgcag ataaatgcag    44940
gcaagaagag atggcgcgac tgccgcgtca acgcgtcctg ggtcgtccgc caagggttgc    45000
actaccgtgg cagacagctg gacttgagca gcgggaactt gacttacttg cctggtgatc    45060
cccgttgctc cgcccactgt gaccttgaat cccatgcact gtgacctccc cccttctcct    45120
```

```
ccttcccact gtgattggca ctttgacaag gactgtccca agtcaatgga aagggaaaaa    45180
gggtgagggt taggagaagg ttgggggaa  cccaccaatt actcagagta gagagtcaga    45240
cagggccagc aatagcggtt tatcatgctc attaatttgg gatttcaaaa cacaaatgaa    45300
ctcacaccta cccacccca  agtgcatgtc atcacttaaa aagtgagttc catttgaaaa    45360
aaaagaaagc aaactacctg ctcactctaa aagcagttgc tgttgtttgt gactttgcca    45420
tttaaaaaaa tacagaccag ctgctgctgt ttgcttgcat tccacagtta tcttgtgtca    45480 cttttgccctt tgttgtgctt acttgaagtt tctctagagg caaactgctt atttctagta    45540
gcgttgttct tgatgcccaa gaggtgttcc aagaggttga gatactttga gtgtctttat    45600
attctctggg acctaaactc tgcaaacaag gctcacacct gtaatcccag cactgtggga    45660
ggccaaggct ggaggatcta ttgaggccaa gagtttgaga ccagcctgag caacatggcg    45720
aaaccctgtc tctataaatt gcaaaaaaaa attagccagg cgtggtggca ctcacctata    45780
gtcctagcta cttgggagcc agagctggga ggatggcttg agcccggata ggttgtggtg    45840
tgatcctgcc actgcactcc agcctatgtg acagagtgag accatgtctc aaggggaaaa    45900
aaaaaagtct acaacagact tatcttgacc caagggccac ttcgtacttg tatttattag    45960
tcataactaa tcttttgtct ttctttttt  tttttttg   agacggagtc tcactctgtc    46020
acccaggttg gagtgcagtg gcacgatctc agctcattgc agcctccacc tcctgggttc    46080
aagtgattct cctgcctcag cctcccgagt agctgggatt acaagcttgt gccaccatac    46140
ccggctaatt tttgtatttt tagtagagac gggatttcac tatgttggcc aggctggtct    46200
cgaactcctg gcctcaggtg atccacccgt ctcaccctcc caaaatgctg ggattacagg    46260
cgtgagccac tgtgcctggc cacaactaat cttaaagca  tggtgaaaac taaacaagat    46320
ttagctcaga aaccgtgttt agaatgctga gtttcacaat atttatgaga ccatctaaaa    46380
ttacagaagt agttcaaatt ccttatgtct ttccaaacat ctggaactga atagtgttat    46440
ttaaaaggca aaatccgggc cggacgcagt ggctcacgcc tgtaatccca gtactttggg    46500
aggccaagac aggcagatca ctgaaggtca ggagtttgag accagcatgt aaaacccgt     46560 ccctgctaaa aatacaaaaa ttaggcgggc atggtggtgc aagcctgtaa tctcagctgc    46620
tcggagggct gaggcagcag aatctcttga acctgggagg cagatgttgc agtgagccga    46680
gatcgcgcca ctgcactcga gcctgggcgg cagagcaaga ctctgtcctg gaaaataaaa    46740
aagtaaaaaa taggccgggc atggtggctc atgcctgtaa tcccaccact ttggcagggt    46800
gaggcgagtg gatcacctga ggccaggagt tcgagaccag cctggccagc atggtgaaac    46860
cctgtctcta ctaaaaatac aaaaaattag ccgggtatgg tggtgcacgc ctgtaatccc    46920
agctactcca gaggctgagg caggagaatt gcttaaacct gggaggcaga gatcatgcca    46980
ctgcgctcca gcctgggaga cagagtgaga gtgagactcc atctcaaaaa ataaataaat    47040
aaataaagta aaaataaaa  agcaaaatcc cagcaagtag tgaatacaaa gactttttgt    47100
ttttactttg aaaattaatc aacttttttgt ttgactgaaa catacagaaa cattcacaga    47160
acaattaata ttcaacaaaa gaaaccaccg cctcaagttc ttctgctctg aagaacaaaa    47220
aaagaaaaaa agaaaccact acccagaatt cacatttgtc attcctgcat caaacatatt    47280 tttttatta  tttatttatt tattttgaa  acagagtctt gctctgtcgc ccacactgag    47340
tgcagtgagc caagattgta ccactatgcc tggctaatct ttagtatttt tagtagagat    47400 gggttttac  catgttggcc aggctggtct caaactcccg acctcaagca atccacctgc    47460
cttggcctcc caaaatgcta ggattacagg tgtgagccac tgagcctggc ctaaataaat    47520
```

```
tttttaatg aaacattgct taaaaaatta aaatttcact gttattcttt atcccattcc    47580
cctcccttct cttgataatg atcaatttga tgcctgtcca ctaagtctgt gttttataca    47640
ttcactgtaa atttatgaat ccataaacaa cacggacagt aggctgcata cctataagag    47700
gacttgctgg gcaacagaat agtaaaacctt agagtaagtt tcaatatgta acaggaaaag    47760
ctctctttat cttttttcagt attgttttgg ctcttcctgg atgttaactt ttagaaccag    47820
tttgtctaat tcacaaaaag aatcctcttg ggattttgct tttcattgca ttggattgtt    47880
agactaattt gacttatttt cagtatgaat tcttcccaga taagaacatg atatatcact    47940
ccatttttag gtctctctta acatccttta ataatgcttt attgtttcct ccttaaagct    48000
gttgtatgtt tggctggctt ttttctgaag tgcttttataa gttttattgc tgttttttaaa   48060 ttacaccttt taaaatttttc ttttcttttt ttttgagatg gagtttcgct ctgtcaccca    48120
ggctggagtg cagtggtgcg atcttggctc actgtaagct ccgcctcccg ggttcatgcc    48180
attctcctgc ctcagcctcc ggagtagctg ggactacagg cgcctgccac cacgcccggc    48240 tattttttttt ttgtattttt agtagagaca aggtttcacc gtgttagcca ggatggtctc    48300
gatcttctga cctcgtgatc cgcccacctc ggcctcccaa agtgctggga ttacaggcgt    48360
gagccaccat gcccagccgt aacatttttat tttctatttg gttattgcta acatatgaaa    48420
caattactca ttttttgtgtt ttgatcttat agccagccag caatactgct tttttgttct    48480
ttctgttttt gttttttgtt tttgggtttt tttttgagac ggagtctcac tctgtcaccc    48540
agacgggagt gcagtggcac aatctcggct cactgcagtg tctgcctccc tggttcaaag    48600
gattcttctg ccttagcctc ctgagtatct ggcactacag gtgcgtgcca ccacacctgg    48660
ctaattttta tattttttact agagatgggg tttcgccatc ttggccaggc tggtctcgaa    48720
ctcctgacct cgtgatccac ccaccttggc ctcccaaagt gctgggatta caggctgtat    48780
tttgttttgt tatacagtac tattagtttt tcagtagatg ctcttggatt ttctatgtta    48840
ataatatcat atgcaaaaat cactaacttg tctcttcctt aaacctcttt ttcattttct    48900
tacaaccatt ggaatggaat agtagcaatg atagtgggca tcctcatctt attcatgaca    48960
ttagtaaaaa tgcttttaaa atgtgatgtt tgctgtaaat tttaggtaga tgctctttat    49020
tacataaaag tttccttcta ttcctggttt tttgagctta taaaaagta tgaatcagtg    49080 ttcagtttta tacactgctt ttttatgcac ctagaaatga ccctgtggct tttctccttt    49140
aatctgtcta tgtggtgaga ttatattgat agatttccaa tattgacctt ccttgtttta    49200
ctcagataaa attctactta gttacaatag atctcttttt ttggacattt atgaactgaa    49260
tttttaagag gaaaaatatt acacaatgat atgggagcat aattgagttc ctgctcttag    49320
aagataacaa atatttcaga gattttagta ggaatattgc cctgttaaga acgctcaatt    49380
ctctaaagct aagttcaaat aaggcccaat tcttggcctg agactctggt tcccacaagg    49440
gcaatacagg ctgaactggt tgataaactt ttaccattga gagttttttt tttctttttg    49500
agacggagtt ttgctcttat tgcccaggct ggagtgcaat ggcttgatct cggctcagtg    49560
caacctccgc ctcccagata caagtgattc tcctgtctca gcctccgaag tagctcagat    49620
tacaggcatg tgccaccaca cccagctaat ttttttgtatt tagtagagac atgtttcatc    49680
atgttagtca ggctggtcgt gaactcctga cctcaggtga tccacccgcc tcagcctccc    49740
aaagtgctgg gattataggc gtgcgccact gcacccggcc acgtttaaga gttttaagga    49800
aggaccagga ataatagagg tcatcttttc gtggaacgaa gagtttataa tctcccagct    49860
gacctaaatc tgagatctgt gatcgtatct agtctgaaag ttacagagcc attcagctgg    49920
```

```
cagaagaaag gtagtgaagt tgaacagcat ccccactctt tggggtggaa aggttgctgg   49980
agtttccccc agattaagtg gttcctggag aagatggaag gagtataagc agttctgctg   50040
gtaactccta aaatggccac tacctgggta atagaaccct ggaagcaaaa gacatagaat   50100
atctattggt agaatgtgct ggactaggga gaaagaagtt gagcttcatt catataccccc  50160 tgctcaactt cctaccagga ccatgccacg agtctttctg gagaaatatc atttggacac   50220
ctgccagatg aagagaactg gtggtcaatt ggtaataatc agagaaactg ggacaaccaa   50280
cagaaaggga cagaaatgtt tcccatgatc tagttgaggt tgttcataca atgaaccaca   50340
gttatgtcct gctaataaaa gggcaactaa ttttgaaggg caattatgta aagaaatgta   50400
attttcctct ccttcctcct tgccacccca actggtatcg ggatggcagg agtcatgtgt   50460
ggttttctat ggctgtgtaa caaattacca taaatgtagt agcttaaagc aacacaaatt   50520
attagctcac agtccatata tcagaaatcc aggtaggctc acctggttcc tctgctccag   50580
gtgtcataaa gcctaaatca aggtgtgggc cagcttgggc tcttaaggat ctagggaaga   50640
acctgctttc tagcttattc aaattgtcag ccaaattcag ttccttgtgg ttgtaggacg   50700 gtagtccccct ttttcttgct agcagtgagg accactctca gctcctgaag gcttcctgca   50760
ttccttgcta cacactcccc tccatcttca agccagcaac agggtgttga atcacccttg   50820
tgctttgaac ctgacttact ctcctgctat cagccagaaa aaaactctga cttcaaaggc   50880
tcatgtgatt tgatgaggcc aacccagatc atctccctttt tgccatgtaa tgtaacagaa   50940
tgatgggagt aatatctcct catattcaca ggttcctccc acgcttaaag gggaggggat   51000
catccatagg caaggtcact gggagtcatt cttggaatt                         51039
```

ISOLATED GENOMIC POLYNUCLEOTIDE FRAGMENTS FROM CHROMOSOME 12 THAT ENCODE HUMAN MOUSE DOUBLE MINUTE 2 HOMOLOG

PRIORITY CLAIM

This application is a continuation application of application Ser. No. 10/608,403, filed Jun. 27, 2003 under 35 USC §120, the contents of which are incorporated herein by reference.

FIELD OF THE INVENTION

The invention is directed to isolated genomic polynucleotide fragments from the human chromosome 12q13-q15 region that particularly encode human carboxypeptidase M and human mouse double minute 2 homolog, vectors and hosts containing these fragments and fragments hybridizing to noncoding regions as well as their reverse complements t. The invention is further directed to methods of using these fragments to obtain human carboxypeptidase M and human mouse double minute 2 homolog and to diagnose, treat, prevent and/or ameliorate a pathological disorder.

BACKGROUND OF THE INVENTION

Chromosome 12q13-q15 contains genes encoding, for example, interleukin 22, a protein tyrosine phosphatase, interferon-gamma, carboxypeptidase M and the human mouse double minute 2 homolog; the last two of which are discussed in more detail below. The chromosome 12q13-q15 region is known to be aberrant in tumors such as sarcomas (Oliner et al., Nature 358: 80-3, 1992).

Human Carboxypeptidase M

Human carboxypeptidase M is a cell membrane-bound basic carboxypeptidase believed to act by activating, inactivating and modulating excitatory peptides such as the anaphylatoxins and kinins (Tan et al., J. Biol. Chem. 264: 13165-70. 1989). Its expression is increased as monocytes differentiate into macrophages (Rehli et al., J. Biol. Chem. 270: 15644-9, 1995). It is also widely distributed as an ectoenzyme of specialized epithelia and endothelia. Its ability to convert anaphylatoxins to their less active C-terminal des-Arg forms protects against complement-linked tissue damage.

Human Mouse Double Minute 2 Homolog

Human mouse double minute 2 homolog plays a key role in modulating actions of p53 (Oliner et al., supra), in part by targeting p53 for destruction (Ries et al., Cell 103: 321-30, 2000). Over-expression of this oncogene increases tumorigenic potential. The human mouse double minute 2 homolog is over-expressed in both sarcomas and some leukemias. In addition to its ability to in effect neutralize p53, it reacts also with a retinoblastoma protein.

SUMMARY OF THE INVENTION

The invention is directed to isolated genomic polynucleotides, said polynucleotides obtainable from the human chromosome 12q13-q15 region having a nucleotide sequence at least 95% identical to a sequence selected from the group consisting of:

(a) a genomic polynucleotide encoding a polypeptide selected from the group consisting of human carboxypeptidase M depicted in SEQ ID NO:1 or human mouse double minute 2 homolog depicted in SEQ ID NO:2, or variants of SEQ ID NOS:1 or 2;

(b) a genomic polynucleotide selected from the group consisting of SEQ ID NO:3 which encodes human carboxypeptidase M depicted in SEQ ID NO:1 and SEQ ID NO:4 which encodes human mouse double minute 2 homolog depicted in SEQ ID NO:2, or variants of SEQ ID NOS: 3 or 4, (c) a polynucleotide which hybridizes to any one of the polynucleotides specified in (a)-(b) and (d) a polynucleotide that is a reverse complement to the polynucleotides specified in (a) to (c) as well as nucleic acid constructs, expression vectors and host cells containing these polynucleotide sequences.

The invention further relates to a polynucleotide comprising:

(a) a genomic double stranded polynucleotide set forth in SEQ ID NO:3 encoding human carboxypeptidase M set forth in SEQ ID NO:1 and the polynucleotide set forth in SEQ ID NO:4 encoding human mouse double minute 2 homolog set forth in SEQ ID NO:2;

(b) a polynucleotide that hybridizes to one strand of the polynucleotide of (a) and (c) a reverse complement of (a) and (b).

as well as nucleic acid constructs, expression vectors and host cells containing these polynucleotide sequences.

The polynucleotides of the present invention may be used for the manufacture of a gene therapy for the prevention, treatment or amelioration of a medical condition by adding an amount of a composition comprising said polynucleotide effective to prevent, treat or ameliorate said medical condition.

The invention is further directed to obtaining these polypeptides by (a) culturing host cells comprising these sequences under conditions that provide for the expression of said polypeptide and (b) recovering said expressed polypeptide.

The polypeptides obtained may be used to produce antibodies by (a) optionally conjugating said polypeptide to a carrier protein;

(b) immunizing a host animal with said polypeptide or peptide-carrier protein conjugate of step (a) with an adjuvant and (c) obtaining antibody from said immunized host animal.

The invention is further directed to a nucleic acid molecule or reverse complement thereof comprising a sequence of nucleotides which specifically hybridizes to noncoding regions of said polynucleotide sequences of SEQ ID NO:3 (human carboxypeptidase M gene) or SEQ ID NO:4 (human mouse double minute 2 homolog gene). These sequences may be used to modulate levels of human carboxypeptidase M and human mouse double minute 2 homolog in a subject in need thereof and specifically for the manufacture of a medicament for prevention, treatment or amelioration of a medical condition. As defined herein, a "polynucleotide fragment" may be a nucleic acid molecule including DNA, RNA and analogs thereof including protein nucleic acids and mixtures thereof and may include a probe and primer. Such molecules are generally of a length such that they are statistically unique in the genome of interest. Generally, for a probe or primer to be unique in the human genome, it contains at least 14 to 16 contiguous nucleotides of a sequence complementary to or identical to a target sequence of interest. These polynucleotide fragments can be 20, 30, 50, 100, 150, 500, 600, 1000, 2000 or more nucleic acids long. Probes and primers may also be referred to as oligonucleotides. As defined herein, a "reverse complement" is a molecule encoding a sequence complementary to at least a portion of an RNA molecule or to a genomic DNA segment and may be used interchangeably with "antisense oligonucleotide". The sequence is sufficiently complementary to be able to hybridize with the RNA or DNA, preferably under moderate or high stringency conditions to form a stable duplex or triplex. A "reverse complement" also includes peptide nucleic acid reverse complement sequences.

The invention is further directed to kits comprising these polynucleotides and kits comprising these sequences. In a specific embodiment, the sequence(s) are attached to a substrate. In a specific embodiment, the support is a microarray. The microarray may contain a plurality of sequences hybridizing to non-coding sequences. As defined herein, a "plurality" of sequences is two or more sequences. Alternatively, the microarray comprises non-coding sequences as well as coding sequences.

In a specific embodiment, the noncoding regions are transcription regulatory regions. The transcription regulatory regions may be used to produce a heterologous peptide by expressing in a host cell, said transcription regulatory region operably linked to a polynucleotide encoding the heterologous polypeptide and recovering the expressed heterologous polypeptide.

The polynucleotides of the present invention may be used to detect a pathological condition or susceptibility to a pathological condition in a subject comprising
  (a) isolating genomic DNA from said subject;
  (b) detecting the presence or absence of a variant in said genomic DNA using a probe or primer derived from a polynucleotide hybridizing to non-coding region(s) of a human carboxypeptidase M gene and human mouse double minute 2 homolog gene; and
  (c) diagnosing a pathological condition or susceptibility to a pathological condition based on the presence or absence of said variant.

Probes or primers derived from SEQ ID NO:3 (human carboxypeptidase M gene) or SEQ ID NO: 4 (human mouse double minute 2 homolog gene) may be used to identify variants including but not limited to mutations, duplications, translocations, polysomies and mosaicism on the human carboxypeptidase M gene or on the human mouse double minute 2 homolog. Therefore, the invention is also directed to a method for identifying variants of SEQ ID NO:3 and 4 comprising
  (a) isolating genomic DNA from a subject and
  (b) determining the presence or absence of a variant in said genomic DNA using the probes or primers.

DETAILED DESCRIPTION OF THE INVENTION

The invention is directed to isolated genomic polynucleotide fragments that encode human carboxypeptidase M and human mouse double minute 2 homolog, which in a specific embodiment are the human carboxypeptidase M and human mouse double minute 2 homolog genes, as well as vectors and hosts containing these fragments and polynucleotide fragments hybridizing to noncoding regions, as well as antisense oligonucleotides to these fragments.

As defined herein, a "gene" is the segment of DNA involved in producing a polypeptide chain; it includes regions preceding and following the coding region, as well as intervening sequences (introns) between individual coding segments (exons).

As defined herein "isolated" refers to material removed from its original environment and is thus altered "by the hand of man" from its natural state. An isolated polynucleotide can be part of a vector, a composition of matter or can be contained within a cell as long as the cell is not the original environment of the polynucleotide.

The polynucleotides of the present invention may be in the form of RNA or in the form of DNA, which DNA includes genomic DNA and synthetic DNA. The DNA may be double-stranded or single-stranded and if single stranded may be the coding strand or non-coding strand.

The genes encoding human carboxypeptidase M and the human mouse double minute 2 homolog are disposed in the chromosome 12 genomic clone of accession number AC025423, 150579 base pairs, at, respectively, nucleotides 1-99860 and 99541-150579.

The polynucleotides of the invention have at least a 95% identity and may have a 96%, 97%, 98% or 99% identity to the polynucleotides depicted in SEQ ID NOS:3 or 4 as well as the polynucleotides in reverse sense orientation, or the polynucleotide sequences encoding the human carboxypeptidase M or human mouse double minute 2 homolog polypeptides depicted in SEQ ID NOS:1 or 2 respectively.

A polynucleotide having 95% "identity" to a reference nucleotide sequence of the present invention, is identical to the reference sequence except that the polynucleotide sequence may include, on average, up to five point mutations per each 100 nucleotides of the reference nucleotide sequence encoding the polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence, the ORF (open reading frame), or any fragment specified as described herein.

As a practical matter, whether any particular nucleic acid molecule or polypeptide is at least 90%, 95%, 96%, 97%, 98% or 99% identical to a nucleotide sequence of the presence invention can be determined conventionally using known computer programs. A preferred method for determining the best overall match between a query sequence (a sequence of the present invention) and a subject sequence, also referred to as a global sequence alignment, can be determined using the FASTDB computer program based on the algorithm of Brutlag et al. (Comp. App. Biosci. (1990) 6:237-245). In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identify, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total numbers of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for purposes of the present invention.

A polypeptide that has an amino acid sequence at least, for example, 95% "identical" to a query amino acid sequence is identical to the query sequence except that the subject polypeptide sequence may include on average, up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the referenced sequence or in one or more contiguous groups within the reference sequence.

A preferred method for determining the best overall match between a query sequence (a sequence of the present invention) and a subject sequence, also referred to as a global sequence alignment, can be determined using the FASTDB computer program based on the algorithm of Brutlag et al. (Com. App. Biosci. (1990) 6:237-245). In a sequence alignment, the query and subject sequence are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter.

If the subject sequence is shorter than the query sequence due to N- or C-terminal deletions, not because of internal deletions, a manual correction must be made to the results. This is because the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/ aligned with a corresponding subject residue, as a percent of the total bases of the query sequence. Whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of the present invention. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence.

The invention also encompasses polynucleotides that hybridize to the polynucleotides depicted in SEQ ID NOS: 3 or 4. A polynucleotide "hybridizes" to another polynucleotide, when a single-stranded form of the polynucleotide can anneal to the other polynucleotide under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions, corresponding to a temperature of 42° C., can be used, e.g., 5×SSC, 0.1% SDS, 0.25% milk, and no formamide; or 40% formamide, 5×SSC, 0.5% SDS). Moderate stringency hybridization conditions correspond to a higher temperature of 55° C., e.g., 40% formamide, with 5× or 6×SCC. High stringency hybridization conditions correspond to the highest temperature of 65° C., e.g., 50% formamide, 5× or 6×SCC. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA.

Polynucleotide and Polypeptide Variants

The invention is directed to both polynucleotide and polypeptide variants. A "variant" refers to a polynucleotide or polypeptide differing from the polynucleotide or polypeptide of the present invention, but retaining essential properties thereof. Generally, variants are overall closely similar and in many regions, identical to the polynucleotide or polypeptide of the present invention.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5-10, 1-5, or 1-2 amino acids are substituted, deleted, or added in any combination are also preferred.

The term "variant" also encompasses allelic variants of said polynucleotides. An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene. The term "variant" also encompasses naturally occurring variants such as single nucleotide polymorphisms (SNPs).

The amino acid sequences of the variant polypeptides may differ from the amino acid sequences depicted in SEQ ID NOS:1 or 2 by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, The Proteins, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, as well as these in reverse.

Noncoding Regions

The invention is further directed to polynucleotide fragments containing or hybridizing to noncoding regions of the human carboxypeptidase M or human mouse double minute 2 homolog genes. These include but are not limited to an expression control element, an intron, a 5'-non-coding region, a 3'-non-coding region and splice junctions (see Tables 1-2, as well as transcription factor binding sites (see Table 3). The polynucleotide fragments may be a short polynucleotide fragment which is between about 20 nucleotides to about 50 nucleotides in length. Such shorter fragments may be useful for diagnostic purposes. Such short polynucleotide fragments are also preferred with respect to polynucleotides containing or hybridizing to polynucleotides containing splice junctions. Alternatively larger fragments, e.g., of about 50, 150, 500, 600, 2000 or about 5000 nucleotides in length may be used.

TABLE 1

EXON/INTRON ORGANIZATION OF THE
HUMAN CARBOXY-PEPTIDASE M GENE
(cDNA ACCESSION NO. XM_006768)
IN SEQ ID NO: 3,99680 BASE PAIRS;
NUCLEOTIDES 1-99680 IN THE GENOMIC
CLONE OF ACCESSION NO. AC025423
(FORWARD STRAND CODING).

| EXON | NUCLEOTIDE NO. | AMINO ACID NO. |
|---|---|---|
| 1 | 16641-16796 | 1-52 |
| 2 | 63585-63686 | 53-86 |
| 3 | 77522-77692 | 87-143 |
| 4 | 79077-79262 | 144-205 |
| 5 | 79982-80152 | 206-262 |
| 6 | 82429-82581 | 263-313 |

TABLE 1-continued

EXON/INTRON ORGANIZATION OF THE
HUMAN CARBOXY-PEPTIDASE M GENE
(cDNA ACCESSION NO. XM_006768)
IN SEQ ID NO: 3,99680 BASE PAIRS;
NUCLEOTIDES 1-99680 IN THE GENOMIC
CLONE OF ACCESSION NO. AC025423
(FORWARD STRAND CODING).

| EXON | NUCLEOTIDE NO. | AMINO ACID NO. |
|---|---|---|
| 7 | 90406-90555 | 314-363 |
| 8 | 92799-93038 | 364-443 |
| STOP CODON | 93039-93041 | |

TABLE 2

EXON/INTRON ORGANIZATION OF THE
HUMAN MOUSE DOUBLE MINUTE 2
HOMOLOG GENE (VARIANT OF ACCESSION
NO. NM_002392) IN SEQ ID NO:4,51039 BASE PAIRS;
NUCLEOTIDES 99541-150579 IN THE GENOMIC CLONE OF
ACCESSION NO. ACO25423 (REVERSE STRAND CODING).

| EXON | NUCLEOTIDE NO. | AMINO ACID NO. |
|---|---|---|
| STOP CODON | 10089-10091 | |
| 10 | 10092-10664 | 491-301 |
| 9 | 13189-13266 | 300-275 |
| 8 | 13954-14109 | 274-223 |
| 7 | 21007-21168 | 222-169 |
| 6 | 25288-25383 | 168-137 |
| 5 | 25508-25576 | 136-114 |
| 4 | 29565-29615 | 113-97 |
| 3 | 32995-33126 | 96-53 |
| 2 | 36310-36384 | 52-28 |
| 1 | 40646-40726 | 27-1 |

TABLE 3

TRANSCRIPTION FACTOR BINDING SITES
ON GENES THAT ENCODE CARBOXYPEPTIDASE M (CpM)
AND THE HUMAN HOMOLOG OF MOUSE DOUBLE
MINUTE 2 (huMDM2)

| BINDING SITES | CpM | huMDM2 |
|---|---|---|
| AP1FJ_Q2 | 60 | 25 |
| ANS | 16 | 11 |
| AP1_Q2 | 39 | 13 |
| AP1_Q4 | 24 | 12 |
| AP4_Q5 | 47 | 27 |
| AP4_Q6 | 22 | 14 |
| ARNT_01 | | 4 |
| BRN2_01 | 29 | 6 |
| CAAT_01 | 7 | 4 |
| CDPCR3HD_01 | 19 | 7 |
| CEBPB_01 | 26 | 6 |
| CMYB_01 | 7 | |
| CREL_01 | 15 | 4 |
| DELTAEF1_01 | 196 | 98 |
| FREAC7_01 | 30 | 29 |
| GATA1_02 | 40 | 25 |
| GATA1_03 | 63 | 21 |
| GATA1_04 | 109 | 46 |
| GATA1_05 | 21 | 13 |
| GATA1_06 | 33 | 26 |
| GATA2_02 | 59 | 35 |
| GATA2_03 | 20 | 19 |
| GATA3_02 | 30 | 23 |
| GATA3_03 | 18 | 20 |
| GATA_C | 61 | 15 |
| GFII_01 | 23 | 8 |
| HFH2_01 | 20 | 13 |
| HFH3_01 | 32 | 13 |
| HFH8_01 | 23 | 7 |

TABLE 3-continued

TRANSCRIPTION FACTOR BINDING SITES
ON GENES THAT ENCODE CARBOXYPEPTIDASE M (CpM)
AND THE HUMAN HOMOLOG OF MOUSE DOUBLE
MINUTE 2 (huMDM2)

| BINDING SITES | CpM | huMDM2 |
|---|---|---|
| HNF3B_01 | 10 | 7 |
| IK1_01 | 12 | |
| IK2_01 | 216 | 63 |
| LMO2COM_01 | 86 | 23 |
| LMO2COM_02 | 85 | 23 |
| LYF1_01 | 45 | 41 |
| MAX_01 | 8 | 4 |
| MYCMAX_02 | 8 | |
| MYOD_O1 | 5 | |
| MYOD_Q6 | 49 | 21 |
| MZF1_01 | 187 | 61 |
| NF1_Q6 | 10 | 5 |
| NFAT_Q6 | 134 | 71 |
| NFY_Q6 | 16 | |
| NKX25_01 | 48 | 35 |
| NKX25_02 | 30 | 9 |
| NMYC_01 | 16 | 10 |
| OCT1_01 | 3 | |
| OCT1_02 | 6 | |
| OCT1_06 | 3 | |
| OCT1_07 | 5 | |
| OCT1_Q6 | 5 | |
| RORA1_01 | 8 | 9 |
| S8_01 | 183 | 128 |
| SOX5_01 | 76 | 29 |
| SRY_02 | 38 | 27 |
| STAT_01 | 11 | |
| TATA_01 | 28 | 22 |
| TATA_C | 20 | 8 |
| TCF11_01 | 182 | 51 |
| USF_01 | 16 | 10 |
| USF_C | 16 | 10 |
| VMYB_02 | 7 | 11 |
| XFD2_01 | 11 | 8 |

In a specific embodiment, such noncoding sequences are expression control sequences. These include but are not limited to DNA regulatory sequences, such as promoters, enhancers, repressors, terminators, and the like, that provide for the regulation of expression of a coding sequence in a host cell. In eukaryotic cells, polyadenylation signals are also control sequences.

In a more specific embodiment of the invention, the expression control sequences may be operatively linked to a polynucleotide encoding a heterologous polypeptide. Such expression control sequences may be about 50-200 nucleotides in length and specifically about 50, 100, 200, 500, 600, 1000 or 2000 nucleotides in length. A transcriptional control sequence is "operatively linked" to a polynucleotide encoding a heterologous polypeptide sequence when the expression control sequence controls and regulates the transcription and translation of that polynucleotide sequence. The term "operatively linked" includes having an appropriate start signal (e.g., ATG) in front of the polynucleotide sequence to be expressed and maintaining the correct reading frame to permit expression of the DNA sequence under the control of the expression control sequence and production of the desired product encoded by the polynucleotide sequence. If a gene that one desires to insert into a recombinant DNA molecule does not contain an appropriate start signal, such a start signal can be inserted upstream (5') of and in reading frame with the gene.

The invention is further directed to antisense oligonucleotides and mimetics to these polynucleotide sequences. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the mature polypeptides of the present invention, is used to design an antisense RNA oligonucleotide of from about 10 to 40 base pairs in length. A DNA oligonucleotide is designed to be complementary to a region of the gene involved in transcription or RNA processing (triple helix (see Lee et al., Nucl. Acids Res., 6:3073 (1979); Cooney et al, Science, 241:456 (1988); and Dervan et al., Science, 251: 1360 (1991)), thereby preventing transcription and the production of said polypeptides.

Expression of Polypeptides

Isolated Polynucleotide Sequences

The human chromosome 12 genomic clone of accession number AC025423 has been discovered to contain the human carboxypeptidase M gene and the human mouse double minute 2 homolog gene by Genscan analysis (Burge et al., 1997, J. Mol. Biol. 268:78-94), BLAST2 and TBLASTN analysis (Altschul et al., 1997, Nucl. Acids Res. 25:3389-3402), in which the sequence of AC025423 was compared to the human carboxypeptidase M cDNA sequence, accession number XM_006768 and the human mouse double minute 2 homolog cDNA sequence accession number NM_002392, one of several splice variants.

The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) or long range PCR may be used. In a specific embodiment, 5'- or 3'-non-coding portions of each gene may be identified by methods including but are not limited to, filter probing, clone enrichment using specific probes and protocols similar or identical to 5'- and 3'-"RACE" protocols which are well known in the art. For instance, a method similar to 5'-RACE is available for generating the missing 5'-end of a desired full-length transcript. (Fromont-Racine et al., 1993, Nucl. Acids Res. 21:1683-1684).

Once the DNA fragments are generated, identification of the specific DNA fragment containing the desired human carboxypeptidase M gene or the human mouse double minute 2 homolog gene may be accomplished in a number of ways. For example, if an amount of a portion of a human carboxypeptidase M gene or the human mouse double minute 2 homolog gene or its specific RNA, or a fragment thereof, is available and can be purified and labeled, the generated DNA fragments may be screened by nucleic acid hybridization to the labeled probe (Benton and Davis, 1977, Science 196:180; Grunstein and Hogness, 1975, Proc. Natl. Acad. Sci. U.S.A. 72:3961). The present invention provides such nucleic acid probes, which can be conveniently prepared from the specific sequences disclosed herein, e.g., a hybridizable probe having a nucleotide sequence corresponding to at least a 15 and preferably 40, nucleotide fragment of the sequences depicted in SEQ ID NOS:3 or 4. Preferably, a fragment is selected that is highly unique to the polypeptides of the invention. Those DNA fragments with substantial homology to the probe will hybridize. As noted above, the greater the degree of homology, the more stringent hybridization conditions can be used. In one embodiment, low stringency hybridization conditions are used to identify a homologous human carboxypeptidase M or human mouse double minute 2 homolog polynucleotide. However, in a preferred aspect, and as demonstrated experimentally herein, a nucleic acid encoding a polypeptide of the invention will hybridize to a nucleic acid derived from the polynucleotide sequence depicted in SEQ ID NOS:3 or 4 or a hybridizable fragment thereof, under moderately stringent conditions; more preferably, it will hybridize under high stringency conditions.

Alternatively, the presence of the gene may be detected by assays based on the physical, chemical, or immunological properties of its expressed product. For example, cDNA clones, or DNA clones which hybrid-select the proper mRNAs, can be selected which produce a protein that, e.g., has similar or identical electrophoretic migration, isoelectric focusing behavior, proteolytic digestion maps, or antigenic properties as known for the human carboxypeptidase M or human mouse double minute 2 homolog polypeptide.

A gene encoding human carboxypeptidase M or human mouse double minute 2 homolog polypeptide can also be identified by mRNA selection, i.e., by nucleic acid hybridization followed by in vitro translation. In this procedure, fragments are used to isolate complementary mRNAs by hybridization. Immunoprecipitation analysis or functional assays of the in vitro translation products of the products of the isolated mRNAs identifies the mRNA and, therefore, the complementary DNA fragments, that contain the desired sequences.

Nucleic Acid Constructs

The present invention also relates to nucleic acid constructs comprising a polynucleotide sequence containing the exon/intron segments of the human carboxypeptidase M gene (nucleotides 1-99680 of SEQ ID NO:3) or human mouse double minute 2 homolog gene (nucleotides 1-51039 of SEQ ID NO:4) operably linked to one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

The invention is further directed to a nucleic acid construct comprising expression control sequences derived from SEQ ID NOS: 3 or 4 and a heterologous polynucleotide sequence.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence of the present invention. The term "coding sequence" is defined herein as a portion of a nucleic acid sequence which directly specifies the amino acid sequence of its protein product. The boundaries of the coding sequence are generally determined by a ribosome binding site (prokaryotes) or by the ATG start codon (eukaryotes) located just upstream of the open reading frame at the 5'-end of the mRNA and a transcription terminator sequence located just downstream of the open reading frame at the 3'-end of the mRNA. A coding sequence can include, but is not limited to, DNA, cDNA, and recombinant nucleic acid sequences.

The isolated polynucleotide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The control sequence may be an appropriate promoter sequence, a nucleic acid sequence which is recognized by a host cell for expression of the nucleic acid sequence. The promoter sequence contains transcriptional control sequences that regulate the expression of the polynucleotide. The promoter may be any nucleic acid sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, the *Streptomyces coelicolor* agarase gene (dagA), the *Bacillus subtilis* levansucrase gene (sacB), the *Bacillus licheniformis* alpha-amylase gene (amyL), the *Bacillus stearothermophilus* maltogenic amylase gene (amyM), the *Bacillus amyloliquefaciens* alpha-amylase gene (amyQ), the *Bacillus licheniformis* penicillinase gene (penP), the *Bacillus subtilis* xylA and xylB genes, and the prokaryotic beta-lactamase gene (VIIIa-Komaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American,* 1980, 242: 74-94; and in Sambrook et al., 1989, supra.

Examples of suitable promoters for directing the transcription of the nucleic acid constructs of the present invention in a filamentous fungal host cell are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium oxysporum* trypsin-like protease (WO 96/00787), NA2-tpi (a hybrid of the promoters from the genes encoding *Aspergillus niger* neutral alpha-amylase and *Aspergillus oryzae* triose phosphate isomerase), and mutant, truncated, and hybrid promoters thereof.

In a yeast host, useful promoters are obtained from the *Saccharomyces cerevisiae* enolase (ENO-1) gene, the *Saccharomyces cerevisiae* galactokinase gene (GAL1), the *Saccharomyces cerevisiae* alcohol dehydrogenase/glyceraldehyde-3-phosphate dehydrogenase genes (ADH2/GAP), and the *Saccharomyces cerevisiae* 3-phosphoglycerate kinase gene. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3'-terminus of the nucleic acid sequence encoding the polypeptide. Any terminator which is functional in the host cell of choice may be used in the present invention. Preferred terminators for filamentous fungal host cells are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Preferred terminators for yeast host cells are obtained from the genes encoding *Saccharomyces cerevisiae* enolase, *Saccharomyces cerevisiae* cytochrome C (CYC1), or *Saccharomy-*

*ces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5'-terminus of the nucleic acid sequence encoding the polypeptide. Any leader sequence that is functional in the host cell of choice may be used in the present invention. Preferred leaders for filamentous fungal host cells are obtained from the genes encoding *Aspergillus oryzae* TAKA amylase and *Aspergillus nidulans* triose phosphate isomerase.

Suitable leaders for yeast host cells are obtained from the *Saccharomyces cerevisiae* enolase (ENO-1) gene, the *Saccharomyces cerevisiae* 3-phosphoglycerate kinase gene, the *Saccharomyces cerevisiae* alpha-factor, and the *Saccharomyces cerevisiae* alcohol dehydrogenase/glyceraldehyde-3-phosphate dehydrogenase genes (ADH2/GAP).

The control sequence may also be a polyadenylation sequence, a sequence which is operably linked to the 3'-terminus of the nucleic acid sequence and which, when transcribed, is recognized by the host cell as a signal to add polyadenosine residues to transcribed mRNA. Any polyadenylation sequence which is functional in the host cell of choice may be used in the present invention. Preferred polyadenylation sequences for filamentous fungal host cells are obtained from the genes encoding *Aspergillus oryzae* TAKA amylase, *Aspergillus niger* glucoamylase, *Aspergillus nidulans* anthranilate synthase, and *Aspergillus niger* alpha-glucosidase. Useful polyadenylation sequences for yeast host cells are described by Guo and Sherman, 1995, *Molecular Cellular Biology* 15: 5983-5990. The control sequence may also be a signal peptide coding region, which codes for an amino acid sequence linked to the amino terminus of the polypeptide which can direct the encoded polypeptide into the cell's secretory pathway.

The 5'-end of the coding sequence of the nucleic acid sequence may inherently contain a signal peptide coding region naturally linked in translation reading frame with the segment of the coding region which encodes the secreted polypeptide. Alternatively, the 5'-end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed polypeptide into the secretory pathway of a host cell of choice may be used in the present invention. An effective signal peptide coding region for bacterial host cells is the signal peptide coding region obtained from the maltogenic amylase gene from *Bacillus* NCIB 11837, the *Bacillus stearothermophilus* alpha-amylase gene, the *Bacillus licheniformis* subtilisin gene, the *Bacillus licheniformis* beta-lactamase gene, the *Bacillus stearothermophilus* neutral proteases genes (nprT, nprS, nprM), or the *Bacillus subtilis* prsA gene. Further signal peptides are described by Simonen and Palva, 1993, *Microbiological Reviews* 57: 109-137. An effective signal peptide coding region for filamentous fungal host cells is the signal peptide coding region obtained from the *Aspergillus oryzae* TAKA amylase gene, *Aspergillus niger* neutral amylase gene, *Aspergillus niger* glucoamylase gene, *Rhizomucor miehei* aspartic proteinase gene, *Humicola lanuginosa* cellulase gene, or *Humicola lanuginosa* lipase gene. Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the *Bacillus subtilis* alkaline protease gene (aprE), the *Bacillus subtilis* neutral protease gene (nprT), the *Saccharomyces cerevisiae* alpha-factor gene, the *Rhizomucor miehei* aspartic proteinase gene, or the *Myceliophthora thermophila* laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences that allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems would include the lac, tac, and trp operator systems. In yeast, the ADH2 system or GAL1 system may be used. In filamentous fungi, the TAKA alpha-amylase promoter, *Aspergillus niger* glucoamylase promoter, and the *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the polynucleotide of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*, or markers which confer antibiotic resistance such as ampicillin, kanamycin, chloramphenicol or tetracycline resistance. Suitable markers for yeast host cells are ADE2, HIS3, LEU2, LYS2, MET3, TRP1, and URA3. A selectable marker for use in a filamentous fungal host cell may be selected from the group including, but not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5Õ-phosphate decarboxylase), sC (sulfate adenyltransferase), trpC (anthranilate synthase), as well as equivalents from other species. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell genome or autonomous replication of the vector in the cell independent of the genome of the cell. For integration into the host cell genome, the vector may rely on the polynucleotide sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional polynucleotide sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*. Examples of origins of replication for use in a yeast host cell are the 2 micron origin of replication, ARS1, ARS4, the combination of ARS1 and CEN3, and the combination of ARS4 and CEN6.

The origin of replication may be one having a mutation which makes its functioning temperature-sensitive in the host cell (see, e.g., Ehrlich, 1978, *Proceedings of the National Academy of Sciences USA* 75: 1433).

More than one copy of a polynucleotide sequence of the present invention may be inserted into the host cell to increase production of the gene product. An increase in the copy number of the polynucleotide sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular cells are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus*, *Bacillus licheniformis*, *Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may be a eukaryote, such as a mammalian cell (e.g., human cell), an insect cell, a plant cell or a fungal cell. Mammalian host cells that could be used include but are not limited to human Hela, 293, H9 and Jurkat cells, mouse NIH3t3 and C127 cells, Cos 1, Cos 7 and CV1, quail QC1-3 cells, mouse L cells and Chinese Hamster ovary (CHO) cells. These cells may be transfected with a vector containing a transcriptional regulatory sequence, a protein coding sequence and transcriptional termination sequences. Alternatively, the polypeptide can be expressed in stable cell lines containing the polynucleotide integrated into a chromosome. The co-transfection with a selectable marker such as dhfr, gpt, neomycin, hygromycin allows the identification and isolation of the transfected cells.

The host cell may be a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). The fungal host cell may also be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980). The fungal host cell may also be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, Proceedings of the National Academy of Sciences USA 81: 1470-1474. Suitable methods for transforming Fusarium species are described by Malardier et al., 1989, Gene 78: 147-156 and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et al., 1978, Proceedings of the National Academy of Sciences USA 75: 1920.

Methods of Production

The present invention also relates to methods for producing a polypeptide of the present invention comprising (a) cultivating a host cell under conditions conducive for production of the polypeptide; and (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate. In a specific embodiment, an enzyme assay may be used to determine the activity of the polypeptide. For example, carboxypeptidase M activity can be determined by measuring the release of the C-terminal arginine of bradykinin or a synthetic acyl-dipeptide such as benzoyl-Ala-Arg. The human homolog of mouse double minute 2 may be detected by its ability to bind p53.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989).

Antibodies

According to the invention, the human carboxypeptidase M or human mouse double minute 2 homolog polypeptides produced according to the method of the present invention may be used as an immunogen to generate any of these antibodies. Such antibodies include but are not limited to polyclonal, monoclonal, chimeric, single chain, Fab fragments, and a Fab expression library.

Various procedures known in the art may be used for the production of antibodies. For the production of antibody, various host animals can be immunized by injection with the polypeptide thereof, including but not limited to rabbits, mice, rats, sheep, goats, etc. In one embodiment, the polypeptide or fragment thereof can optionally be conjugated to an immunogenic carrier, e.g., bovine serum albumin (BSA) or keyhole limpet hemocyanin (KLH). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and Corynebacterium parvum.

For preparation of monoclonal antibodies directed toward the human carboxypeptidase M or human mouse double minute 2 homolog polypeptide, any technique that provides for the production of antibody molecules by continuous cell lines in culture may be used. These include but are not limited to the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, J. Bacteriol. 159-870; Neuberger et al., 1984, Nature 312:604-608; Takeda et al., 1985, Nature 314:452-454) by splicing the genes from a mouse antibody molecule specific for the human carboxypeptidase M or human mouse double minute 2 homolog polypeptide together with genes from a human antibody molecule of appropriate biological activity can be used; such antibodies are within the scope of this invention.

According to the invention, techniques described for the production of single chain antibodies (U.S. Pat. No. 4,946,778) can be adapted to produce polypeptide-specific single chain antibodies. An additional embodiment of the invention utilizes the techniques described for the construction of Fab expression libraries (Huse et al., 1989, Science 246:1275-1281) to allow rapid and easy identification of monoclonal Fab fragments with the desired specificity for the human carboxypeptidase M or human mouse double minute 2 homolog polypeptide.

Antibody fragments that contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$, fragment, and the Fab fragments which can be generated by treating the antibody molecule with papain and a reducing agent.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. For example, to select antibodies which recognize a specific epitope of a particular polypeptide, one may assay generated hybridomas for a product which binds to a particular polypeptide fragment containing such epitope. For selection of an antibody specific to a particular polypeptide from a particular species of animal, one can select on the basis of positive binding with the polypeptide expressed by or isolated from cells of that species of animal.

Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Substrate

In a specific embodiment, the polynucleotides of the present invention, particularly, the polynucleotide fragments for hybridizing to non-coding regions of SEQ ID NOS:3 or 4 may be attached to a substrate or reverse complements of said fragments. A substrate may be solid or porous, planar or non-planar, unitary or distributed. The polynucleotide may be attached covalently or applied to a derivatized surface in a chaotropic agent that facilitates denaturation and adherence by presumed noncovalent interactions, or some combinations thereof.

In a more specific embodiment, the substrate is a microarray. "Microarray" as defined herein is a substrate-bound collection of a plurality nucleic acids, hybridization to each of the plurality of bound nucleic acids being separately detectable. The microarray may comprise a plurality of polynucleotides hybridizing to a non coding region of SEQ ID NO:3 or 4. Alternatively the microarray may comprise a polynucleotide(s) hybridizing to said non-coding region and/or coding regions of SEQ ID NO:3 or 4.

Uses of Polynucleotides

Diagnostics

Polynucleotide fragments containing noncoding regions of SEQ ID NO:3 or 4 may be used as probes for detecting variants from genomic nucleotide samples from a patient. The variants may be allelic variants or substitution, insertion or deletion nucleotide variants. Genomic DNA may be isolated from the patient. Alternatively the polynucleotide fragments may be used to monitor expression of SEQ ID NO:3 or 4 from samples from a patient. A mutation(s) may be detected by Southern blot analysis, for example, by hybridizing restriction digested genomic DNA to various probes between 10-500 nucleotides in length, preferably between 20-200 nucleotides in length, more preferably between 20-100 nucleotides in length and most preferably between 20-50 nucleotides in length and subjecting to agarose electrophoresis. Alternatively, these polynucleotides may be used as PCR primers between about 10-100 nucleotides in length and be used to amplify the genomic DNA isolated from the patients. Methods for performing primer-directed amplification (routine or long range PCR) are well known in the art (see, for example, PCR Basics: From Background to Bench, Springer Verlag (2000); Gelfand et al., (eds.), PCR Strategies, Academic Press (1998)). Single base extension (see, for example, U.S. Pat. No. 6,004,744) may be used to detect SNPs. Additionally, primers may be obtained by routine or long range PCR that yield products containing contiguous intron(s)/exon sequence(s) and products containing more than one exon with intervening intron(s). The sequence of the amplified genomic DNA from the patient may be determined using methods known in the art. Such probes may be between 20-5000 nucleotides in length and may preferably be between 20-50 nucleotides in length.

Thus the invention is directed to kits comprising these polynucleotide probes. In a specific embodiment, these probes are labeled with a detectable substance.

In one embodiment, the probes are in solution. In another embodiment, the probes are attached to a substrate. In a specific embodiment, the probes are contained within a microarray and are separately detectable. The probes or primers of the present invention could be used to identify patients with or having a propensity for sepsis (SEQ ID NO:3-carboxypeptidase M gene) or for sarcoma or leukemias (SEQ ID NO:4-human mouse double minute 2 homolog gene).

Antisense Oligonucleotides and Mimetics

The antisense or reverse complement oligonucleotides or mimetics of the present invention may be used to decrease levels of a polypeptide. For example, human carboxypeptidase M has been found to form des-Arg9-bradykinin, an agonist of the B1 receptor activated by sepsis. Therefore, the human carboxypeptidase M antisense oligonucleotides of the present invention could be used to inhibit formation of des-Arg9-bradykinin. Human mouse double minute 2 homolog antisense sequences may be used to treat sarcomas and leukemias in which the gene is over-expressed.

The antisense oligonucleotides of the present invention may be formulated into pharmaceutical compositions. These compositions may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention, the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$ as found to be effective in in vitro and in vivo animal models.

In general, dosage is from 0.01 ug to 10 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 10 g per kg of body weight, once or more daily, to once every 20 years.

Gene Therapy

As noted above, human carboxypeptidase M modulates actions of anaphylatoxins and kinins and human mouse double minute 2 homolog plays a role in cell proliferation. Therefore, the human carboxypeptidase M gene may be used to modulate or prevent complement-linked tissue damage, in subjects in need thereof, for example, those exhibiting allergic reactions to a given substance. The human mouse double minute 2 homolog gene may be used to stimulate cell proliferation in subjects in need thereof, for example, for wound healing and those suffering from neurodegenerative or neuromuscular diseases, ischemic stroke, anoxia, ischemia/reperfusion damage and intoxication septic shock.

As described herein, the polynucleotide of the present invention may be introduced into a patient's cells for therapeutic uses. As will be discussed in further detail below, cells can be transfected using any appropriate means, including viral vectors, as shown by the example, chemical transfectants, or physico-mechanical methods such as electroporation and direct diffusion of DNA. See, for example, Wolff, Jon A, et al., "Direct gene transfer into mouse muscle in vivo," *Science,* 247, 1465-1468, 1990; and Wolff, Jon A, "Human dystrophin expression in mdx mice after intramuscular injection of DNA constructs," *Nature,* 352, 815-818, 1991. As used herein, vectors are agents that transport the gene into the cell without degradation and include a promoter yielding expression of the gene in the cells into which it is delivered. As will be discussed in further detail below, promoters can be general promoters, yielding expression in a variety of mammalian cells, or cell specific, or even nuclear versus cytoplasmic specific. These are known to those skilled in the art and can be constructed using standard molecular biology protocols. Vectors have been divided into two classes: a) Biological agents derived from viral, bacterial or other sources and b) Chemical physical methods that increase the potential for gene uptake, directly introduce the gene into the nucleus or target the gene to a cell receptor.

Biological Vectors

Viral vectors have higher transaction (ability to introduce genes) abilities than do most chemical or physical methods to introduce genes into cells. Vectors that may be used in the present invention include viruses, such as adenoviruses, adeno associated virus (AAV), vaccinia, herpesviruses, baculoviruses and retroviruses, bacteriophages, cosmids, plasmids, fungal vectors and other recombination vehicles typically used in the art which have been described for expression in a variety of eukaryotic and prokaryotic hosts, and may be used for gene therapy as well as for simple protein expression. Polynucleotides are inserted into vector genomes using methods well known in the art.

Retroviral vectors are the vectors most commonly used in clinical trials, since they carry a larger genetic payload than other viral vectors. However, they are not useful in non-proliferating cells. Adenovirus vectors are relatively stable and easy to work with, have high titers, and can be delivered in aerosol formulation. Pox viral vectors are large and have several sites for inserting genes, they are thermostable and can be stored at room temperature.

Examples of promoters are SP6, T4, T7, SV40 early promoter, cytomegalovirus (CMV) promoter, mouse mammary tumor virus (MMTV) steroid-inducible promoter, Moloney murine leukemia virus (MMLV) promoter, phosphoglycerate kinase (PGK) promoter, and the like. Alternatively, the promoter may be an endogenous adenovirus promoter, for example the E1 a promoter or the Ad2 major late promoter (MLP). Similarly, those of ordinary skill in the art can construct adenoviral vectors utilizing endogenous or heterologous poly A addition signals. Plasmids are not integrated into the genome and the vast majority of them are present only from a few weeks to several months, so they are typically very safe. However, they have lower expression levels than retroviruses and since cells have the ability to identify and eventually shut down foreign gene expression, the continuous release of DNA from the polymer to the target cells substantially increases the duration of functional expression while maintaining the benefit of the safety associated with non-viral transfections.

Chemical/Physical Vectors

Other methods to directly introduce genes into cells or exploit receptors on the surface of cells include the use of liposomes and lipids, ligands for specific cell surface receptors, cell receptors, and calcium phosphate and other chemical mediators, microinjections directly to single cells, electroporation and homologous recombination. Liposomes are commercially available from Gibco BRL, for example, as LIPOFECTIN" and LIPOFECTACE", which are formed of cationic lipids such as N-[1-(2,3 dioleyloxy)-propyl]-n,n,n-trimethylammonium chloride (DOTMA) and dimethyl dioctadecylammonium bromide (DDAB). Numerous methods are also published for making liposomes, known to those skilled in the art.

For example, Nucleic acid-Lipid Complexes—Lipid carriers can be associated with naked nucleic acids (e.g., plasmid DNA) to facilitate passage through cellular membranes. Cationic, anionic, or neutral lipids can be used for this purpose. However, cationic lipids are preferred because they have been shown to associate better with DNA which, generally, has a negative charge. Cationic lipids have also been shown to mediate intracellular delivery of plasmid DNA (Feigner and Ringold, Nature 337:387 (1989)). Intravenous injection of cationic lipid-plasmid complexes into mice has been shown to result in expression of the DNA in lung (Brigham et al., Am. J. Med. Sci. 298:278 (1989)). See also, Osaka et al., J. Pharm. Sci. 85(6):612-618 (1996); San et al., Human Gene Therapy 4:781-788 (1993); Senior et al., Biochemica et Biophysica Acta 1070:173-179 (1991); Kabanov and Kabanov, Bioconjugate Chem. 6:7-20 (1995); Remy et al., Bioconjugate Chem. 5:647-654 (1994); Behr, J-P., Bioconjugate Chem 5:382-389 (1994); Behr et al., Proc. Natl. Acad. Sci., USA 86:6982-6986 (1989); and Wyman et al., Biochem. 36:3008-3017 (1997).

Cationic lipids are known to those of ordinary skill in the art. Representative cationic lipids include those disclosed, for example, in U.S. Pat. No. 5,283,185; and e.g., U.S. Pat. No. 5,767,099. In a preferred embodiment, the cationic lipid is N.sup.4-spermine cholesteryl carbamate (GL-67) disclosed in U.S. Pat. No. 5,767,099. Additional preferred lipids include N4_spermidine cholestryl carbamate (GL-53) and 1-(N4-spermind)-2,3-dilaurylglycerol carbamate (GL-89).

The vectors of the invention may be targeted to specific cells by linking a targeting molecule to the vector. A targeting molecule is any agent that is specific for a cell or tissue type of interest, including for example, a ligand, antibody, sugar, receptor, or other binding molecule.

Invention vectors may be delivered to the target cells in a suitable composition, either alone, or complexed, as provided above, comprising the vector and a suitably acceptable carrier. The vector may be delivered to target cells by methods known in the art, for example, intravenous, intramuscular, intranasal, subcutaneous, intubation, lavage, and the like. The vectors may be delivered via in vivo or ex vivo applications. In vivo applications involve the direct administration of an adenoviral vector of the invention formulated into a composition to the cells of an individual. Ex vivo applications involve the transfer of the adenoviral vector directly to harvested autologous cells which are maintained in vitro, followed by readministration of the transduced cells to a recipient.

In a specific embodiment, the vector is transfected into antigen-presenting cells. Suitable sources of antigen-presenting cells (APCs) include, but are not limited to, whole cells such as dendritic cells or macrophages; purified MHC class 1 molecule complexed to beta2-microglobulin and foster antigen-presenting cells. In a specific embodiment, the vectors of the present invention may be introduced into T cells or B cells using methods known in the art (see, for example, Tsokos and Nepom, 2000, J. Clin. Invest. 106:181-183).

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for isolating a nucleic acid molecule 20-51039 contiguous nucleotides in length consisting of a reverse or forward strand of a region of SEQ ID NO:4, wherein said region is selected from the group consisting of a 5'-non coding region between nucleotides 51039-41739 of SEQ ID NO:4; a 3'-non-coding region between nucleotides 9503-1 of SEQ ID NO:4; a contiguous intron-exon region between nucleotides 41738-9502 of SEQ ID NO:4, wherein a sequence segment between nucleotides 41738-9502 of SEQ ID NO:4 encodes human mouse double minute 2 homolog depicted in SEQ ID NO:2; a contiguous exon-intron region between nucleotides 41738-9502 of SEQ ID NO:4, wherein a sequence segment between nucleotides 41738-9502 of SEQ ID NO:4 encodes human mouse double minute 2 homolog depicted in SEQ ID NO:2; an intron depicted in nucleotides 36385-40645, 36309-33127, 32994-29616, 29564-25577, 25507-25384, 25287-21169, 21006-14110, 13953-13267, and/or 13188-10665; a region comprising a dinucleotide of the following group: 41739-41738, 40645-40646, 36309-36310, 36384-36385, 32994-32995, 33126-33127, 29564-29565, 29615-29616, 25507-25508, 25287-25288, 25383-25384, 25576-25577, 21006-21007, 21168-21169, 14109-14110, 13953-13954, 13266-13267, 13188-13189, 10664-10665 and/or 9504-9503; a transcription binding site selected from the group consisting of
BINDING SITES huMDM2, location in SEQ ID NO:4
AP1_C: 36-46, 2876-2886;
AP4_Q5: 7944-7980;
AP4_Q6: 7943-59, 8924-8940, 9294-9310;
ARNT_01: 1682-1706, 2193-2217, 9201-9225;
BRN2_01: 1040-1058, 7803-7821;
CAAT_01: 3292-3306;
CDPCR3HD_01: 6522-6540;
CEBPB_01: 1424-1438, 3917-3931, 4178-4192, 4787-4801, 6855-6869;
CREL_01: 5630-5642;
DELTAEF1_01: 83-95, 6328-6340;
FREAC7_01: 2757-2773, 5154-5170, 5823-5839;
GATA1_04: 4846-4858, 7017-7029;
GATA1_05: 8464-8476;
GATA2_02: 6045-6057, 6073-6085, 6142-6154;
GATA2_03: 2489-2501, 3323-3335, 3384-3396, 7393-7405:
GATA3_02: 3264-3276, 6870-6882:
GATA3_03: 40-52, 5729-5741, 6529-6541, 6874-6886, 7041-7053, 7589-7601;
GATA_C: 7 349-7361, 8188-8200;
HFH2_01: 1743-1759, 7995-8011;
HFH3_01: 502-518, 1739-1755, 4160-4176, 9402-9418, 9418-9434;
HFH8_01: 8184-8200;
IK2_01: 951-963, 3588-3600;
MZF1_01: 1202-1210, 1447-1455, 4997-4005, 5424-5432;
NF1_Q6: 1480-1500, 8166-8182;
NFAT_Q6: 4190-4208, 6009-6027;
NKX25_01: 741-755, 1648-1662, 1885-1899, 1984-1998, 3609-3623, 4928-4942, 5060-5074, 5889-5903, 8850-8864, 9190-9204;
NKX25_02: 2584-2599, 2970-2984, 4644-4658, 5179-5193, 6482-6496;
NMYC_01: 2560-2572;
RORA101: 220-238, 2638-2656;

S8_01: 4644-4656, 4842-4854, 4845-4857, 5200-5212, 5371-5383, 5735-5747, 6482-6494, 6541-6553, 6544-6556, 6772-6784, 7270-7292, 7273-7285;
SOX5_01: 1355-1371, 1430-1446, 3094-3110, 3155-3171, 4669-4685, 4692-4708, 4789-4805;
SRY_02: 4164-4180, 5665-5681;
TATA_01: 1261-1277, 2574-2590, 2723-2739, 2733-2749, 2770-2786, 4199-4215, 4206-4222;
TATA_C: 5900-5916, 7456-7472, 7702-7718, 7917-7933; and
XFD2_01: 7702-7218, 7917-7933;
a transcription binding site selected from the group consisting of
BINDING SITES huMDM2, location in SEQ ID NO:4
ANS: 12109-12119, 12695-12705, 22600-22610, 24166-24176, 31311-31321, 35234-35244, 39184-39194;
AP1_Q2: 11952-11962, 12068-12078, 14798-14808, 21748-21758, 22613-22623, 23676-23686, 26562-26572, 30046-30056;
AP1_Q4: 12695-12705, 31311-31321, 35234-35244, 36295-36305, 38784-38794, 39188-39198;
AP4_Q6: 31635-31651;
BRN2_01: 13448-13466, 14764-14782, 28094-28112, 40027-40045;
CAAT_01: 11288-11302, 15054-15068;
CDPCR3HD_01: 11286-11304, 13284-13302, 20846-20864, 29344-29362;
CEBPB_01: 29241-29255;
CREL_01: 36091-36103, 38873-38885;
DELTAEF1_01: 18083-18095, 20385-20397, 26955-26967;
FREAC7_01: 11982-11998, 15187-15202, 16523-16539, 16529-16545, 16587-16603, 16604-16620, 16676-16642, 16633-16649, 16644-16660, 16650-16666, 16657-16673, 16673-16689, 16762-16778, 21332-21348, 25689-25700, 26529-26545, 27767-27783, 29495-29511;
GATA1_02: 10916-10928, 15775-15789, 18162-18174, 26088-26100, 32518-32530;
GATA1_03: 28012-28024;
GATA1_04: 11153-11165, 11630-11642, 13778-13790, 17439-17451, 19300-19312, 21606-21618, 22743-22755, 23747-23759, 25806-25818, 26529-26541, 29424-29436, 30455-30467, 32761-32778, 33352-33364, 33960-33972, 36101-36113, 40007-40019;
GATA1_05: 11590-11602, 26550-26562, 36737-36749;
GATA1_06: 18772-18784, 23054-23066, 35568-35580, 37855-37867;
GATA2_02: 20755-20767, 30830-30842, 34755-34767, 36285-36297, 39143-39155, 39641-39653, 40586-40598;
GATA2_03: 13535-13547, 22711-22723, 23161-23173, 25028-25040, 27237-27249, 36277-36289;
GATA3_02: 11558-11570, 16470-16482, 17225-17237, 19619-19631, 22156-22168, 22443-22455, 24713-24725, 27619-27631, 32716-32728, 34124-34136, 34163-34175, 36832-36844, 38403-38415;
GATA3_03: 10869-10881, 11515-11527, 13845-13857, 17221-17233, 18952-18964, 20050-20062, 40171-40183;
GATA_C: 15848-15860, 18899-18911, 23640-23652, 29072-29084, 30881-30893, 33198-33210, 37472-37484, 38621-38633;
GFI1_01: 35469-35481, 35492-35504;
HFH2_01: 15939-15955, 24636-24652, 25866-25882, 32171-32187, 35372-35388, 39457-35473;
HFH3_01: 13340-13356, 19218-19234, 21328-21344, 21336-21352, 21344-21360, 28062-28078, 32125-32141;
HFH8_01: 14133-14149, 22578-22584;
HNF3B_01: 13150-13166, 16505-16521, 25264-25280, 29443-29459, 37654-37670;
IK2_01: 11547-11559, 17144-17156, 18961-18973, 23883-23895, 27617-27629, 28908-28920, 29241-29253, 30752-30764, 34768-34780;
LYF1_01: 12319-12331, 19191-19203, 37226-37238, 39430-39442;
MAX_01: 22974-22986, 33339-33351;
MZF1_01: 26105-26113, 35187-35195;
NF1_Q6: 12048-12064, 33334-33354;
NFAT_Q6: 13295-13313, 14157-14175, 14311-14329, 14414-14432, 18269-18287, 19326-19344, 20801-20819, 21177-21195, 22537-22555, 23861-23879, 25392-25410, 25879-25897, 27524-27542, 30636-30654, 30718-30736, 31525-31543, 33655-33673, 34726-34744, 34917-34535, 34990-35008, 35979-35997, 36479-36493, 36577-36595, 37154-37172, 40224-40242, 40365-40383;
NKX25_01: 12041-12055, 12340-12354, 12471-12485, 12742-12756, 12877-12891, 13849-13863, 18995-19009, 21440-21454, 21883-21897, 28426-28440, 30964-30978, 32033-32047, 32265-32279;
NKX25_02: 10998-11012, 12711-12725, 14131-14145, 14726-14740, 16024-16038;
NMYC_01: 18753-18765, 18754-18766, 23076-23088, 30534-30546, 34400-34412;
RORA101: 13134-13152, 22966-22984, 24934-24952, 33341-33359, 34760-34778;
S8_01: 11000-11012, 11977-11989, 12048-12060, 12051-12063, 13747-13759, 13923-13935, 13926-13938, 14676-14688, 14679-14691, 16026-16038, 16313-16325, 16316-16328, 17515-17527, 20756-20768, 20759-20771, 23154-23166, 23157-23169, 25198-25210, 25201-25213, 26651-26663, 27508-27520, 27511-27523, 29450-29462, 29478-28490, 29775-29787, 29778-29790, 29813-29825, 29816-29828, 31329-31341, 31677-31689, 31680-31692, 31732-31744, 31735-31747, 36137-36149, 36140-36152, 36812-36824, 36815-36827, 37413-37425, 38679-38691, 39474-39486, 39477-39489;
SOX5_01: 27397-27413, 27572-27588, 28100-28116, 29230-29246, 29439-29455, 30690-30706, 31595-31611, 33871-33887, 34113-34129, 34624-34640, 37668-37684, 38582-38598, 39124-39140, 40410-40426;
SRY_02: 20016-20032, 22410-22426, 27329-27345, 29162-29178, 29499-29515, 30646-30662, 31503-31519, 35928-35944, 37324-37340;
TATA_01: 32722-32738, 32729-32745, 32807-32823, 33825-33841, 34120-34136, 35433-35449, 36593-36609;
TATA_C: 11015-11031, 11817-11833, 13635-13651, 14930-14946;
TCF11_01: 18543-18549, 22574-22580, 31281-31297, 31489-31505, 38754-38770;
USF_01: 23075-23087, 32577-32589;
VMYB_02: 11526-11538, 17384-17396, 18400-18412, 19549-19561, 22188-22200, 40486-40508 and
XFD2_01: 16620-16636, 18153-18169, 22102-22118, 23141-23157;

And a transcription binding site selected from the group consisting of
BINDING SITES
huMDM2,1 location in SEQ ID NO:4
AP1_C: 44584-44594, 49069-49079:
AP1_Q2: 42174-42184, 45217-45227, 48422-48422, 50447-50457;
AP1_Q4: 42702-42712, 50806-50816;
AP4_Q6: 42117-42133, 42118-42134, 42244-42260, 45432-45448; 45433-45449, 46609-46625;
BRN2_01: 42310-42328, 44022-44040, 47514-47532, 48900-48918, 48967-48985;
CAAT_01: 44866-44880;
CDPCR3HD_01: 45671-45689, 49219-49237;
CREL_01: 42437-42449, 49797-49809;
FREAC701: 47026-47042, 47292-47308, 47658-47674;
GATA1_02: 43482-43494, 48926-48938, 49284-49296;
GATA1_03: 47371-47383;
GATA1_04: 43054-43066, 43162-43162, 43967-43979, 45464-45476, 45916-45928, 47763-47775;
GATA1_05: 49319-49331, 49459-49471;
GATA1_06: 47590-47602;
GATA2_02: 42660-42672, 43475-43487;
GATA2_03: 43714-43726, 50948-50960;
GATA3_02: 49155-49167, 49844-49856;
GATA3_03: 42202-42214, 44810-44822, 48438-48450, 49136-49148, 49337-49349, 49869-49881;
GATA_C: 44011-44023, 45256-45268, 45823-45835, 47915-47927, 49201-49213, 49573-49585;
GFI1_01: 46606-46618, 47063-47075;
HFH301: 47030-47046, 47284-47300, 47288-47304;
IK2_01: 45275-45287;
LYF1_01: 44564-44576, 46991-47003, 49567-49579;
MAX_01: 43234-43246, 48726-48738;
MZF1_01: 41772-41780, 42290-42298, 42295-42303, 44507-44515, 45105-45113, 45203-45211, 49948-49956, 50774-50782;
NF1_Q6: 50209-50229;
NFAT_Q6: 42061-42079, 44418-44436, 46399-46417, 47974-47992, 49267-49285, 49964-49982, 50392-50410;
NKX25_01: 42394-42408, 43507-43521, 46115-46129;
RORA1_01: 45073-45091, 48718-48736;
S8_01: 43552-43564, 45214-45226, 47160-47172, 48419-48431, 49295-49307, 50379-50391;
SOX5_01: 43716-43732, 46351-46367, 47156-47172, 47774-47790, 47868-47884, 47974-47990, 48915-48931, 50323-50339;
TATA_01: 45588-45604, 47625-47641, 48026-48042, 48659-48675, 49056-49072, 49079-49095, 49152-49168;
TCF11_01: 49115-49131;
VMYB_02: 42010-42022, 42279-42291, 44651-44663; and
XFD2_01: 42870-42886, 42910-42926
Comprising
  (a) isolating genomic DNA from a subject;
  (b) providing primers, probes and optionally polymerase and
  (c) incubating (a) and (b) under conditions promoting the isolation of said nucleic acid molecule.

* * * * *